US010080721B2

(12) United States Patent
Barnscheid et al.

(10) Patent No.: US 10,080,721 B2
(45) Date of Patent: Sep. 25, 2018

(54) HOT-MELT EXTRUDED PHARMACEUTICAL DOSAGE FORM

(75) Inventors: Lutz Barnscheid, Mönchengladbach (DE); Eric Galia, Inden (DE)

(73) Assignee: GRUENENTHAL GMBH, Aachen (DE)

( * ) Notice: Subject to any disclaimer, the term of this patent is extended or adjusted under 35 U.S.C. 154(b) by 363 days.

(21) Appl. No.: 12/840,439

(22) Filed: Jul. 21, 2010

(65) Prior Publication Data

US 2011/0038930 A1    Feb. 17, 2011

(30) Foreign Application Priority Data

Jul. 22, 2009  (EP) ..................................... 09009499

(51) Int. Cl.
*A61K 9/22*   (2006.01)
*A61K 9/20*   (2006.01)
*A61K 31/137* (2006.01)

(52) U.S. Cl.
CPC .......... *A61K 9/2072* (2013.01); *A61K 9/2031* (2013.01); *A61K 9/2054* (2013.01); *A61K 9/2095* (2013.01); *A61K 31/137* (2013.01)

(58) Field of Classification Search
USPC ........................................................ 424/468
See application file for complete search history.

(56) References Cited

U.S. PATENT DOCUMENTS

| | | |
|---|---|---|
| 2,524,855 A | 10/1950 | Schnider et al. |
| 2,806,033 A | 9/1957 | Lewenstein et al. |
| 2,987,445 A | 6/1961 | Levesque |
| 3,332,950 A | 7/1967 | Blumberg et al. |
| 3,370,035 A | 2/1968 | Ogura et al. |
| 3,652,589 A | 3/1972 | Flick et al. |
| 3,806,603 A | 4/1974 | Gaunt et al. |
| 3,865,108 A | 2/1975 | Hartop |
| 3,941,865 A | 3/1976 | Miller et al. |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Anderson et al. |
| 4,207,893 A | 6/1980 | Michaels |
| 4,262,017 A | 4/1981 | Kuipers |
| 4,343,789 A | 8/1982 | Kawata et al. |
| 4,353,887 A | 10/1982 | Hess et al. |
| 4,404,183 A | 9/1983 | Kawata et al. |
| 4,427,681 A | 1/1984 | Munshi et al. |
| 4,427,778 A | 1/1984 | Zabriskie |
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,485,211 A | 11/1984 | Okamoto |
| 4,529,583 A | 7/1985 | Porter |
| 4,599,342 A | 7/1986 | La Hann |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |

(Continued)

FOREIGN PATENT DOCUMENTS

| | | |
|---|---|---|
| AR | 46994 A1 | 12/2004 |
| AR | 045353 A1 | 10/2005 |
| AR | 049562 A1 | 8/2006 |
| AR | 053304 A1 | 5/2007 |
| AR | 054222 A1 | 6/2007 |
| AR | 054328 A1 | 6/2007 |
| AU | 769807 B2 | 3/2001 |
| AU | 2003237944 A1 | 12/2003 |
| AU | 2003274071 A1 | 5/2004 |
| AU | 2003278133 A1 | 5/2004 |

(Continued)

OTHER PUBLICATIONS

W.A. Ritschel et al, "Die Tablette", 2nd Edition, Editio Cantor Verlag Aulendorf, 2002.
M. V. S. Varma et al, Healthcare Technology Review, Am. J. Drug Deliv. 2004, 2(1), 43-57.

(Continued)

*Primary Examiner* — Devang K Thakor
(74) *Attorney, Agent, or Firm* — Norris McLaughlin & Marcus, P.A.

(57) ABSTRACT

The invention relates to a hot-melt extruded pharmaceutical dosage form with controlled release of a pharmacologically active ingredient (A) embedded in a matrix comprising a polymer (C), the dosage form exhibiting a breaking strength of at least 300 N and having an oblong shape comprising a longitudinal direction of extension, a transversal direction of extension orthogonal to the longitudinal direction of extension, a front side, an opposite back side and a circumferential rim between said front and back side;
wherein
 the core of the pharmaceutical dosage form has a morphological orientation caused by hot-melt extrusion that is substantially orthogonal to the longitudinal direction of extension of the dosage form; and/or
 the release per area of the pharmacologically active ingredient (A) through the front side and the opposite back side is faster than the release through the circumferential rim.

14 Claims, 13 Drawing Sheets

(56) References Cited

U.S. PATENT DOCUMENTS

| | | |
|---|---|---|
| 4,954,346 A | 9/1990 | Sparta et al. |
| 4,957,668 A | 9/1990 | Placard |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinity |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | McGinity et al. |
| 5,229,164 A | 7/1993 | Pins et al. |
| 5,273,758 A | 12/1993 | Royce |
| 5,326,852 A | 7/1994 | Fujikake et al. |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,679,685 A | 10/1997 | Cincotta et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Gradums et al. |
| 5,811,126 A | 9/1998 | Krishnamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,914,132 A | 6/1999 | Kelm et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,235,825 B1 | 2/2001 | Yoshida et al. |
| 6,228,863 B1 | 5/2001 | Palermo et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,322,819 B1 | 11/2001 | Burnside et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,455,052 B1 | 9/2002 | Marcussen et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breitenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric et al. |
| 8,101,630 B2 | 1/2012 | Kumar et al. |
| 8,114,383 B2 | 2/2012 | Bartholomaus et al. |
| 8,114,384 B2 | 2/2012 | Arkenau et al. |
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomaus et al. |
| 8,309,122 B2 | 11/2012 | Kao et al. |
| 8,323,889 B2 | 12/2012 | Arkenau-Maric et al. |

(56) References Cited

U.S. PATENT DOCUMENTS

| | | |
|---|---|---|
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Maric et al. |
| 8,858,963 B1 | 10/2014 | Devarakonda et al. |
| 9,192,578 B2 | 11/2015 | McGinity et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0187192 A1 | 2/2002 | Arilla et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iyer et al. |
| 2002/0176888 A1 | 11/2002 | Bartholomaeus et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0031546 A1 | 2/2003 | Araki et al. |
| 2003/0044458 A1 | 3/2003 | Wright et al. |
| 2003/0044464 A1 | 3/2003 | Zeigler et al. |
| 2003/0064099 A1 | 4/2003 | Oshlack et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0091630 A1 | 5/2003 | Louie-Helm et al. |
| 2003/0092724 A1 | 5/2003 | Huaihung et al. |
| 2003/0104052 A1 | 6/2003 | Berner et al. |
| 2003/0104053 A1 | 6/2003 | Gusler et al. |
| 2003/0118641 A1 | 6/2003 | Maloney |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0170680 A1 | 9/2004 | Oshlack et al. |
| 2004/0185105 A1 | 9/2004 | Berner et al. |
| 2004/0213845 A1 | 10/2004 | Sugihara |
| 2004/0213848 A1 | 10/2004 | Li et al. |
| 2005/0015730 A1 | 1/2005 | Gunturi et al. |
| 2005/0031546 A1 | 2/2005 | Bartholomaus et al. |
| 2005/0058706 A1 | 3/2005 | Bartholomaeus et al. |
| 2005/0063214 A1 | 3/2005 | Takashima |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaeus et al. |
| 2005/0191352 A1 | 9/2005 | Hayes |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |
| 2005/0245556 A1 | 11/2005 | Brogmann et al. |
| 2005/0266084 A1 | 12/2005 | Li et al. |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedman et al. |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaus et al. |
| 2006/0193914 A1* | 8/2006 | Ashworth et al. ............ 424/469 |
| 2006/0194759 A1 | 8/2006 | Eidelson |
| 2006/0194826 A1 | 8/2006 | Oshlack et al. |
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0259045 A1 | 11/2007 | Mannion et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0020032 A1 | 1/2008 | Crowley et al. |
| 2008/0023452 A1 | 1/2008 | Grek et al. |
| 2008/0063725 A1 | 3/2008 | Guimberteau et al. |
| 2008/0069871 A1 | 3/2008 | Vaughn et al. |
| 2008/0075669 A1 | 3/2008 | Soscia et al. |
| 2008/0075768 A1 | 3/2008 | Vaughn et al. |
| 2008/0081290 A1 | 4/2008 | Wada et al. |
| 2008/0085304 A1 | 4/2008 | Baichwal et al. |
| 2008/0131503 A1 | 6/2008 | Holm et al. |
| 2008/0145429 A1 | 6/2008 | Leyenecker et al. |
| 2008/0152595 A1 | 6/2008 | Emigh et al. |
| 2008/0181932 A1 | 7/2008 | Bortz et al. |
| 2008/0220079 A1 | 9/2008 | Chen |
| 2008/0233178 A1 | 9/2008 | Reidenberg et al. |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0280975 A1 | 11/2008 | Badul |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317695 A1 | 12/2008 | Everaert et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |

(56) References Cited

U.S. PATENT DOCUMENTS

| | | |
|---|---|---|
| 2009/0081290 A1 | 3/2009 | Kckenna et al. |
| 2009/0117191 A1 | 5/2009 | Brown Miller et al. |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0317355 A1 | 12/2009 | Roth et al. |
| 2009/0318395 A1 | 12/2009 | Schramm et al. |
| 2010/0015223 A1 | 1/2010 | Cailly-Deufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0082214 A1 | 4/2011 | Fauer et al. |
| 2011/0092515 A1 | 4/2011 | Qiu et al. |
| 2011/0097404 A1 | 4/2011 | Oshlack et al. |
| 2011/0129535 A1 | 6/2011 | Mantelle |
| 2011/0159100 A1 | 6/2011 | Anderson et al. |
| 2011/0187017 A1 | 8/2011 | Haupts |
| 2011/0223244 A1 | 9/2011 | Liversidge et al. |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0321716 A1 | 12/2012 | Vachon et al. |
| 2013/0028970 A1 | 1/2013 | Schwier et al. |
| 2013/0090349 A1 | 4/2013 | GeiLer et al. |
| 2013/0129825 A1 | 5/2013 | Billoet et al. |
| 2013/0129826 A1 | 5/2013 | GeiLer et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomäus et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau-Maric et al. |
| 2014/0112989 A1 | 4/2014 | Bartholomäus et al. |
| 2014/0170079 A1 | 6/2014 | Arkenau Maric et al. |
| 2014/0186440 A1 | 7/2014 | Han et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wening et al. |
| 2015/0030677 A1 | 1/2015 | Adjei et al. |
| 2015/0064250 A1 | 3/2015 | Ghebre-Sellassie et al. |
| 2015/0079150 A1 | 3/2015 | Fischer et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0374630 A1 | 12/2015 | Arkenau Maric et al. |
| 2016/0175256 A1 | 6/2016 | Bartholomaeus et al. |
| 2016/0184297 A1 | 6/2016 | Arkenau-Maric et al. |
| 2016/0256456 A1 | 9/2016 | Caruso et al. |
| 2016/0263037 A1 | 9/2016 | Arkenau-Maric et al. |
| 2016/0361308 A1 | 12/2016 | Bartholomaeus et al. |
| 2016/0367549 A1 | 12/2016 | Bartholomaeus et al. |
| 2017/0027886 A1 | 2/2017 | Bartholomaeus et al. |

FOREIGN PATENT DOCUMENTS

| | | |
|---|---|---|
| AU | 2003279317 A1 | 5/2004 |
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006210145 A1 | 8/2006 |
| AU | 2006210145 B2 | 8/2006 |
| AU | 2009207796 A1 | 7/2009 |
| AU | 2009243681 A1 | 11/2009 |
| AU | 2006311116 B2 | 1/2013 |
| BR | PI0413318 A | 10/2006 |
| BR | PI0413361 A | 10/2006 |
| BR | PI0513300 A | 5/2008 |
| BR | PI0606145 A2 | 2/2009 |
| CA | 722109 A | 11/1965 |
| CA | 2577233 A1 | 10/1997 |
| CA | 2650637 A1 | 10/1997 |
| CA | 2229621 A1 | 3/1998 |
| CA | 2317747 A1 | 7/1999 |
| CA | 2343234 A1 | 3/2000 |
| CA | 2352874 | 6/2000 |
| CA | 2414349 A1 | 1/2002 |
| CA | 2082573 C | 7/2002 |
| CA | 2456322 A1 | 2/2003 |
| CA | 2502965 | 5/2004 |
| CA | 2503155 A1 | 5/2004 |
| CA | 2534925 A1 | 2/2005 |
| CA | 2534932 A1 | 2/2005 |
| CA | 2489855 A1 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |
| CN | 1473562 A | 2/2004 |
| CN | 1980643 A | 4/2005 |
| CN | 101010071 A | 6/2005 |
| CN | 1671475 A | 9/2005 |
| CN | 101022787 A | 1/2006 |
| CN | 001863513 A | 11/2006 |
| CN | 001863514 A | 11/2006 |
| CN | 01917862 A | 2/2007 |
| CN | 1942174 A | 4/2007 |
| CN | 101011395 A | 8/2007 |

(56) References Cited

FOREIGN PATENT DOCUMENTS

| | | | |
|---|---|---|---|
| CN | 101027044 A | 8/2007 |
| CN | 101057849 A | 10/2007 |
| CN | 101484135 A | 11/2007 |
| CN | 101091721 A | 12/2007 |
| CN | 101111232 A | 1/2008 |
| CN | 101175482 A | 2/2008 |
| CN | 101370485 A | 2/2009 |
| CN | 101394839 A | 3/2009 |
| CN | 101652128 A | 2/2010 |
| DE | 2530563 | 1/1977 |
| DE | 4229085 A1 | 3/1994 |
| DE | 4309528 | 9/1994 |
| DE | 4446470 A1 | 6/1996 |
| DE | 69400215 | 10/1996 |
| DE | 19522899 C1 | 12/1996 |
| DE | 2808505 A1 | 1/1997 |
| DE | 19753534 | 6/1999 |
| DE | 19800689 C1 | 7/1999 |
| DE | 19800698 | 7/1999 |
| DE | 19822979 | 12/1999 |
| DE | 69229881 T2 | 12/1999 |
| DE | 19855440 | 6/2000 |
| DE | 19856147 A1 | 6/2000 |
| DE | 19940740 A1 | 3/2001 |
| DE | 19960494 | 6/2001 |
| DE | 10036400 | 6/2002 |
| DE | 69429710 | 8/2002 |
| DE | 10250083 | 12/2003 |
| DE | 10250084 | 5/2004 |
| DE | 10250087 A1 | 5/2004 |
| DE | 10250088 A1 | 5/2004 |
| DE | 10336400 | 3/2005 |
| DE | 10361596 | 9/2005 |
| DE | 102004019916 A1 | 11/2005 |
| DE | 102004020220 A1 | 11/2005 |
| DE | 10 2004 032049 A1 | 1/2006 |
| DE | 10 2004 032051 A1 | 1/2006 |
| DE | 10 2004 032103 A1 | 1/2006 |
| DE | 10 2005 005449 A1 | 8/2006 |
| DE | 102005005446 A1 | 8/2006 |
| DE | 102007011485 A1 | 9/2008 |
| DK | 1658055 T3 | 7/2007 |
| DK | 1658054 T3 | 10/2007 |
| DK | 1515702 T3 | 1/2009 |
| EC | SP066345 A | 8/2006 |
| EP | 0008131 A1 | 2/1980 |
| EP | 0216453 B1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A2 | 6/1987 |
| EP | 0 229 652 A2 | 7/1987 |
| EP | 0228417 A1 | 7/1987 |
| EP | 0229652 A2 | 7/1987 |
| EP | 0232877 A2 | 8/1987 |
| EP | 0239973 A2 | 10/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0328775 A1 | 8/1989 |
| EP | 0228417 B1 | 9/1990 |
| EP | 0229652 B1 | 10/1991 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0636370 A1 | 2/1995 |
| EP | 0641195 A1 | 3/1995 |
| EP | 0647448 A1 | 4/1995 |
| EP | 0654263 A1 | 5/1995 |
| EP | 0661045 A1 | 7/1995 |
| EP | 0675710 A1 | 10/1995 |
| EP | 0682945 A2 | 11/1995 |
| EP | 0693475 | 1/1996 |
| EP | 0820693 A1 | 1/1996 |
| EP | 0696598 A1 | 2/1996 |
| EP | 0583726 B1 | 11/1996 |
| EP | 0756480 A1 | 2/1997 |
| EP | 0760654 A1 | 3/1997 |
| EP | 0780369 | 6/1997 |
| EP | 0785775 A1 | 7/1997 |
| EP | 0761211 | 12/1997 |
| EP | 0809488 A1 | 12/1997 |
| EP | 0820698 | 1/1998 |
| EP | 0820753 A2 | 1/1998 |
| EP | 0857062 A2 | 8/1998 |
| EP | 0864324 A1 | 9/1998 |
| EP | 0864326 A2 | 9/1998 |
| EP | 0598606 B1 | 6/1999 |
| EP | 0675710 B1 | 8/1999 |
| EP | 0980894 | 2/2000 |
| EP | 0988106 A1 | 3/2000 |
| EP | 1014941 A1 | 7/2000 |
| EP | 1070504 A1 | 1/2001 |
| EP | 1127871 A1 | 8/2001 |
| EP | 1138321 A2 | 10/2001 |
| EP | 1152026 A1 | 11/2001 |
| EP | 1138321 A3 | 1/2002 |
| EP | 1166776 A2 | 1/2002 |
| EP | 1201233 A1 | 5/2002 |
| EP | 0661045 B1 | 7/2002 |
| EP | 1250045 | 10/2002 |
| EP | 1250045 A2 | 10/2002 |
| EP | 1251120 A1 | 10/2002 |
| EP | 1293127 | 3/2003 |
| EP | 1293195 A1 | 3/2003 |
| EP | 1293196 A2 | 3/2003 |
| EP | 1127871 B1 | 9/2003 |
| EP | 1201233 B1 | 12/2004 |
| EP | 1251120 B1 | 12/2004 |
| EP | 1492506 B1 | 1/2005 |
| EP | 1166776 B1 | 2/2005 |
| EP | 1502592 A1 | 2/2005 |
| EP | 1658054 A1 | 2/2005 |
| EP | 1658055 A1 | 2/2005 |
| EP | 1515702 B1 | 3/2005 |
| EP | 1527775 A1 | 4/2005 |
| EP | 1558221 A1 | 8/2005 |
| EP | 1558257 A1 | 8/2005 |
| EP | 1560585 A1 | 8/2005 |
| EP | 1611880 A2 | 1/2006 |
| EP | 1658054 B1 | 5/2006 |
| EP | 1138321 B1 | 1/2007 |
| EP | 1740161 A2 | 1/2007 |
| EP | 1658055 B1 | 3/2007 |
| EP | 1765303 A1 | 3/2007 |
| EP | 1786403 A1 | 5/2007 |
| EP | 1558221 B1 | 6/2007 |
| EP | 1842533 A2 | 10/2007 |
| EP | 1845955 A1 | 10/2007 |
| EP | 1845956 A1 | 10/2007 |
| EP | 1859789 A1 | 11/2007 |
| EP | 1980245 A1 | 10/2008 |
| EP | 1897545 A1 | 12/2008 |
| EP | 2131830 A2 | 12/2009 |
| EP | 2246063 A1 | 11/2010 |
| EP | 2249811 A1 | 11/2010 |
| EP | 2273983 A1 | 1/2011 |
| EP | 2402004 A2 | 1/2012 |
| ES | 2336571 T3 | 12/2004 |
| ES | 2260042 T3 | 11/2006 |
| ES | 2285497 T3 | 11/2007 |
| ES | 2288621 T3 | 1/2008 |
| ES | 2289542 T3 | 2/2008 |
| ES | 2315505 T3 | 4/2009 |
| GB | 1147210 A | 4/1969 |
| GB | 1567727 A | 5/1980 |

(56) References Cited

FOREIGN PATENT DOCUMENTS

| | | |
|---|---|---|
| GB | 2047095 A | 11/1980 |
| GB | 2057878 A | 4/1981 |
| GB | 2238478 A | 6/1991 |
| HR | P20070272 T3 | 6/2007 |
| HR | 20070456 T3 | 11/2007 |
| JP | S36-022895 | 11/1961 |
| JP | S55162714 A | 12/1980 |
| JP | S5659708 A | 5/1981 |
| JP | S56169622 A | 12/1981 |
| JP | S62240061 A | 10/1987 |
| JP | H0249719 A | 2/1990 |
| JP | 3 0501737 A | 4/1991 |
| JP | H0517566 A | 1/1993 |
| JP | H06507645 A | 9/1994 |
| JP | 08053331 A | 2/1996 |
| JP | 8 505076 A | 6/1996 |
| JP | H09508410 A | 8/1997 |
| JP | H1057450 A | 3/1998 |
| JP | H10251149 A | 9/1998 |
| JP | 2002524150 A | 8/2002 |
| JP | 2002 275175 A | 9/2002 |
| JP | 2003125706 A | 5/2003 |
| JP | 2003526598 A | 9/2003 |
| JP | 2005506965 A | 3/2005 |
| JP | 2005515152 A | 5/2005 |
| JP | 2005534664 | 11/2005 |
| JP | 2007501201 A | 1/2007 |
| JP | 2007501202 A | 1/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009523833 A | 6/2009 |
| JP | 2009531453 A | 9/2009 |
| JP | 2009537456 A | 10/2009 |
| JP | 2011504455 A | 2/2011 |
| JP | 2011506493 A | 3/2011 |
| JP | 2013536810 A | 9/2013 |
| JP | 2014505736 A | 3/2014 |
| JP | 2014528437 A | 10/2014 |
| KR | 1020060069832 A | 6/2006 |
| KR | 20070039041 A | 4/2007 |
| KR | 20070111510 A | 11/2007 |
| KR | 20090085312 A | 8/2009 |
| KR | 20100111303 A | 10/2010 |
| KR | 20110016921 A | 2/2011 |
| MX | 2007000008 A | 3/2007 |
| MX | 2007000009 A | 3/2007 |
| MX | 2007009393 A | 8/2007 |
| MX | 2010008138 | 8/2010 |
| MX | 2010012039 A | 11/2010 |
| NO | 20061054 | 3/2006 |
| NO | 20070578 A | 1/2007 |
| NO | 20074412 A | 11/2007 |
| NZ | 528302 A | 2/2007 |
| PT | 1699440 | 12/2004 |
| PT | 1658054 E | 5/2006 |
| PT | 1658055 E | 7/2007 |
| PT | 1515702 | 12/2008 |
| RU | 2131244 | 6/1999 |
| RU | 2198197 C2 | 2/2003 |
| RU | 2220715 C2 | 1/2004 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| RU | 256773 C2 | 11/2015 |
| SI | 1515702 T1 | 4/2009 |
| SI | 1699440 T1 | 11/2009 |
| SK | 10612003 A3 | 1/2004 |
| SU | 1759445 A1 | 9/1992 |
| TW | 1254634 B | 5/2006 |
| WO | 8000841 | 5/1980 |
| WO | 89/05624 A1 | 6/1989 |
| WO | 90/03776 | 4/1990 |
| WO | 93/06723 | 4/1993 |
| WO | 93/10758 | 6/1993 |
| WO | 93/11749 | 6/1993 |
| WO | WO 93/10765 A1 | 6/1993 |
| WO | 93/23017 A1 | 11/1993 |
| WO | 94/06414 | 3/1994 |
| WO | 94/08567 | 4/1994 |
| WO | 95/17174 | 6/1995 |
| WO | 95/20947 | 8/1995 |
| WO | 95/22319 | 8/1995 |
| WO | 95/30422 | 11/1995 |
| WO | 96/00066 | 1/1996 |
| WO | 96/03979 | 2/1996 |
| WO | 96/14058 | 5/1996 |
| WO | WO 1997/000673 A1 | 1/1997 |
| WO | 97/33566 | 9/1997 |
| WO | 9749384 | 12/1997 |
| WO | 9835655 A3 | 2/1998 |
| WO | 98/20073 A2 | 5/1998 |
| WO | 98/028698 | 7/1998 |
| WO | 98/35655 | 8/1998 |
| WO | WO 1998/051758 A1 | 11/1998 |
| WO | 99/012864 | 3/1999 |
| WO | 99/32120 | 7/1999 |
| WO | 99/44591 | 9/1999 |
| WO | 99/48481 A1 | 9/1999 |
| WO | WO 1999/045887 A2 | 9/1999 |
| WO | WO 2000/013647 A1 | 3/2000 |
| WO | 2000/033835 | 6/2000 |
| WO | 00/40205 A2 | 7/2000 |
| WO | 01/08661 A2 | 2/2001 |
| WO | 01/012230 | 2/2001 |
| WO | 01/15667 A1 | 3/2001 |
| WO | 01/52651 A2 | 7/2001 |
| WO | WO 2001/058451 A1 | 8/2001 |
| WO | 01/97783 A1 | 12/2001 |
| WO | 02/26061 | 4/2002 |
| WO | 02/26262 | 4/2002 |
| WO | 02/26928 | 4/2002 |
| WO | 0235991 A2 | 5/2002 |
| WO | WO 2002/071860 A1 | 9/2002 |
| WO | 02/088217 | 11/2002 |
| WO | WO 2002/094254 A2 | 11/2002 |
| WO | 03/006723 | 1/2003 |
| WO | WO 2003/006723 A1 | 1/2003 |
| WO | 03/013476 A1 | 2/2003 |
| WO | 03/013479 A1 | 2/2003 |
| WO | 03/015531 | 2/2003 |
| WO | WO 2003/013433 A2 | 2/2003 |
| WO | WO 2003/013538 A1 | 2/2003 |
| WO | 03/024430 A1 | 3/2003 |
| WO | 2003024426 A1 | 3/2003 |
| WO | WO 2003/018015 A1 | 3/2003 |
| WO | 03/026624 | 4/2003 |
| WO | 03/028698 | 4/2003 |
| WO | 03/028990 | 4/2003 |
| WO | 03/031546 A1 | 4/2003 |
| WO | 2003/026743 A2 | 4/2003 |
| WO | 03/035029 | 5/2003 |
| WO | 03/035053 A1 | 5/2003 |
| WO | 03/035054 A1 | 5/2003 |
| WO | 03/035177 | 5/2003 |
| WO | WO 2003/039561 A1 | 5/2003 |
| WO | WO 2003/049689 A2 | 6/2003 |
| WO | 03/053417 A2 | 7/2003 |
| WO | 03/068392 A1 | 8/2003 |
| WO | WO 2003/070191 A1 | 8/2003 |
| WO | 03/092648 | 11/2003 |
| WO | 03/094812 A1 | 11/2003 |
| WO | 03/105808 A1 | 12/2003 |
| WO | 04/004693 A1 | 1/2004 |
| WO | 2004/026262 | 4/2004 |
| WO | 2004/026263 | 4/2004 |
| WO | WO 2004/026280 A2 | 4/2004 |
| WO | 2004/037230 | 5/2004 |

(56) References Cited

FOREIGN PATENT DOCUMENTS

| | | |
|---|---|---|
| WO | 2004/037259 | 5/2004 |
| WO | 2004/037260 | 5/2004 |
| WO | 2004/043967 | 5/2004 |
| WO | 04/066910 | 8/2004 |
| WO | WO 2004/078212 A1 | 9/2004 |
| WO | 04/084869 | 10/2004 |
| WO | 04/093801 | 11/2004 |
| WO | 04/100894 | 11/2004 |
| WO | 2004/093819 | 11/2004 |
| WO | 2004 098567 A2 | 11/2004 |
| WO | 2005 016313 | 2/2005 |
| WO | 2005 063214 | 2/2005 |
| WO | 2005/102286 | 3/2005 |
| WO | 05/032524 | 4/2005 |
| WO | 2005/041968 | 5/2005 |
| WO | 05/055981 | 6/2005 |
| WO | 2005/053656 | 6/2005 |
| WO | 2005053587 A1 | 6/2005 |
| WO | 05/065646 | 7/2005 |
| WO | 2005/016314 | 7/2005 |
| WO | 2005/066183 | 7/2005 |
| WO | WO 2005/060942 A1 | 7/2005 |
| WO | 2005079760 A1 | 9/2005 |
| WO | 2005105036 A1 | 11/2005 |
| WO | WO 2005/102286 A1 | 11/2005 |
| WO | WO 2005/102294 A2 | 11/2005 |
| WO | 2006/002883 | 1/2006 |
| WO | 2006/002884 | 1/2006 |
| WO | 2006/002886 | 1/2006 |
| WO | WO 2006/002884 B1 | 3/2006 |
| WO | WO 2006/039692 A2 | 4/2006 |
| WO | 2005102294 A3 | 5/2006 |
| WO | 2006058249 A2 | 6/2006 |
| WO | 2006/082097 | 8/2006 |
| WO | 2006/082099 | 8/2006 |
| WO | WO 2006/105615 A1 | 10/2006 |
| WO | WO 2006/128471 A2 | 12/2006 |
| WO | 2007/005716 | 1/2007 |
| WO | 2007/008752 | 1/2007 |
| WO | WO 2007/014061 A2 | 2/2007 |
| WO | 2007/048233 | 5/2007 |
| WO | 2007/053698 | 5/2007 |
| WO | 2007/085024 | 7/2007 |
| WO | 200785024 A3 | 7/2007 |
| WO | WO 2007/085024 A3 | 7/2007 |
| WO | 2007/103286 A2 | 9/2007 |
| WO | 2007103105 A2 | 9/2007 |
| WO | 2009112273 A2 | 9/2007 |
| WO | 2007 112273 A2 | 10/2007 |
| WO | 2007/112285 | 10/2007 |
| WO | WO 2007/112286 A2 | 10/2007 |
| WO | WO 2007/131357 A1 | 11/2007 |
| WO | 2008 023261 A1 | 2/2008 |
| WO | 2008033523 A1 | 3/2008 |
| WO | WO 2008/069941 A2 | 6/2008 |
| WO | 2008/086804 | 7/2008 |
| WO | 2008/107149 | 9/2008 |
| WO | 2008107149 A3 | 9/2008 |
| WO | WO 2008/107149 A3 | 9/2008 |
| WO | WO 2008/109462 A2 | 9/2008 |
| WO | WO 2008/132707 A1 | 11/2008 |
| WO | WO 2008/142627 A2 | 11/2008 |
| WO | 2008/148798 | 12/2008 |
| WO | 2009/003776 A1 | 1/2009 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | 2009/092601 | 7/2009 |
| WO | 2009092601 A1 | 7/2009 |
| WO | WO 2009/110005 A2 | 9/2009 |
| WO | 2009135680 A1 | 11/2009 |
| WO | WO 2010/022193 A2 | 2/2010 |
| WO | WO 2010/044842 A1 | 4/2010 |
| WO | 2010057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/088911 A1 | 8/2010 |
| WO | WO 2010/105672 A1 | 9/2010 |
| WO | 2010140007 A2 | 12/2010 |
| WO | 20100140007 A9 | 12/2010 |
| WO | WO 2010/149169 A2 | 12/2010 |
| WO | 2011009602 A1 | 1/2011 |
| WO | 2011009603 A1 | 1/2011 |
| WO | 2011009604 A1 | 1/2011 |
| WO | WO 2011/008298 A2 | 1/2011 |
| WO | 2011 095314 A3 | 8/2011 |
| WO | WO 2011/095314 A2 | 8/2011 |
| WO | WO 2011/128630 A2 | 10/2011 |
| WO | WO 2011/154414 A1 | 12/2011 |
| WO | 2012 028317 A1 | 3/2012 |
| WO | 2012 028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A2 | 2/2013 |
| WO | WO 2013/017242 A1 | 2/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/167735 A1 | 11/2013 |
| WO | WO 2014/059512 A1 | 4/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/103379 A1 | 7/2015 |

OTHER PUBLICATIONS

K.H. Bauer, Lehrbuch der Pharmazeutischen Technologie, 6th edition, WVG Stuttgart, 1999.
Bioavailability and Bioequivalence—Studies for Orally Administered Drug Products—General Considerations, FDA, BP, Announced in the Federal Register: vol. 68, No. 53/Mar. 19, 2003.
P.A. Proeschel et al, J Dent Res, 2002, 81(7), 464-468.
H. Lockhart and F.A. Paine et al., Packaging Pharmaceutical and Healthcare Products, Springer, 1st ed, 1996.
Wu et al, J. Control Release, Feb. 16, 2005; 102(3): 569-81.
Crowley MM,Drug Dev Ind Pharm. Sep. 2007;33(9):909-26.
Repka MA,Drug Dev Ind Pharm. Oct. 2007;33(10):1043-57.
Encyclopedia of Pharmaceutical Technology, Third Edition, vol. 6, edited by James Swarbrick PharmaceuTech, Inc., Pinehurst, North Carolinia, USA.
Encyclopedia of Pharmaceutical Technology, Third Edition, vol. 5, edited by James Swarbrick PharmaceuTech, Inc., Pinehurst, North Carolinia, USA.
Encyclopedia of Pharmaceutical Technology, Third Edition, vol. 4, edited by James Swarbrick PharmaceuTech, Inc., Pinehurst, North Carolinia, USA.
Encyclopedia of Pharmaceutical Technology, Third Edition, vol. 3 edited by James Swarbrick PharmaceuTech, Inc., Pinehurst, North Carolinia, USA.
Encyclopedia of Pharmaceutical Technology, Third Edition, vol. 2, edited by James Swarbrick PharmaceuTech, Inc., Pinehurst, North Carolinia, USA.

(56) References Cited

OTHER PUBLICATIONS

Encyclopedia of Pharmaceutical Technology, Third Edition, vol. 1, edited by James Swarbrick PharmaceuTech, Inc., Pinehurst, North Carolinia, USA.
Pharmaceutical Dosage Forms, Tablets, Second Edition, Revised and Expanded, Edited by Herbert A. Lieberman, 1990.
Y.-S. Lee et al., Principles of Terahertz Science and Technology (Lecture Notes in Physics), Springer; 1 edition 2008.
R.E. Miles et al., Terahertz Frequency Detection and Identification of Materials and Objects (NATO Science for Peace and Security Series B: Physics and Biophysics), Springer; 1 edition 2007.
Dexheimer, Terahertz Spectroscopy: Principles and Applications (Optical Science and Engineering Series), CRC; 1 edition 2007.
"Note for Guidance on the Investigation of Bioavailability and Bioequivalence", EMEA, London, Jul. 26, 2001 (CPMP/EWP/QWP/1401/98.
Guidance for Industry—Statistical Approaches to Establishing Bioequivalence, FDA, BP, Jan. 2001.
In Handbuch der Kunststoff-Extrusionstechnik I (1989) "Grundlagen" in Chapter 1.2 "Klassifizierung von Extrudern", pp. 4 to 6.
O.G. Piringer et al., Plastic Packaging: Interactions with Food and Pharmaceuticals, Wiley-VCH, 2nd ed.
D.A. Dean, Pharmaceutical Packaging Technology, Taylor & Francis, 1st ed.
Kurt H. Bauer, K. Lehmann, Hermann P. Osterwald, Rothgang, Gerhart, 1st edition, 1998, Medpharm Scientific Publishers.
International Search Report and Written Opinion dated Nov. 22, 2010.
João F. Pinto et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
European Search Report for related EP 12 00 2708.1-1219, dated Sep. 24, 2012.
Augustine, R.L., Catalytic Hydrogenation of a, B-Unsaturated Ketones. III The Effect of Quantity and Type of Catalysts, J.Org Chem. 28(1), pp. 152-155, Abstract 1963.
P. Cornish "Avoid the Crush": hazards of medication administration in patients with dysphagia or a feeding tube, CMA Media Inc., CMAJ. 172(7), pp. 871-872, 2005.
"The Dissolution Procedure: Development and Validation", heading "Study Design", "Time Points" US Pharmacopoeia (USP), General Chapter 1092, pp. 1-15, 2006.
European Search Report, Application No./Patent No. 11006253.6-2112, dated Dec. 16, 2011.
European Search Report, Application No./Patent No. 11006254.4-2112, dated Dec. 16, 2011.
European Search Report, Application No./Patent No. 11008131.2-1219, dated Feb. 24, 2012.
European Search Report, Application No./Patent No. 12001296.8-1219, dated Jun. 26, 2012.
European Search Report, Application No./Patent No. 11009129.5-2112, dated Apr. 10, 2012.
European Search Report, Application No./Patent No. 12001301.6-1219, dated Jun. 26, 2012.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
Goodman and Gilman, "The Pharmacological Basis of Therapeutics, Seventh Edition", MacMillan Publishing Company, Table of Contents. 1985.
Griffin, "Classification of Surface-Active Agents by HLB" Journal of the Society of Cosmetic Chemists, Atlas Powder Company, 1949, pp. 311-326.
Griffith et al. "Tablet Crushing and the Law: The Implications for Nursing" Professional Nurse 19(1), pp. 41-42, 2003.
A. James, "The legal and clinical implications of crushing tablet medication", Nurse Times 100(50), 28-33, 2004.
McGinity et al., Hot-Melt Extrusion as a Pharmaceutical Process, American Pharmaceutical Review, vol. 4 (2), pp. 25-36, 2001.

C. W. McGary, Jr. "Degradation of Poly(ethylene Oxide)", Journal of Polymer Science vol. XLVI, 1960, pp. 51-57.
Mitchell, "Oral Dosage Forms That Should Not Be Crushed: 2000 Update" Hospital Pharmacy 35(5), 553-557, 2000.
Munjal et al."Polymeric Systems for Amorphous Delta9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Ozeki et al. "Control of Medicine Release From Solid Dispersion Through Poly(ethylene oxide)-Carboxyvinylpolymer Interaction", International Journal of Pharmaceutics, 165, 1998, pp. 239-244.
Ozeki et al. "Controlled Release From Solid Dispersion Composed of Poly(ethylene oxide)-Carbopol Interpolymer Complex With Various Cross-Linking Degrees of Carbopol", Journal of Controlled Release. 63, 2000. pp. 287-295.
Schier et al. "Fatality from Administration of Labetalol and Crushed Extended-Release Nifedipine" The Annals of Pharmacotherapy vol. 37, 1420-1423, Oct. 2003.
Weiss, U., "Derivatives of Morphine. I 14-Dihydroxydihydromorphinone," J. Am. Chem. Soc. 77, pp. 5891-5892, Nov. 20, 1955.
Wade and Weller, "Handbook of Pharmaceutical Excipients: 2nd Edition", The American Pharmaceutical Association and The Pharmaceutical Press, Table of Contents pp. v-vi, 1994.
Henrist et al. In vitro and in vivo evaluation of starch-based hot stage extruded double matrix systems. Journal of Controlled Release. 2001, vol. 75, pp. 391-400.
McNeill et al. Properties controlling the diffusion and release of water-soluble solutes from poly(ethylene oxide) hydrogels. 4. Extended constant rate release from partly-coated spheres. Journal Biomat. Sci. Polynn. Ed. 1996, vol. 7, pp. 953-963.
Pillay et al. A novel approach for constant rate delivery of highly soluble bioactives from a simple monolithic system. Journal of Controlled Release. 2000, vol. 67, pp. 67-78.
European Search Report, Application No./Patent No. 12003743.7-1219, dated Sep. 24, 2012.
Evonik Industries. Eudragit Application Guidelines. 10th Edition, 2008. Table of Contents.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Dachille et al., "High-pressure Phase Transofromations in Laboratory Mechanical Mixers and Mortars", Nature, vol. 186, Apr. 2, 1960, pp. 34 and 71.
Liu et al., "Properties of Lipophilic Matrix Tables Containing Phenylpropanolamine Hydrochloride Prepared by Hot-Melt Extrusion", European Journal of Pharmaceutics and Biopharmaceutics, 52 (2001), pp. 181-190.
Repka et al., Bioadhesive Properties of Hydroxypropylcellulose Topical Films Produced by Hot-Melt Extrusion, Journal of Controlled Release, 70 (2001), pp. 341-351.
English translation of Chinese Office Action for related Chinese Application No. 2009801550627 dated Oct. 8, 2012.
C.J. Deighan et al., Rhabdomyolysis and acute renal failure resulting from alcohol and drug abuse, Q.J. Med, vol. 93, 2000, pp. 29-33.
Sax et al,Hawley's Condensed Chemical Dictionary, Lewis, Sr. ed. 13th ed. 1997, p. 1178.
Kalant et al., Death in Amphetamine Users: Causes and Rates, CMA Journal, vol. 112, Feb. 8, 1975 pp. 299-304.
K.R. Woodburn et al., Vascular complications of injecting drug misuse, Br. J. of Surgery, vol. 83, 1996, pp. 1329-1334.
Riipi et al., The effect of compression force on surface structure, crushing strength, friability and disintegration time of erythromycin acistrate tablets, Eur J Pharm Biopharm, vol. 46, 1998, pp. 339-345.
Dow Chemical Company, Using Methocel Cellulose Ethers for Controlled Release of Drugs in Hydrophilic Matrix Systems, 2000, p. 10.
"Note for Guidance on Stability Testing," EMEA, Aug. 2003, pp. 1-20.

(56) References Cited

OTHER PUBLICATIONS 2.9 Methoden der pharmazeutischen Technologie 143-144, 1997.
Apicella A., Biomaterials, vol. 14, No. 2, pp. 83-90, 1993.
Arnold, "Teen Abuse of Painkiller OxyContin on the Rise," www.npr.org, Dec. 19, 2005.
Bailey F.E., et al., "Some properties of poly(ethylene oxide)' in aqueous solution," Journal of Applied Polymer Science, vol. 1, Issue No. 1, pp. 56-62, 1959.
Bauer, Coated Pharmaceutical Dosage Forms, CRC Press, 1998, 1-10.
Baum et al., The Impact of the Addition of Naloxone on the Use and Abuse of Pentazocine. Public Health Reports, 102(4): 426-429 (1987).
Braun, et al. A study of bite force, part 2: Relationship to various cephalometric measurements. Angle Orthodontist, vol. 65 (5) pp. 373-377, 1995.
Caraballo et al., Percolation thresholds in ultrasound compacted tablets. Journal of Controlled Release, vol. 69, pp. 345-355, 2000.
Coppens et al., "Hypromellose, Ethylcellulose, and Polyethylene Oxide Use in Hot Melt Extrusion"; Pharmaceutical Technology, 62-70, Jan. 2005.
Crowley M.M. et al., Pharmaceutical applica6tions of hot-melt extrusion, Biomaterials 23, 2002, pp. 4241-4248.
Dachille, F. et al., "High-Pressure Phase Transformation in Laboratory Mechanical Mixers and Mortars", 1960., Nature, 186, pp. 1-2 (abstract).
Davies, et al; The determination of the mechanical strength of tablets of different shapes. European Journal of Pharmaceutics and Biopharmaceutics, 67, 2007, pp. 268-276.
Dejong. Relations between tablet properties. Pharmaceutisch Weekblad Scientific Edition 1987, p. 24-28.
Dow Excipients Chem. of Poly. Water Soluble-Resin 2004.
DOW Technical Data, POLYOX, Feb. 2003.
Efentakis M. et al. Evaluation of high molecular weight poly(oxyethylene) (Polyox) polymer: studies of flow properties and release rates of furosemide and captopril from controlled-release hard gelatin capsules. Pharmaceutical Development and Technology, 5 (3), pp. 339-346, 2000.
El-Sherbiny et al., Preparation, characterization, swelling and in vitro drug release behaviour of poly[N-acryloylglycine-chitosan] interpolymeric pH and thermally-responsive hydrogels. European Polymer Journal, vol. 41, pp. 2584-2591, 2005.
Adel El-Egakey et al, Hot extruded dosage forms, part 1. Pharmacerutica Acta Helvetiae, vol. 46, pp. 31-53,Mar. 19, 1970.
Committee for Proprietary Medicinal Products. Note for Guidance on the Investigation of Bioavailability and Bioequivalence. 2001. pp. 1-18.
Fell, et al, Determination of tablet strength by diametral-compression test. Journal of Pharmaceutical Sciences, vol. 59, No. 5, May 1970, pp. 688-691.
Follonier N. et al. Evaluation of Hot melt extrusion as a new technique for the production of polymer-based pellets for sustained release capsules containing high loadings of freely soluble drugs. Drug Development and Industrial Pharmacy, 20(8), pp. 1323-1339, 1994.
Follonier N. et al., Various ways of modulating the release of diltiazem hydrochloride from hot-melt extruded sustained release pellets prepared using polymeric materials. Journal of Controlled Release 36, pp. 243-250, 1995.
Freed et al., "pH Control of Nucleophilic/electrophilic oxidation", International Journal of Pharmaceutics, vol. 357, pp. 180-88 (2008).
Graham N. B., Poly(Ethylene Glycol) Gels and Drug Delivery. Poly(Ethylene Glycol) Chemistry: Biotechnical and Biomedical Applications, Chapter 17, 1992.
Griffith, Table crushing and the law: the implications for nursing. Drug Administration, vol. 19, No. 1, pp. 41-42, 2003.
Hanning C.D. et al., Morphine hydrogel suppository. British Journal of Anaesthesia, 61, pp. 221-227, 1988.
Inert gas—Wikipedia, Dec. 2009.

Janicki S. et al. Slow release microballs: Method of Preparation. Acta Pharm. Technol. 33 (3) 154-155, 1987.
Katz et al., Challenges in the Development of Prescription Opioid Abuse-deterrent Formulations. Clin. J. Pain, 23(8): 648-660 (2007).
Kim C.-J. Drug release from compressed hydrophilic POLYOX-WSR tablets. J Pharm. Sciences 1995, 84(3): pp. 303-306.
Kim et al., Preparation and evaluation of eudragit gels. V. Rectal gel preparations for sustained release and avoidance of first-pass metabolism of lidocaine. Chem. Pharm Bull. 1992, 40(10), 2800-2804.
J.W. McGinity—Letter of Jan. 26, 2009.
Dr. Rick Matos, Ph.D—Letter Jan. 6, 2011.
Levina et al., The effect of ultrasonic vibration on the compaction characteristics of ibuprofen. Drug Development and Industrial Pharmacy, vol. 28, No. 5, pp. 495-514, 2002.
Levina, The effect of ultrasonic vibration on the compaction characteristics of paracetamol. Journal of Pharmaceutical Sciences, vol. 89, No. 6, pp. 705-723, Jun. 2000.
Madorsky S.L., Thermal degradation of polyethylene oxide and polypropylene oxide. Journal of Polymer Science, vol. 36, No. 3, Mar. 1959.
Maggi. Therapeutic Potential of Capsaicin-like Molecules. Life Sciences, vol. 51, pp. 1777-1781, 1992.
Maggi et al., Dissolution behaviour of hydrophilic matrix tablets containing two different polyethylene oxides (PEOs) for the controlled release of a water-soluble drug. Dimensionality study. Biomaterials, 2002, 23, 1113-1119.
Maggi L.et al, "High molecular weight polyethylene oxides (PEOs) as an alternative to HPMC in controlled release dosage form", 2000, International Journal of Pharmaceutics, 195 pp. 229-238.
Mank R., Darstellung wirkstoffhaltiger Extrusionsformlinge auf der Basis von Thermoplasten. Pharmazie 44, H. 11, pp. 773-776, 1989.
Mank R., Darstellung wirkstoffhaltiger Extrusionsformlinge auf der Basis von Thermoplasten. Pharmazie 45, H. 8, pp. 592-593 1990.
Mesiha M.S., A screening study of lubricants in wet powder masses suitable for extrusion-spheronization. Drug Development and Industrial Pharmacy, 19(8), pp. 943-959, 1993.
Miller, To crush or not to crush. Nursing, pp. 50-52, Feb. 2000.
Mitchell, Oral dosage forms that should not be crushed: 2000 update. Special Resource, vol. 35, No. 5, pp. 553-567, 2000.
Moroni A., Application of poly(oxyethylene) homopolymers in sustained release solid formulations. Drug Development and Industrial Pharmacy, 21(12) pp. 1411-1428, 1995.
Ohnishi N. et al., Effect of the molecular weight of polyethylene glycol on the bioavailability of indomethacin sustained-release suppositories prepared with solid dispersions. Chem. Pharm. Bull, 35(8), pp. 3511-3515, 1987.
Ozeki T. et al., Control of medicine release from solid dispersion composed of the poly(ethylene oxide)-carboxyvinylpolymer interpolymer complex by varying molecular weight of poly(ethylene oxide). Journal of Controlled Release 58, pp. 87-95, 1999.
Purdue News, "Purdue Pharma Provides Update on Development of New Abuse-Resistant Pain Medications; FDA Cites Patient Needs As First Priority; New Drug Application Delayed," www.headaches.about.com, Jun. 18, 2002.
Pharmazeutische Biologie—Drogen und ihre Inhaltsstoffe—Scharfstoffdrogen, pp. 82-92, 1982 (WAGNER).
Pharm. Research, Official Journal of the American Association of Pharmaceutical Scientists, Sep. 1989, 6(9), S-98.
Pharm. Research, Official Journal of the American Association of Pharmaceutical Scientists, Oct. 1991, 8(10), S-192.
Prapaitrakul W., Release of chlorpheniramine maleate from fatty acid ester matrix disks prepared by melt-extrusion. J. Pharm. Pharmacol. 43, pp. 377-381, 1991.
Radko S., Molecular sieving by polymer solutions: dependence on particle and polymer size, independence of polymer entanglement. Applied ad Theoretical Electrophoresis 5, pp. 79-88, 1995.
Remington's Pharmaceutical Sciences, pp. 1553-1593, Ch. 89, 1980, 16th Edition.
Remington's Pharmaceutical Sciences 17th ed., 1418 (1985).
Rippie E.G., Regulation of dissolution rate by pellet geometry. Journal of Pharmaceutical Sciences, Vo. 58, No. 4, pp. 428-431, Apr. 1969.

(56) References Cited

OTHER PUBLICATIONS

Scheirs J., "Characterizing the Solid-State Thermal Oxidation of Poly (ethylene oxide) Powder", Polymer, vol. 32, No. 11, 1991.
Schroeder J.,Granulierung hydrophober Wirkstoffe im Planetwalzenextruder 2003, vol. 65, No. 4, 367-372.
Shivanand P. Factors affecting release of KCI from melt extruded polyethylene disks. Pharmaceutical Research, Oct. 1991, vol. 8, No. 10, p. S-192.
Sprockel O.L., Permeability of cellulose polymers: water vapour transmission rates. J. Pharma. Pharmacol. 42, pp. 152-157, 1990.
Stafford J., überzogene feste Formen, 1991, 347-68.
Strang, Abuse of Burprenorphine (Temgesic) by snorting, British Med. J., 302: 969 (1991).
Stringer J.L., Diffusion of small molecular weight drugs in radiation-crosslinked poly(ethylene oxide) hydrogels. Journal of Controlled Release 42, pp. 195-202, 1996.
Summers et al; Influence of crystal form on tensile strength of compacts of pharmaceutical materials. Journal of Pharmaceutical Sciences, vol. 66, No. 8, Aug. 1977, pp. 1172-1175.
Tablet, www.docstoc.com (2011).
Third Party Observations, Feb. 2, 2009.
Thoma V.K. et al. "Bestimmung der In-vitro-Freigabe von schwach basischen Wirkstoffen aus Ratardarzneiformen", Pharm. Ind. 51, Nr. 3, 1989.
Tipler, et al, Physics for Scientists and Engineers, 6th Edition, pp. 234-235, 2003.
Tompkins et al., Human abuse liability assessment of oxycodone combined with ultra-low-dose naltrexone. Psychopharma., 210: 471-480 (2010).
US Pharmacopoeia, Chapter 1217, Aug. 1, 2008.
Waltimo, et al, "A novel bite force recorder and maximal isometric bite force values for healthy young adults", Scandinavian Journal of Dental Research 1993; 101: 171-175.
Waltimo, et al, "Maximal bite force and its association with signs and symptoms of craniomandibular disorders in young Finnish non-patients", ACTA Odontol Scand 53 (1995) : 254-258.
Waterman et al., "Stabilization of Pharmaceuticals to Oxidative Degredation", Pharmaceutical Development and Technology, vol. 71(1), pp. 1-32, (2002).
Waters et al., Intravenous Quetiapine-Cocaine Use ("Q-Ball"). Am. J. Psychiatry, 164(1): pp. 173-174 (2007).
Yang, et al; "Characterization of Compressibility and Compactibility of Poly(ethylene oxide) Polymers for Modified Release Application by Compaction Simulator"; Journal of Pharmaceutical Sciences, vol. 85, No. 10, Oct. 1996.
Yarbrough et al, Letters to Nature 322, 347-349 (Jul. 24, 1986) "Extraordinary effects of mortar-and-pestle grinding on microstructure of sintered alumina gel".
Zhang et al., Pharmaceutical Development and Technology, 1999, 4, 241-250.
Rowe et al. Handbook of Pharmaceutical Excipients. Sixth Edition. 2009, pp. v-ix, Table of Contents.
Herbert A. Lieberman, Pharmaceutical Dosage Forms, Tablets, Second Edition, Revised and Expanded, 1990.
Brown, "The Dissolution Procedure: Development and Validation" vol. 31(5). Chapter 1092, 2006, pp. 1-15.
Bauer et al. Lehrbuch der Pharmazeutischen Technologie. 1999. pp. IX-XV, Table of contents.
European Pharmacopoeia, Third Edition, Council of Europe, Strasbourg, 1997, pp. 127-152.
European Pharmacopoeia, Third Edition Supplement 2000, Council of Europe, Strasbourg, 2000, pp. 85-107.
Hong et al. Dissolution kinetics and physical characterization of three-layered tablet with poly(ethylene oxide) core matrix capped by Carbopol. Int .J. Pharmacol. 2008, vol. 356, pp. 121-129.
Hoepfner et al. Fiedler Encyclopedia of Excipients. 2007, Table of Contents only.
Cawello, "Parameters for Compartment-free Pharmacokinetics—Standardization of Study Design, Data Analysis and Reporting" 1999, pp. XI-XIII (table of contents).
Ravin, Louis. Preformulation. Chapter 76. In Remington's Pharmaceutical Sciences, 17th Ed, 1985.
Disanto, Anthony. Bioavailability and Bioequivalency Testing. Chapter 77. In Remington's Pharmaceutical Sciences, 17th Ed, 1985.
Knevel, Adelbert. Separation. Chapter 78. In Remington's Pharmaceutical Sciences, 17th Ed, 1985.
Phillips, G. Briggs. Sterilization. Chapter 79. In Remington's Pharmaceutical Sciences, 17th Ed, 1985.
Siegel, Frederick. Tonicity, Osmoticity, Osmolality, and Osmolarity. Chapter 80. In Remington's Pharmaceutical Sciences, 17th Ed, 1985.
Giles et al. Plastic Packaging Materials. Chapter 81. In Remington's Pharmaceutical Sciences, 17th Ed, 1985.
Lintner, Carl. Stability of Pharmaceutical Products. Chapter 82. In Remington's Pharmaceutical Sciences, 17th Ed, 1985.
Erskine, Jr., Clyde. Quality Assurance and Control. Chapter 83. In Remington's Pharmaceutical Sciences, 17th Ed, 1985.
Nairn, J.G., Solutions, Emulsion, Suspensions and Extractives. Chapter 84. In Remington's Pharmaceutical Sciences, 17th Ed, 1985.
Avis, Kenneth. Parenteral Preparations. Chapter 85. In Remington's Pharmaceutical Sciences, 17th Ed, 1985.
Turco et al. Intravenous Admixtures. Chapter 86. In Remington's Pharmaceutical Sciences, 17th Ed, 1985.
Mullins, John. Ophthalmic Preparations. Chapter 87. In Remington's Pharmaceutical Sciences, 17th Ed, 1985.
Block, Lawrence. Medicated Applications. Chapter 88. In Remington's Pharmaceutical Sciences, 17th Ed, 1985.
Rippie, Edward. Powders. Chapter 89. In Remington's Pharmaceutical Sciences, 17th Ed, 1985.
King et al. Oral Solid Dosage Forms. Chapter 90. In Remington's Pharmaceutical Sciences, 17th Ed, 1985.
Porter, Stuart. Coating of Pharmaceutical Dosage Forms. Chapter 91. In Remington's Pharmaceutical Sciences, 17th Ed, 1985.
Longer et al. Sustained-Release Drug Delivery Systems. Chapter 92. In Remington's Pharmaceutical Sciences, 17th Ed, 1985.
Sciarra et al. Aerosols. Chapter 93. In Remington's Pharmaceutical Sciences, 17th Ed, 1985.
Repka, Pharmaceutical applications of hot-melt extrusion MA,Drug Dev Ind Pharm. Oct. 2007;33(10): 1043-57. (Abstract).
Yeh et al., Stability of Morphine in Aqueous Solution III: Kinetics of Morphine Degradation in Aqueous Solution, Wiley Subscription Services, Inc., Journal of Pharmaceutical Sciences, 50(1): 35-42 (1961).
Albertini, B. "New spray congealing atomizer for the microencapsulation of highly concentrated solid and liquid substances" European Journal of Pharmaceutics and Biopharmaceutics 69 (2008) 348-357.
Alekseeva et al, Chemical-Pharmaceutical Journal, vol. 41, No. 9, 2007, 49-52. (Full translation attached.).
Almeida, A. et al., Ethylene vinyl acetate as matrix for oral sustained release dosage forms produced via hot-melt extrusion, European Journal of Pharmaceutics and Biopharmaceutics 77 (2011) 297-305.
Almeida, A. et al., Sustained release from hot-melt extruded matrices based on ethylene vinyl acetate and polyethylene oxide, European Journal of Pharmaceutics and Biopharmaceutics 82 (2012) 526-533.
Application of a modelling system in the formulation of extended release hydrophilic matrices, Reprinted from Pharmaceutical Technology Europe, Jul. 2006.
Application of Opadry II, complete film coating system, on metformin HCI extended release matrices containing Polyox water soluble resin, Colorcon Apr. 2009.
Bauer et al. Lehrbuch der Pharmazeutischen Technologie. Eight Edition 2006. Stuttgart, pp. 343-352.
Baxter, J.L. et al., "Hydrodynamics-induced variability in the USP apparatus II dissolution test," International Journal of Pharmaceutics 292 (2005) 17-28.
Bellmann et al., "Development of an advanced in vitro model of the stomach and its evaluation versus human gastric psychology." Food Research International 88 (2016) 191-198.
Bingwen et al, 2008, p. 367. (full translation attached).

(56) References Cited

OTHER PUBLICATIONS

Borquist et al., "Simulation of the release from a multiparticulate system validated by single pellet and dose release experiements," J. Controlled Release, 97: 453-465 (2004).
Bruce et al, Properties of hot-melt extuded tablet formulations for the colonic delivery of 5-aminosalicylic acid, European Journal of Pharmaceutics and Biopharmaceutics, 59 (2005) 85-97.
Carbopol 71G, retrieved Mar. 10, 2014 from http://www.lubrizol.com/LifeScience/Products/Carbopol71G-NF.html.
Chibuzor et al. "Formulation Development and Evaluation of Drug Release Kinetics from Colon-Targeted Ibuprofen Tablets Based on Eudragit RL 100-Chitosan Interpolyelectrolyte Complexes," Hindawi Publ. Corporation ISRN Pharmaceutics, vol. 2013, Article ID 838403.
Costa et al. "Modeling and comparison of dissolution profiles"; European Journal of Pharmaceutical Sciences 13 (2001) 123-33.
Cuesov, Drug Production Technology, Kharkov, 1999, pp. 351-352. (Full translation attached.).
Deighan, C.J. et al., Rhabdomyolysis and acute renal failure resulting from alcohol and drug abuse, Q.J. Med, vol. 93, 2000, pp. 29-33.
Dierickx et al., "Co-extrusion as manufacturing technique for fixed-dose combination mini-matrices," European Journal of Pharmaceutics and Biopharmaceutics 81 (2012), 683-689.
Dow Chemical Company, "Using Dow Excipients for Controlled Release of Drugs in Hydrophilic Matrix Systems", Sep. 2006, pp. 1-36.
Efentakis et al, Effects of Excipients on Swelling and Drug Release from Compressed Matrices, in Drug Development and Industrial Pharmacy 23(1):107-112, Jan. 1997, Abstract.
Eggleston, "The seat of the emetic action of various drugs," J. Pharmacol. Exp. Ther. 7, 225-253 (1915).
Encyclopedia of Pharmacological Technology, Informa Healthcare, 1st Ed., 1996, vol. 14 (Table of Content only).
Eudragit NE40D web page from Evonik website; downloaded Feb. 24, 2015.
Eudragit RS PO web page from Evonik website; downloaded Feb. 24, 2015.
European Pharmacopeia 5.0; Glyceryl behenate monograph; dated Jan. 2005; downloaded Feb. 24, 2015.
European Search Report and Opinion Application No. 14176277.3-1460, dated Dec. 15, 2014.
European Search Report and Written Opinion for EP Application No. 13169658.5, dated Aug. 6, 2013.
European Search Report and Written Opinion for EP Application No. 13169659.3, dated Aug. 6, 2013.
European Search Report and Written Opinion for EP Application No. 13176309.9-1460, dated Oct. 9, 2013.
European Search Report and Written Opinion for EP Application No. 13197503.9-1460, dated Feb. 18, 2014.
European Search Report and Written Opinion for EP Application No. 13425151.1-1460, dated Mar. 11, 2014.
European Search Report and Written Opinion for EP Application No. 14169801.9-1455 dated Oct. 20, 2014.
Evaluation of Verapamil HCl (240 mg) Extended Release Matrix Formulation Using USP Apparatus III in Biorelevant Dissolution Media, Jul. 2009.
Evonik Rohm GmbH product brochure: EUDRAGIT acrylic polymers for solid oral dosage forms (2009).
Extended European Search Report for Application No. EP 16183922.0-1460, dated Oct. 31, 2016.
Extended European Search Report and Opinion for Application No. EP 15153679.4-1455, dated Jun. 30, 2015.
Extended European Search Report and Opinion for Application No. EP 15165064.5-1455, dated Oct. 16, 2015.
Extended European Search Report and Opinion for Application No. EP 15165065.2-1455, dated Nov. 2, 2015.
Extended European Search Report and Opinion for Application No. EP 15165067.8-1455, dated Nov. 2, 2015.
Extended European Search Report and Opinion for Application No. EP 15165069.4-1455, dated Nov. 2, 2015.
Extended European Search Report and Opinion for Application No. EP 15165070.2-1455, dated Nov. 2, 2015.
Extended European Search Report and Opinion for Application No. EP 15184634.2-1455, dated Mar. 3, 2016.
Fathima, N. et al. "Drug-excipient interaction and its importance in dosage form development," Journal of Applied Pharmaceutical Science 01 (06); 2011, pp. 66-71.
Formulation of Polyox ER Matrices for a Highly Soluble Active, Colorcon Jul. 2009.
Foye, W., Principles of Medicinal Chemistry; Analgesics pp. 241-242, at 241 (1989).
Foye, W., Principles of Medicinal Chemistry; Structural Features and Pharmacologic Activity, pp. 63-66 at 65 (1989).
Goodman and Gilman, 1985, 7th edition, chapter 22, 491-530.
Goodman and Gilman, 1985, 7th edition, chapter 23, 533-579.
Gryczke et al, "Development and evaluation of orally disintegrating tablets (ODTs) containing Ibuprofen granules prepared by hot melt extrusion", Colloids and surfaces., B, Biointerfaces, Elsevier, Amsteram, NL, vol. 86, No. 2, Apr. 5, 2011, pp. 275-284.
Handbook of Pharmaceutical Excipients, 1986, American Pharmaceutical Association, Washington, DC and London (Table of Content Ohjy).
Hartauer, Kerry J. "Influence of Peroxide Impurities in Povidone and Crospovidone on the Stability of Raloxife" Pharma. Dev. & Tech, 5 (3) 303-310 (2000).
Henkel Corporation.
Investigation of a Directly Compressible Metformin HCl 500mg Extended Release Formulation Based on Hypromellose, Colorcon Jul. 2009.
Jannetto, P. et al, "Oxycodone: Recognition and Pharmacogenomics," Toxicology News, Mar. 2003, 1-7.
Kalant H. et al., Death in Amphetamine Users: Caues and Rates, CMA Journal, vol. 112 (Feb. 8, 1975): 299-304.
Kolter, K., "Compression Behaviour of Kollidon SR," APV/ APGI 2002, Florence, Apr. 11, 2002.
Kondrat, T. , "Technology dosage forms" Moscow 1991, p. 96.
Koziolek, M. et al., "Development of a bio-relevant dissolution test device simulating mechanical aspects present in the fed stomach," European Journal of Pharmaceutical Sciences 57 (2014) 250-256.
Lenindzer, A., "The molecular basis of the structure and functions of cells" Moscow 1974, p. 68.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.
Marques, Tablet breaking force, 2008.
Metformin Hydrochloride 1000 mg Extended Release Tablets, Lubrizol Advanced Materials, Inc., Nov. 20, 2009, Previous Edition Dec. 19, 2008.
Metformin Hydrochloride 750 mg Extended Release Tablets, Lubrizol Advanced Materials, Inc., Sep. 2010.
Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.
Mises à jour cumulatives, Vidal, Jan./Oct. 2002 (full translation attached).
Monolithic: retrieved from internet: http:/merriam-webster.com/dictionary/monolithic. Retrieved on Sep. 2, 2015.
Moorman-Li, R. et al, "A Review of Abuse-Deterrent Opioids for Chronic Nonmalignant Pain." Pharmacy and Therapeutics, vol. 37 No. 7, Jul. 2012, pp. 412-421.
Morissette et al. Advanced Drug Delivery Review 26 (2004), 275-300.
Note for Guidance on Stability Testing, EMEA, Aug. 2003, pp. 1-20.
Oliveira et al., "Production and characterization of laminar coextrudates at room temperature in the absence of solvents," AAPS Annual Meeting and Exposition, Oct. 14-18, 2012, Chicago, USA.
Oxicotin: Balancing Risks and Benefits, United States Senate, Hearing, Feb. 12, 2002.

(56) References Cited

OTHER PUBLICATIONS

Oxycodon (Oxygesic): Missbrauch, Abhaengigkeit and toedliche Folgen durch Injection zerstossener Retardtabletten, Deutsches Ärzteblatt, vol. 36, A2326-A2326, Sep. 5, 2003.
PCT International Search Report and Written Opinion for PCT Application No. PCT/EP2010/004459 dated Dec. 1, 2010.
PCT International Search Report and Written Opinion for PCT Application No. PCT/EP2009/003290 dated Jul. 9, 2009.
PCT International Search Report and Written Opinion for PCT Application No. PCT/EP2013/053894 dated Mar. 22, 2013.
PCT International Search Report and Written Opinion for PCT Application No. PCT/EP2013/059728 dated Aug. 6, 2013.
PCT International Search Report and Written Opinion for PCT Application No. PCT/EP2014/064830 dated Aug. 6, 2014.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
PCT International Search Report and Written Opinion for PCT Application No. PCT/EP2015/060377 dated Jul. 23, 2015.
PCT International Search Report and Written Opinion for PCT Application No. PCT/EP2015/061343 dated Jul. 21, 2015.
PCT International Search Report and Written Opinion for PCT Application No. PCT/EP2013/057851 dated Jun. 12, 2013.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Physico-mechanical Characterization of Polyox for Table Manufacture, Colorcon Jul. 2009.
Polyox water soluble resins 2003. http://www.dow.com/webapps/lit/litorder.asp?filepath=polyox/pdfs/noreg/326-00002.pdf.
POLYOX water-soluble resins (DOW Mar. 2002); see http://msdssearch.dow.com/PublishedLiteratureDOWCOM/dh_0031/0901b80380031a4a.pdf?filepath=/326-00001.pdf&fromPage=GetDoc).
POLYOX WSR-303, retrieved Mar. 10, 2014 from URL http://www.dow.com/dowwolff/en/industrial_solutions/polymers/polyethylene.
POLYOX, Colorcon, Application Data (Apr. 2009) downloaded from http://www.colorcon.com/literature/marketing/mr/Extended%20Release/POLYOX/English/ads_PEO_Antioxidant.pdf.
Pontier, C. et al, "Use of cycles of compression to characterize the behavior of apatitic phosphate powders," Journal of the European Ceramic Society 22 (2002), 1205-1216.
Quintavalle et al., "Preparation of sustained release co-extrudates by hot-melt extrusion and mathematical modelling of in vitro/in vivo drug release profiles," European Journal of Pharmaceutical Sciences 33 (2008), 282-293.
Remington, Chapter 45, pp. 996-1035. (Full Translation Attached).
Remington, The Science and Practice of Pharmacy, 19th ed., vol. II, p. 1457 (1995) (providing a table of DFA-approved commercially marketed salts).
Riippi M. et al., The effect of compression force on surface structure, crushing strength, friability and disintegration time of erythromycin acistrate tablets, Eur J Pharm Biopharm, vol. 46, 1998, pp. 339-345.
Ritschel et al. Die Tablette: Handbuch der Entwicklung, Herstellung und Qualitatssicherung. 2nd Edition, 2002, Table of content.
Rosiaux et al. "Ethanol-resistant ethylcellulose/guar gum coatings—Importance for formulation parameters" European Journal of Pharmaceutics and Biopharmaceutics, vol. 85, No. 3, (Jul. 25, 2013). pp. 1250-1258.
Rowe C et al., Handbook of Pharmaceutical Excipients, 7th Edition, 2012, Table of Contents.
Saleem et al. "Formulation and Evaluation of Tramadol hydrochloride Rectal Suppositories," Indian J. Pharm Sci. Sep.-Oct. 2008; 70(5), 640-644.
Salomies et al., "Determination of Oxycodone Hydrochloride in Oral Solutions by High-Performance Thin-Layer Chromatography/Densitometry," Journal of AOAC International, 83: 1497-1501 (2000).
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Sax et al., Hawley's Condensed Chemical Dictionary, 11th ed., 1987, p. 1233, definition of "wax".
Schilling, et al., "Novel application of hot-melt extrusion for the preparation of monolithic matrices containing enteric-coated particles." International Journal of Pharmaceutics 400 (2010) 34-31.
Search result conducted on http://www.unitconversion.org/force/newtons-to-kiloponds-convresion.html, on Jul. 5, 2011 (Conversion of 18.8 kiloponds to newtons).
Sidhu et al., "Watch for nonpsychotropics causing psychiatric side effects," Current Psychiatry, vol. 7, No. 4, 2008, 61-74.
Silver, J. "Painkiller OxyContin" most commonly abused prescription drug on the streets of Western Pennsylvania, Pittsburg Post-Gazette, Apr. 8, 2001.
Spassov et al., Stereochemistry of Diastereomeric 3-Dialkylaminopropanols and O-Derivatives, J.f. prakt. Chemie, 323:5, 793-800 (1981).
Sreenivasa, B. et al, Design and Evaluation of Ethylene Vinyl Acetate Sintered Matrix Tablets, Indian Journal of Pharmaceutical Sciences, Sep.-Oct. 2003, 65(5): 496-502.
Starch 1500, Partially Pregelatinized Maize Starch, technical data from Colorcon, Feb. 2016, 6 pages.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 20, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.

(56) References Cited

OTHER PUBLICATIONS

Tennant, "Simultaneous Use of Stimulants and Opioids," 2011 [online] retrieved on Jul. 7, 2016 from: http://www.practicalpainmanagement.com/treatments/pharmacological/opioids/simultaneous-use-stimulants-opioids; 7 pages.
The Merck Index, 14th Ed. (2006) No. 0006360 Nalefene.
The Merck Index, 14th Ed. (2006) No. 0006362 Naloxone.
The Merck Index, 14th Ed. (2006) No. 0006363 Naltrexone.
The Merck Index, 14th Ed. (2006) No. 0006959 Oxycodone.
Tikhonov, A. et al, Biopharmacy. The Manual for Students of Pharmaceutical Universities and Departments, 2003, pp. 40-41, Kharkov, Ukraine (Full English translation attached).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Verhoeven, et al. "Xanthan gum to tailor drug release of sustained-release ethylcellulose mini-matrices prepared via hotmelt extrusion: in vitro and in vivo evaluation," European Journal of Pharmaceutics and Biopharmaceutics, 63 (2006) 320-330.
Vippagunta et al. Crystalline Solids, Advanced Drug Delivery Review 48 (2001), 3-26.
Vynckier et al.,"Hot-melt co-extrusion for the production of fixed-dose combination products with a controlled release ethylcellulose matrix core," International Journal of Pharmaceutics 464 (2014), 65-74.
Wagner, Pharmazeutische Biologie—Drogen und ihre Inhaltsstoffe—Scharfstoffdrogen, 2nd., revised edition, Gustav Fischer Verlag, Stuttgart-N.Y., 1982,Table of Content.
West, Anthony R., Solid state chemistry and its applications, Wiley, New York, 1988, pp. 358 and 365.
Wikipedia-Dextromethorphan Aug. 12, 2013 (and attached related English-language entry dated Dec. 11, 2013).
Zeeshan, F and N. Bukhari, "Development and Evaluation of a Novel Modified-Release Pellet-Based Tablet System for the Delivery of Loratadine and Pseudophedrine Hydrochloride as Model Drugs," AAPS PharmaSciTech 11(2); 910-916 (available on-line May 22, 2010).
Woodburn, K.R. et al., Vascular complications of injecting drug misuse, Br. J. of Surgery, vol. 83, 1996, pp. 1329-1334.
Extended European Search Report for Application No. EP 16182124. 4-1455, dated Jan. 17, 2017.
USP Expert Council, US Pharmacopoeia, Chapter 1092, 2007, 1-15.
M. Xu et al., "Evaluation of the coat quality of sustained release pellets by individual pellet dissolution methodology," Int. J. Pharm. 478 (2015) 318-327.
PCT International Search Report and Written Opinion for PCT Application No. PCT/EP2017/070396 dated Sep. 8, 2017.
COMPAP 90 technical data sheet Mar. 2014; 1 page.
Furu et al. "use of ADHD drugs in the Nordic countries: a population-based comparison study," Acta Psychiatrica Scandinavia, May 2010.
Decision of the United States District Court for the Southern District of New York, in In re *Endo Pharmaceuticals Inc. and Grünenthal GmbH* v. *Amneal Pharmaceuticals, LLC et al.*, Findings of Fact and Conclusions of Law, District Judge Thomas P. Griesa, New York, New York, Jan. 14, 2015.
Decision of the United States District Court for the Southern District of New York, in In re *Oxycontin Antitrust Litigation, Purdue Pharma LP* v. *Teva Pharmaceuticals*, Findings of Fact and Conclusions of Law, District Judge Sidney H. Stein, New York, New York, Jan. 14, 2014.
U.S. Court of Appeals, Federal Circuit, *Purdue Pharma L.P.* v. *Epic Pharma, LLC*, 117 USPQ2d 1733 (Fed. Cir. 2016).

Al-Angari, A. et al. "The compaction properties of polyethylene glycols," J Pharm. Pharmacol. (1985) 37:151-153.
Al-Nasassrah et al. , "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 8:2944-54 (1995).
Back, D.M.et al., "Ethylene Oxide Polymers", in Kirk-Othmer Encyclopedia of Chemical Technology: 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1): 8-11.
Balogh, E., "Tastes in and Tastes of Paprika," in Taste: Proceedings of the Oxford Symposium on Food and Cookery 28 (Tom Jaine Ed.) 1988, pp. 25-40.
Baumann, T., "Pain Management," Pharmacotherapy: A Pathophysiologic Approach (J.T. DiPiro et al. eds., McGraw-Hill 4th ed. 1999), Ch. 56, 1014-1026.
Baumrucker, S.J., "OxyContin, the Media, and Law Enforcement", American Journal of Hospice & Palliative Care, 18:3 (May/Jun. 2001), 154-156.
Choi, S., et al., "Development of a Directly Compressible Poly(Ethylene Oxide) Matrix or the Sustained-Release of Dihydrocodeine Bitartrate", Drug Development and Industrial Pharmacy, vol. 29, No. 10, pp. 1045-1052, 2003.
Choi, S., et al., "Hydrophilic Matrix Formulations of Dihydrocodeine Bitartrate with Polyethylene Oxide by Direct Compression," Proceedings of the $29^{th}$ Annual Meeting of the Controlled Release Society, in collaboration with the Korea Society for Biomaterials, Minneapolis, $1^{st}$ Edition, 2002, 984-985.
Ciccone, P. E., "Attempted Abuse of Concerta," Letters to the Editor, J. Am. Acad. Child Adolesc. Psychiatry, 41:7 (Jul. 2002).
Controversies in ADHD: A Breakfast Symposium—Concerta.
Crowley, M. et al., Pharmaceutical Applications of Hot-Melt Extrusion: Part I. Drug Dev. & Indus. Pharmacy (2007) 33:909-926.
Crowley, M. et al., "Properties of Hot-Melt Extruded CPM Tablets Using Hydrophilic Polymers," poster presentation, (2000).
Crowley, M., "Physicochemical and Mechanical Characterization of Hot-Melt Extruded Dosage Forms." Dissertation presented to the Faculty of the Graduate School of the University of Texas at Austin. (May 2003).
Crowley, M., et al., "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, IN (2000).
CROWLEY0000001—CROWLEY0000127.
Davies, N. "Sustained Release and Enteric Coated NSAIDs: Are They Really GI Safe?" J. Pharm. & Pharmaceut. Sci., 2(1):5-14, 1999.
Declaration of Dr. James W. McGinity, dated Oct. 28, 2009; online, retrieved from: http://www.accessdata.fda.gov/dmgsatfda_docs/labeV2013/021121s032lbl.pdf.
Dimitrov, M, et al., "Study of Verapamil hydrochloride release from compressed hydrophilic Polyox-Wsr tablets." Int'l J Pharmaceutics (1999) 189:105-111.
Dittmer, D.K., et al., "Glue-Sniffing Neuropathies," Canadian Family Physician 39:1965-1971 (1993).
Donnelly, C.L., "ADHD Medications: Past and Future," Behavioral Health Management, May/Jun. 2002, 28 & 30.
Dow, "Material Safety Data Sheet: POLYOX(TM) WSR 30" (effective date: Sep. 18, 2001).
Dow, "POLYOX Water-Soluble Resins: Degradation of Water-Soluble Resins," Technical Data (Oct. 2002).
Drug Bank "Oxymorphone," 2015; online, available at: www.dmgbank.ca/chugs/db01192 printed Jul. 1, 2015.
*Endo Pharmaceuticals Inc.* v. *Teva Pharmaceuticals USA, Inc.* (S.D.N.Y 2015)—Redacted Version.
FDA News Release, "FDA approves abuse-deterrent labeling for reformulated OxyContin," Apr. 16, 2013, available at http://www.fda.gov/NewsEvents/Newsroom/Press.Announcements/ucm348252.htm.

(56) References Cited

OTHER PUBLICATIONS

FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.
Final Draft Labeling for Concerta Extended-Release Tablets Attachment to Approval Letter (2000); available at: http://www.accessdata.fda.gov/drugsatfda_docs/label/2000/21121lbl.pdf.
Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).
Griffith, D., "Potential new ADHD drug creating lots of big hopes," Sacramento Bee (California), Oct. 30, 2002.
Huang, H. et al., "Preparation of Controlled Release Oral Dosage Forms by Low Temperature Melt Extrusion," AAPS PharmSci. 2000 2(S1).
Jaffe, S.L., "Failed Attempts At Intranasal Abuse of Concerta," Letters to the Editor, J. Am. Acad. Child Adolesc. Psychiatry, 41:1 (Jan. 2002).
Jannsen Pharmaceuticals, Inc. Concerta Labeling Revisioins, Dec. 12, 2013; online, retrieved from: http://www.accessdata.fda.gov/dmgsatfda_docs/labeV2013/021121s032lbl.pdf.
Joint Claim Construction and Prehearing Statement, dated Jul. 11, 2014. *Janssen Pharmaceuticals, Inc. and Grünenthal GMBH v. Actavis Elizabeth LLC and Alkem Laboratories Limited*, Civil Action No. 2:13-cv-04507 CCC-MF (D.N.J.), *Janssen Pharmaceuticals, Inc. and Grünenthal GMBH v. Roxane Laboratories, Inc.*, Civil Action No. 2:13-cv-06929 CCC-MF (D.N.J.), and *Janssen Pharmaceuticals, Inc. and Grünenthal GMBH v. Alkem Laboratories Limited*, Civil Action No. 2:13-cv-07803 CCC-MF (D.N.J.).
Kibbe, Coloring Agents, in Handbook of Pharmaceutical Excipients (3d ed. 2000).
Kidokoro, M. et al. ,"Properties of Tablets Containing Granulations of Ibuprofen and Acrylic Copolymers Prepared by Thermal Processes," Pharm Dev. and Tech. , 6:263-275 (2001).
Kinjo, N. et al, "Antiplasticization in the Slightly Plasticized Poly(vinyl chloride)," Polymer Journal 4(2):143-153 (1973).
Larhib, H. et al., "Compressing polyethyelene glycols: the effect of compression ressure and speed," Int'l J Pharmaceutics (1997) 147: 199-205.
Lieberman, H., et al., Pharmaceutical Dosage Forms: Tablets, vol. 2, Ch. 5: Granulation Technology and Tablet Characterization (1990), Table of contents and 245-348.
Lyons et al., "Twitch Interpolation in the Assessment of the Maximum Force-Generating Capacity of the Jaw-Closing Muscles in Man," Arch. Oral. Biol. 41:12, 1161-1168 (1996).
Makki, A, et. Al., Eds., A Dictionary of American Idioms, 4th Ed. Barron's, New York (2004), 342-343.
Markovitz, H., et al. "Calculations of Entanglement Coupling Spacings in Linear Polymers." Journal of Physical Chemistry 1962. 66(8): 1567-1568.
McCrum, N., et al., Principles of Polymer Engineering. 2nd ed., New York: Oxford University Press. 447(1997), Chapter 7, 296-351.
McGinity, J.W. et al., "Melt-Extruded Controlled-Release Dosage Forms" in Pharmaceutical Extrusion Technology, Ghebre-Sellassie, I. and Martin, C., Eds., Marcel Dekker, Inc., New York, 2003, Chapter 10, 183-208.
McQuay, H. et a. "Methods of Therapeutic Trials," Textbook of Pain 1125-1138 (P.D. Wall & R. Melzack eds., Elsevier 4th ed. 1999), Table of Contents and 1125-1138.
Miura et al., "Comparison of Maximum Bite Force and Dentate Status Between Healthy and Frail Elderly Persons," J. Oral Rehabilitation, vol. 28 (2001), pp. 592-595.
Miyagawa, Y. et al., "Controlled-release of diclofenac sodium from wax matrix granulate," Int'l J. Pharmaceutics (1996) 138:215-224.
National Drug Intelligence Center Information Bulletin "OxyContin Diversion and Abuse" Jan. 2001.
Payne, H. et al., Denatonium Benzoate as a Bitter Aversive Additive in Ethylene Glycol and Methanol-Based Automotive Products, SAE Technical Paper 930589, Abstract (1993).
Pilpel, N., et al. "The effect of temperature on the tensile strength and disintegration of paracetamol and oxytetracylcine tablets," J Pharm Pharmac., 29:389-392 (1977).
POLYOX Water-Soluble Resins NF in Pharmaceutical Applications, Dow Chemical Company, Aug. 2002.
Purdue Pharma LP Material Safety Data Sheet, OxyContin Tablets, 10 mg, 15 mg, 20 mg, 30 mg, 40 mg, 60 mg, Version 16—Sep. 2010; available at www.purduephruma.com/msdss/oxycontin_msds.pdf.
Rauwendaal, Chris, PHD, Responsive Expert Report of Chris Rauwendaal, Ph.D. Regarding Expert Report of Michael M. Crowley, Ph.D., dated Jul. 17, 2015.
Repka, M. et al. Pharmaceutical Applications of Hot-Melt Extrusion: Part II. Drug Dev. & Indus. Pharmacy (2007) 33:1043-1057.
Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.
Seitz, J.A.; et al., "Evaluation of the Physical Properties of Compressed Tablets 1: Tablet Hardness and Friability," J. of Pharm. Sci. , 54:1353-1357 (1965).
Shah, et al., "Some Effects of Humidity and Heat on the Tableting Properties of Microcrystalline Cellulose Formulations 1," J. of Pharm. Sci., 57:181-182 (1967).
Singhal, et al., Handbook of Indices of Food Quality and Authenticity (1997), "Capsicum" p. 398-299.
Smith, K.L. et al. "High Molecular Weight Polymers of Ethylene Oxide—Plastic Properties." Industrial and Engineering Chemistry, 1958. 50(1): 12-16.
Tapentadol Pre-Review Report, Expert Committee on Drug Dependency Thirty-Fifth Meeting Hammamet, Tunisia, Jun. 4-8, 2012, available at http ://www.who.int/medicines/areas/quality_safety/5.2Tapentadolpre-review.pdf.
Tiwari, D., et al., "Evaluation of polyoxyethylene homopolymers for buccal bioadhesive drug delivery device formulations." AAPS Pharmsci, 1999. 1(3): Article 13.
Wilkins, J.N., "Pharmacotherapy of Schizophrenia Patients with Comorbid Substance Abuse," Schizophrenia Bulletin, 23:215-228 (1997).
World Health Org., Cancer Pain Relief With a Guide to Opioid Availability (2d ed. 1996).
Yin, T.P., et al., "Viscoelastic Properties of Polyethylene Oxide in Rubber-Like State." Journal of Physical Chemistry, 1961. 65(3): 534-538.
Zacny, J. et al. Drug & Alcohol Dependence (2003) 69:215-232.
Zhang, F., "Hot-Melt Extrusion as a Novel Technology to Prepare Sustained-Release Dosage Forms," Dissertation University of Texas at Austin, Dec. 1999.
Dabbagh et al. "Release of Propranolol Hydrochloride from Matrix Tablets Containing Sodium Carboxymethylcellulose and Hydroxypropylmethylcellulose"; 1999; Pharmaceutical Development and Technology, 4(3), 313-324.
Bannwarth, Bernard, "Will Abuse-Deterrent Formulations of Opioid Analgesics be Successful in Achieving Their Purpose?", Drugs, 2012, vol. 72, pp. 1713-1723.
Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.
Apicella A.et al., Biomaterials, vol. 14, No. 2, pp. 83-90, 1993.
*Grünenthal GmbH, et al., v. Watson Laboratories and Andrx Labs*, Civil Action No. 11-2036 (S.D.N.Y.).
*Grünenthal GmbH, et al., v. Teva Pharmaceuticals USA, Inc, et al.*, Civil Action 11-2037 (S.D.N.Y.).
*Grünenthal GmbH, et al., v. Actavis Elizabeth, L.L.C.*, Civil Action No. 11-2038 (S.D.N.Y.).
*Grünenthal GmbH, et al., v. Impax Laboratories., Inc.*, Civil Action No. 11-2400 (S.D.N.Y.).
*Grünenthal GmbH, et al., v. Sandoz Inc, et al.*, Civil Action No. 11-4694 (S.D.N.Y.).

(56) References Cited

OTHER PUBLICATIONS

*Grünenthal GmbH, et al.,* v. *Amneal Pharmaceuticals, L.L.C.*, Civil Action No. 11-8153 (S.D.N.Y.).
*Grünenthal GmbH, et al.* v. *Sandoz, Inc.* No. 1:12-cv-0897 (SHS)(S.D.N.Y.).

* cited by examiner

A

---

B¹

B²

B³

A

B

C¹

C²

A

B

C¹

C²

Depth into tablet

A

B

HOT-MELT EXTRUDED PHARMACEUTICAL DOSAGE FORM

FIELD OF THE INVENTION

The invention relates to a hot-melt extruded pharmaceutical dosage form exhibiting an increased breaking strength (resistance to crushing). The pharmaceutical dosage form is characterized by a modified release profile of the pharmacologically active compound contained therein.

BACKGROUND ART

For many pharmaceutically active compounds it is preferred to have them orally administered by way of tablets. It is well known that depending on how a pharmaceutically active ingredient is formulated into a tablet its release pattern can be modified. In this regard, tablets providing a controlled release profile are of primary importance. With controlled release tablets care has to be taken that under no circumstances the pharmaceutically active ingredient will be released completely and instantaneously in an uncontrolled manner ("dose-dumping") since regularly the dosage used for controlled, particularly for retarded release tablets is much higher than for non-retarded release tablets. This may cause serious adverse effects or even death depending on the active ingredient and potency thereof.

Controlled release (e.g. retarded release, delayed release, prolonged release, sustained release, and the like) may be based upon various concepts such as coating the pharmaceutical dosage form with a controlled release membrane, embedding the pharmacologically active compound in a matrix, binding the pharmacologically active compound to an ion-exchange resin, forming a complex of the pharmacologically active compound, and the like. In this context it can be referred to, e.g., W. A. Ritschel, Die Tablette, 2. Auflage, Editio Cantor, Aulendorf, 2002.

Pharmaceutical dosage forms having an increased breaking strength (resistance to crushing) have been recently reported. Dosage forms of this type may also exhibit a certain degree of controlled release of the pharmacologically active compound contained therein. The major advantage of such pharmaceutical dosage forms is that comminuting, particularly pulverization, by conventional means, such as grinding in a mortar or fracturing by means of a hammer, is impossible or at least substantially impeded.

On the one hand, pharmaceutical dosage forms having an increased breaking strength are useful for avoiding drug abuse of the pharmacologically active compound contained therein. Many pharmaceutical active compounds, in addition to having excellent activity in their appropriate application, also have abuse potential, i.e., they can be used by an abuser to bring about effects other than those intended. Opiates, for example, which are highly active in combating severe to very severe pain, are frequently used by abusers to induce a state of narcosis or euphoria. In order to make abuse possible, the corresponding pharmaceutical dosage forms, such as tablets or capsules are comminuted, for example ground in a mortar, by the abuser, the active compound is extracted from the resultant powder using a preferably aqueous liquid and the resultant solution, optionally after being filtered through cotton wool or cellulose wadding, and is administered parenterally, in particular intravenously. An additional phenomenon of this kind of administration, in comparison with abusive oral administration, is a further accelerated increase in active compound levels giving the abuser the desired effect, namely the "kick" or "rush". This kick is also obtained if the powdered pharmaceutical dosage form is administered nasally, i.e. is sniffed. Since controlled-release pharmaceutical dosage forms containing active compounds with abuse potential do not give rise to the kick desired by the abuser when taken orally even in abusively high quantities, such pharmaceutical dosage forms are also comminuted and extracted in order to be abused. Pharmaceutical dosage forms exhibiting an increased breaking strength, however, may not be powdered by conventional means and thus, cannot be administered nasally thereby avoiding drug abuse. In the context of such tamper resistant dosage forms, it can be referred to, e.g., WO 2005/016313, WO 2005/016314, WO 2005/063214, WO 2005/102286, WO 2006/002883, WO 2006/002884, WO 2006/002886, and WO 2006/082097.

On the other hand, pharmaceutical dosage forms having an increased breaking strength are useful for avoiding an (unintentional) overdose of the pharmacologically active compound contained therein, which overdose would otherwise be caused by diminishing the retardant effect due to pulverization. It is known that many patients, particularly older patients frequently have difficulties in taking solid pharmaceutical dosage forms, such as tablets, gelatine capsules, etc. They choke on them and sometimes develop pronounced aversion to such pharmaceutical dosage forms. To counter this problem, various apparatuses have been developed by means of which conventional solid pharmaceutical dosage forms may be comminuted or pulverized ("tablet crushers"). Such apparatuses are used, for example, by the care staff in old people's homes. The pharmaceutical dosage forms are then administered to the people being cared for not as tablets etc. but rather as powder, for example to get round the difficulties involved in swallowing tablets. However, the commination of pharmaceutical dosage forms with such apparatuses is problematic if the pharmaceutical dosage forms are prolonged-release formulations. As a rule, comminution results in destruction of the inner structure of the pharmaceutical dosage form, which is responsible for the prolonged release, so doing away with the prolonged-release action. Consequently, after administration, frequently all the physiologically active substance originally contained in the pharmaceutical dosage form is released in a relatively short time, whereby a comparatively very high plasma concentration of the substance is abruptly reached within a relatively short time frame. In this way, the originally prolonged-release formulations become immediate release formulations. Depending on the physiological activity of the substance, this may cause considerable side-effects however, and in extreme cases may even lead to the death of the patient. Pharmaceutical dosage forms having an increased breaking strength, however, cannot be comminuted by tablet crushers and thus, have to be swallowed as a whole thereby avoiding any (unintentional) overdose. In this context, it can be further referred to, e.g., WO 2006/082099.

The release profile of controlled-release formulations depends on a variety of factors, such as properties of the pharmaceutical dosage form per se, nature and content of the matrix, nature of the release medium, nature and content of the active compound, nature and content of further pharmaceutical excipients as well as the interrelationship of these factors. When the control of the release profile relies on a polymer matrix in which the active compound is embedded, the release rate depends on the properties of the pharmaceutical dosage form as such, e.g. its geometry, method of manufacture, additives and excipients contained therein, and the like. Further, the release rate depends on the properties of the matrix polymer, such as molecular weight, viscosity, particle properties, interaction with other polymers, chain entanglements, degree of cross-linking, chemical nature of monomer units, interaction of the matrix material with the release medium (e.g., swelling and gelling), and the like. Still further, the release rate depends on the properties of the active compound, e.g., its dose, particle size, particle form and its solubility in the release medium, which in turn is a function of various properties, such as molecular size, molecular weight, ionogenicity, acidity, steric hindrance, arrangement of dipols, hydrophilicity, etc. Furthermore, the release rate depends on the individual interactions of a given matrix material with a given active compound (cf. Ning Wu et al., Journal of Controlled Release 102 (2005) 569-81; V. S. Manthena et al., Am J Drug Deliv. 2004 2 (1) 43-57).

The release profile of conventional pharmaceutical dosage forms that do not exhibit an increased breaking strength can usually be adjusted within certain limits, usually by the variation of the content and/or the nature of the pharmaceutical excipients, such as the matrix forming polymer.

In some cases it has also been reported that the release of a drug in the body can be controlled by the surface area to volume ratio of a conventional dosage form which does not exhibit an increased breaking strength. For example, U.S. Pat. No. 5,427,798 discloses film coated tablets containing bupropion hydrochloride and having a surface area to tablet volume of 3:1 to 25:1 $cm^{-1}$ for tablets of 50, 100 and 150 mg drug content. Similarly, U.S. Pat. No. 4,940,556 and U.S. Pat. No. 5,198,226 disclose spheroids containing dihydropyridine calcium channel blockers and having area radius to circumference radius ratios in the range of 0.85 to 1.0.

With respect of pharmaceutical dosage forms exhibiting an increased breaking strength, however, the variation of the content, the nature of the pharmaceutical excipients and/or the surface area to volume ratio also affects the mechanical properties. This is because the increased breaking strength of the pharmaceutical dosage form typically relies on the presence of a particular polymer that is processed by a particular method when manufacturing the pharmaceutical dosage form. It seems that said polymer also serves as a matrix embedding the pharmacologically active compound. In consequence, the polymer matrix that is essential to the breaking strength of the pharmaceutical dosage form simultaneously serves as a controlled release matrix and thus, varying the content, nature and/or spatial distribution of the polymer causes both, a change of the release profile as well as a change of the mechanical properties of the pharmaceutical dosage form.

Particular problems arise when the dose of the pharmacologically active compound and thus, also the total weight of the pharmaceutical dosage form is comparatively high. Depending upon the content and the nature of the pharmacologically active compound and of the pharmaceutical excipients, the retardant effect of the polymer may be so strong that the pharmaceutical dosage form cannot be adapted to a specific dosing regimen, e.g., twice daily, particularly when the increased breaking strength is to be maintained.

On the one hand, a decrease of the content of the retardant polymer for the purpose of accelerating drug release would substantially affect the mechanical properties of the pharmaceutical dosage form and in a worst case scenario, would completely diminish its specific and unique mechanical properties (breaking strength). Further, a decrease of the content of the matrix polymer beyond a certain limit may cause a deterioration or even loss of other desired properties, such as storage stability. A poor storage stability results, e.g., in a change of the release profile over time.

On the other hand, the addition of non-retardant pharmaceutical excipients (auxiliaries) for the purpose of weakening the retardant effect of the retardant polymer would increase the total weight of the dosage form. As highly dosed pharmaceutical dosage forms have comparatively high total weights anyway, a further increase of the total weight is disadvantageous and could deteriorate patient compliance (e.g. swallowability).

Furthermore, a pharmaceutical formulation or its mode of manufacture, e.g. for an oral dosage form, might undergo modifications during clinical testing, for example with respect to the ingredients used or to the relative amounts of the pharmaceutical excipients, or with respect to the reaction conditions and reactants used during manufacture. Frequently, such modifications at least to some extent have an impact on the release profile of pharmaceutically active ingredients. This is particularly unpleasant if for a specific formulation an approved optimized release profile has already been found which cannot be reproduced with the modified formulation. In such a case, the clinical tests have either to be interrupted or have to be started from the beginning. Given the huge expenditures necessary to bring a new drug formulation up to and through clinical testing the above scenario has indeed proven to be rather unsatisfactory.

Thus, there is a demand for tamper resistant pharmaceutical dosage forms the release profile of which may be varied within certain limits without diminishing the tamper resistance, without substantially changing the nature or amount of the pharmaceutical excipients, and without deteriorating the compliance of the pharmaceutical dosage form.

It is an object of the invention to provide pharmaceutical dosage forms having advantages compared to pharmaceutical dosage forms of the prior art.

This object has been solved by the subject-matter of the patent claims.

SUMMARY OF THE INVENTION

The invention relates to a hot-melt extruded pharmaceutical dosage form with controlled release of a pharmacologically active ingredient embedded in a matrix comprising a polymer, the dosage form exhibiting a breaking strength of at least 300 N, preferably at least 500 N, and having an oblong shape comprising a longitudinal direction of extension, a transversal direction of extension orthogonal to the longitudinal direction of extension, a front side, an opposite back side and a circumferential rim between said front and back side;

wherein
  the core of the pharmaceutical dosage form has a morphological orientation caused by hot-melt extrusion that is substantially orthogonal to the longitudinal direction of extension of the dosage form; and/or
  the release of the pharmacologically active ingredient through the front side and the opposite back side is faster than the release through the circumferential rim.

It has been surprisingly found that the release rate of the dosage form can be modified by modifying the shape of the extrudate from which the dosage form is formed, in particular by modifying the area ratio of the front faces (cut surfaces) of the extrudate relative to the jacket (barrel) of the extrudate.

Surprisingly, the release rate is accelerated when the area of the cut surfaces increases. It seems that said cut surfaces exhibit a faster release of the pharmacologically active ingredient than the jacket (barrel) of the extrudate. Thus, when press-forming a pharmaceutical dosage form from an extrudate, those surface areas of the pharmaceutical dosage form originating from the front faces of the extrudate seem to show a faster release than those surface areas originating from the jacket (barrel) of the extrudate. This effect can be advantageously used in order to adjust the release profile of the pharmacologically active ingredient from the pharmaceutical dosage form, either in an accelerating manner or in a decelerating manner.

Furthermore, it has been surprisingly found that the mechanical properties of the pharmaceutical dosage form, particularly its breaking strength, depend upon the relative position of the direction of extrusion within the body of the pharmaceutical dosage form. Thus, the mechanical properties of the pharmaceutical dosage forms can be improved by placing the direction of extrusion into a proper direction within the body of the dosage form.

BRIEF DESCRIPTION OF THE DRAWINGS

FIG. 1A is a side view and Figures $B^1$ to $B^3$ are top views of cross-sections of alternative dosage form having different oblong shape.

FIG. 2A shows the separation of the extrudate from the extruded strand having a circular cross-section, FIG. 2B shows the shaping of the dosage form from the extrudate by means of a tabletting tool equipped with upper punch and lower punch, FIG. $2C^1$ shows the resultant dosage form as a side view and FIG. $2C^2$ shows the resultant dosage form as top view of the cross-section.

FIG. 3A shows the separation of the extrudate from the extruded strand having an oblong cross-section, FIG. 3B shows the shaping of the dosage form from the extrudate by means of a tabletting tool equipped with upper punch and lower punch, FIG. $3C^1$ shows the resultant dosage form as a side view and FIG. $3C^2$ shows the resultant dosage form as top view of the cross-section.

FIG. 4A illustrates top view and side view also indicating the curvature of the circumference surrounding the recesses. FIG. 4B illustrates top view and side view also indicating the direction of extrusion relative to the body of the dosage form.

FIG. 5A shows the results of a terahertz pulsed imaging measurement (image of the cross section of an extrusion strand). FIG. 5B shows the results of a terahertz pulsed imaging measurement (image of the longitudinal section of an extrusion strand).

DETAILED DESCRIPTION OF THE INVENTION

A first aspect of the invention relates to a hot-melt extruded pharmaceutical dosage form with controlled release of a pharmacologically active ingredient (A) embedded in a matrix comprising a polymer (C), the dosage form preferably being adapted for oral administration and having an oblong shape comprising a longitudinal direction of extension, a transversal direction of extension orthogonal to the longitudinal direction of extension, a front side, an opposite back side and a circumferential rim between said front and back side;
wherein
    the core of the pharmaceutical dosage form has a morphological orientation caused by hot-melt extrusion that is substantially orthogonal to the longitudinal direction of extension of the dosage form; and/or
    the release per area of the pharmacologically active ingredient (A) through the front side and the opposite back side is faster than the release through the circumferential rim.

Figure 1:
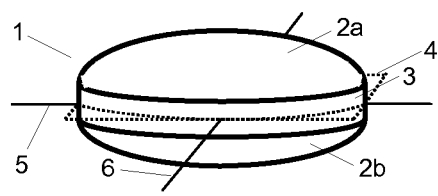
FIG. 1 is a schematic view of a preferred embodiment of the pharmaceutical dosage form according to the invention.
Figure 1:
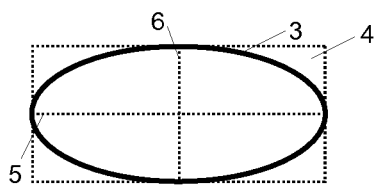
Figure 1:
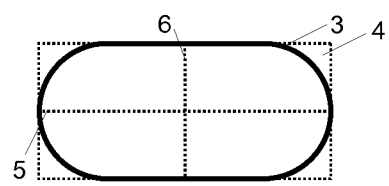
Figure 1:
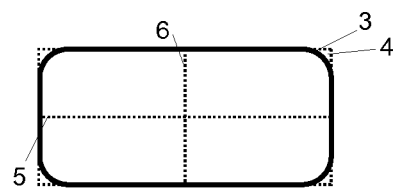

A preferred embodiment of the hot-melt extruded pharmaceutical dosage form according to the invention is further schematically illustrated in FIG. 1.

FIG. 1A is a perspective view of a preferred embodiment of a pharmaceutical dosage form (1) comprising a front side (2a), a back side (2b) as well as a circumferential rim (3) between front side (2a) and back side (2b). Plane (4) lies within the body of the pharmaceutical dosage form (1) and includes longitudinal direction of extension (5) that is orthogonal to transversal direction of extension (6). This embodiment can be regarded as a biconvex oblong dosage form.

FIGS. $1B^1$, $1B^2$ and $1B^3$ are top views of alternative preferred embodiments of plane (4) including circumferential rim (3), longitudinal direction of extension (5) and transversal direction of extension (6). According to the embodiment depicted in FIG. $1B^1$, circumferential rim (3) assumes the shape of an ellipse with longitudinal direction of extension (5) being the semi-major axis and transversal direction of extension (6) being the semi-minor axis. According to the embodiment depicted in FIG. $1B^2$, circumferential rim (3) assumes the shape of two half-circles with a rectangle in between. According to the embodiment depicted in FIG. $1B^3$, circumferential rim (3) assumes the shape of a rectangle with rounded corners.

When manufacturing conventional hot-melt extruded oblong pharmaceutical dosage forms, a mass comprising the pharmacologically active ingredient and further pharmaceutical excipients is hot-melt-extruded through a die. Conventionally, the die has a circular shape yielding an extrudate with a circular cross-section (cylinder). Extrusion causes the constituents in the mass to somewhat orientate in a one-dimensional fashion such that the resultant extrudate (extruded strand) has a morphological orientation in the direction of extrusion. The morphological orientation can be visualized by suitable analytical methods.

Said extrudate is then separated (singulated), typically cut into cylinders, usually in a plane substantially orthogonal to the direction of extrusion. Each cylinder has two opposing surfaces as well as a circumference (barrel/jacket). The opposing surfaces are produced in the course of separating (e.g., cutting) the extrudate into cylinders. The circumference is produced in the course of the extrusion process (barrel/jacket of the extruded strand). Subsequently, said cylinders are press-formed into oblong dosage forms, e.g., by means of a tabletting machine. For geometrical reasons, the cylinders are typically placed into the tabletting tool so that the longitudinal axis of the cylinder parallels the longitudinal direction of extension of the punch.

Press-forming the extrudates typically changes the outer shape of the dosage form. Thus, the shape of the dosage form typically differs from the shape of the extrudate, which can be regarded as an intermediate of the manufacturing process.

When manufacturing the pharmaceutical dosage forms according to the invention, hot-melt-extrusion is preferably performed through an oblong die yielding an extrudate with an oblong cross-section. Thus, separation (singulation) yields slices (extrudates) having two opposite oblong surfaces, e.g. cut surfaces. When placing said slices into a tabletting tool comprising upper punch and lower punch in a manner so that the opposing surfaces of oblong shape face said upper and lower punch, respectively, the front and opposite back side of the dosage form are made from (originate from) the cut surfaces of the slice, whereas in the circumferential rim of the dosage form is made from (originates from) the barrel/jacket of the extrudate. In consequence, the direction of extrusion is substantially orthogonal to the longitudinal direction of extension of the dosage form.

A skilled person is fully aware that when press-forming the dosage form from the extrudate, the morphological orientation of the material in the extrudate is changed. At least in the outer regions of the extrudate press-forming causes the material to flow in order to exactly fill the die/punch that is used in press-forming and that determines the final outer shape of the dosage form. However, the material forming the core of the extrudate is not moved or only moved to a slight extent in the course of press-forming and hence, the core substantially maintains its morphological orientation. Thus, the core of the dosage form serves as a reference point or bench mark to define the morphological orientation of the material relative to the outer dimensions of the dosage form.

For the purpose of the specification, the core of the dosage form constitutes the centre volume element having at most 50% of the total volume of the dosage form, more preferably at most 40%, still more preferably at most 30%, yet more preferably at most 20% and in particular at most 10% of the total volume of the dosage form. Therefore, when deciding whether the morphological orientation of the material in the core is substantially orthogonal to the direction of extrusion, the proper core element should be investigated by suitable analytical methods such as terahertz spectroscopy or high-resolution imaging techniques like electron microscopy, electron raster microscopy, electron force microscopy, NIR-microscopy and the like. Alternative methods include solid state NMR, photoelectron spectroscopy and X-ray methods.

Figure 2:
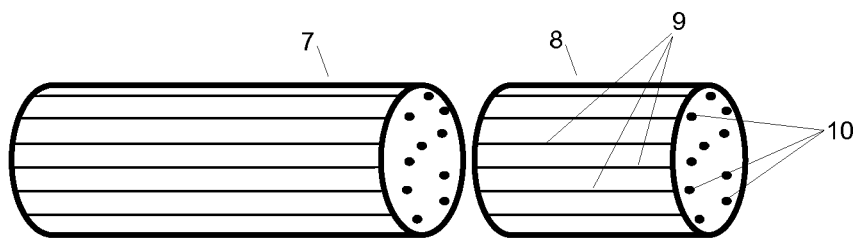
FIG. 2 schematically illustrates the conventional manufacture of oblong hot-melt extruded pharmaceutical dosage forms having an increased breaking strength.
Figure 2:
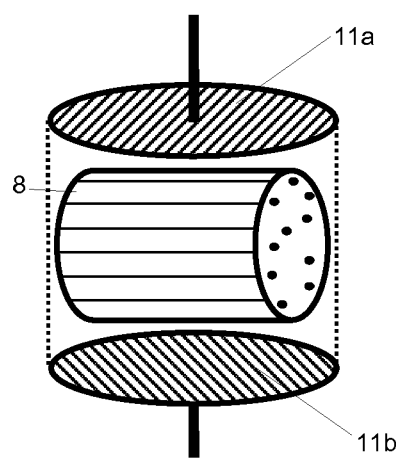
Figure 2:
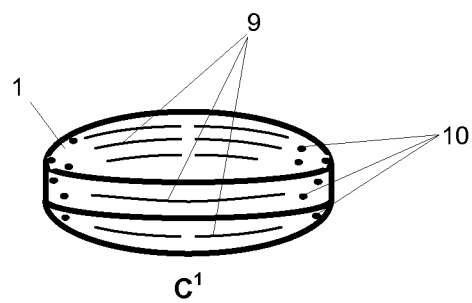
Figure 2:
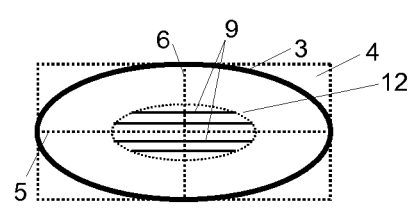
Figure 3:
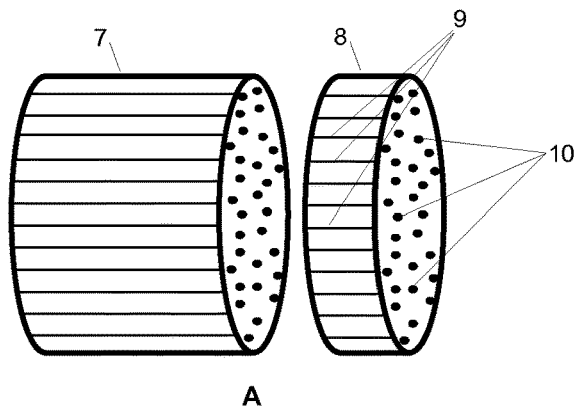
FIG. 3 schematically illustrates the inventive manufacture of oblong hot-melt extruded pharmaceutical dosage forms having an increased breaking strength.
Figure 3:
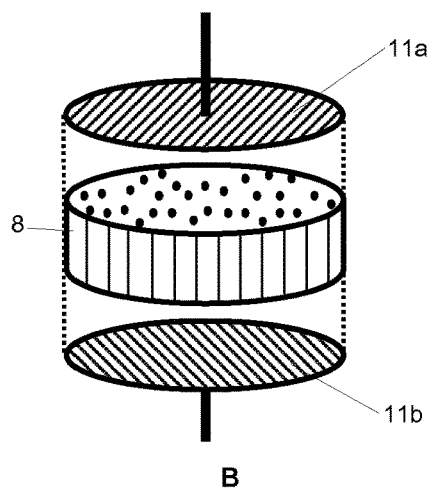
Figure 3:
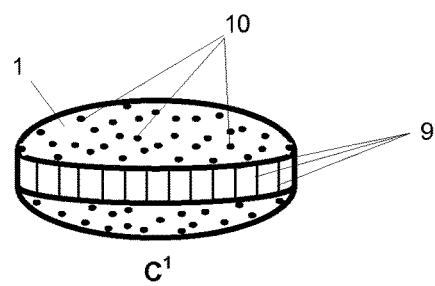
Figure 3:
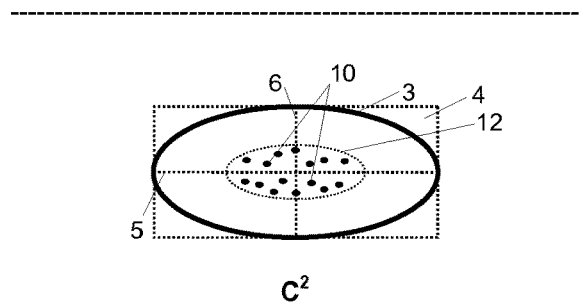

The essential differences of the preparation of conventional oblong dosage forms and inventive oblong dosage forms by hot-melt extrusion are further schematically illustrated in FIGS. 2 and 3.

FIG. 2 schematically illustrates the conventional manufacture of oblong hot-melt extruded pharmaceutical dosage forms having an increased breaking strength.

FIG. 2A shows the extruded strand (7) as well as cylindrical extrudate (8) that has been separated, e.g. cut, to the desired length and weight. The direction of extrusion is indicated by the horizontal lines (9) at the jacket (barrel) of cylindrical extrudate (8) as well as by the spots (10) at the front surfaces. Each spot (10) stands for the end of a horizontal line (9). Horizontal lines (9) as well as spots (10) are indicated for illustration purposes only, as a marker of the direction of extrusion, which can be detected by suitable methods. In reality, however, there are neither horizontal lines (9) nor spots (10). Extruded strand (7) and extrudate (8) have a circular or oblong cross-section, i.e., hot-melt extrusion has been performed through a circular or oblong die.

FIG. 2B shows extrudate (8) in the tabletting tool that is equipped with upper punch (11a) and lower punch (11b). Extrudate (8) is placed into the tabletting tool such that the jacket (barrel) of the extrudate faces upper punch (11a) as well as lower punch (11b). The front surfaces of the extrudate with spots (10), however, do not face any of the punches.

FIG. $2C^1$ shows the resultant conventional tablet (1) as a side view and FIG. $2C^2$ shows the resultant conventional tablet (1) as top view of the cross-section. Plane (4) lies within the body of the pharmaceutical dosage form (1) and includes longitudinal direction of extension (5). The core (12) of the dosage form has a morphological orientation caused by hot-melt extrusion (indicated by horizontal lines (9)) that is substantially parallel to the longitudinal direction of extension (5)

In contrast to FIG. 2 (comparative), FIG. 3 schematically illustrates the manufacture of hot-melt extruded pharmaceutical dosage forms according to the invention.

FIG. 3A shows the extruded strand (7) as well as oblong-cylindrical extrudate (8) that has been separated, e.g. cut, to the desired length and weight. The direction of extrusion is indicated by the horizontal lines (9) at the jacket (barrel) of cylindrical extrudate (8) as well as by the spots (10) at the front surfaces. Each spot (10) stands for the end of a horizontal line (9). Horizontal lines (9) as well as spots (10) are indicated for illustration purposes only, as a marker of the direction of extrusion, which can be detected by suitable methods. In reality, however, there are neither horizontal lines (9) nor spots (10). Extruded strand (7) and extrudate (8) have an oblong cross-section, i.e., hot-melt extrusion has been performed through an oblong die.

FIG. 3B shows extrudate (8) in the tabletting tool that is equipped with upper punch (11a) and lower punch (11b). Extrudate (8) is placed into the tabletting tool such that the front surfaces of the extrudate of oblong shape with spots (10) face upper punch (11a) as well as lower punch (11b). The jacket (barrel) of the extrudate with horizontal lines (9), however, does not face any of the punches.

FIG. $3C^1$ shows the resultant tablet (1) according to the invention as a side view and FIG. $3C^2$ shows the resultant tablet (1) according to the invention as top view of the cross-section. Plane (4) lies within the body of the pharmaceutical dosage form (1) and includes longitudinal direction of extension (5). The core (12) of the dosage form has a morphological orientation caused by hot-melt extrusion (indicated by spots (10)) that is substantially orthogonal (perpendicular) to the longitudinal direction of extension (5).

Figure 4:
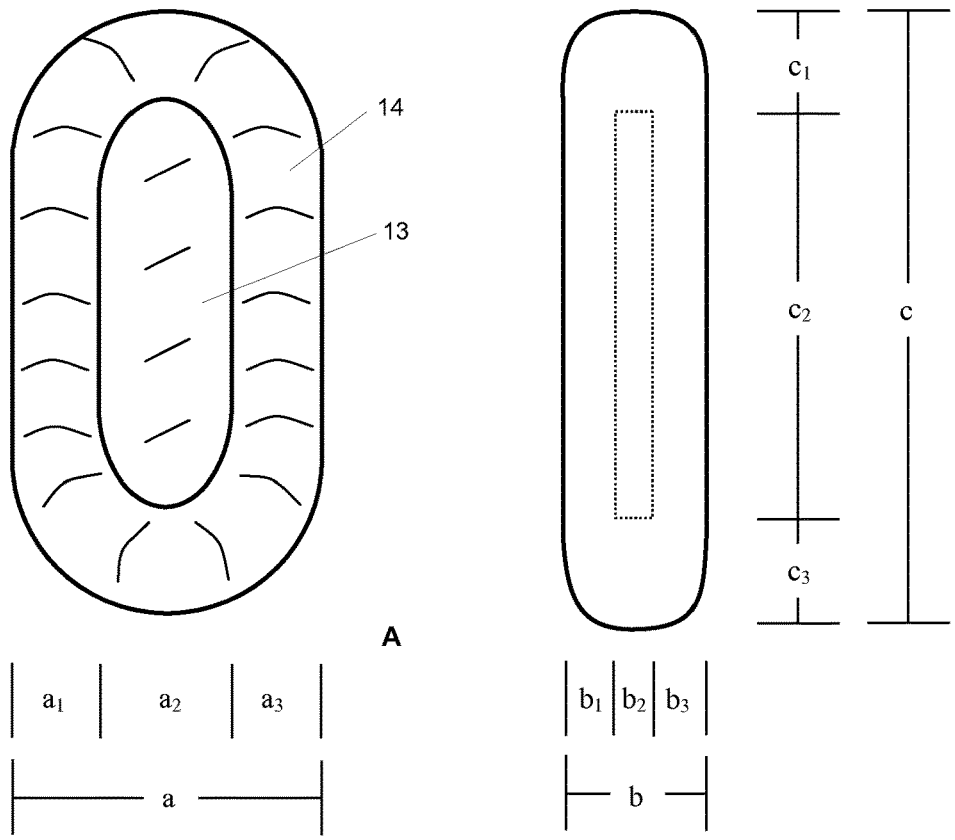
FIG. 4 schematically illustrates a preferred embodiment of the dosage form according to the invention, having two recesses on opposing sides.
Figure 4:
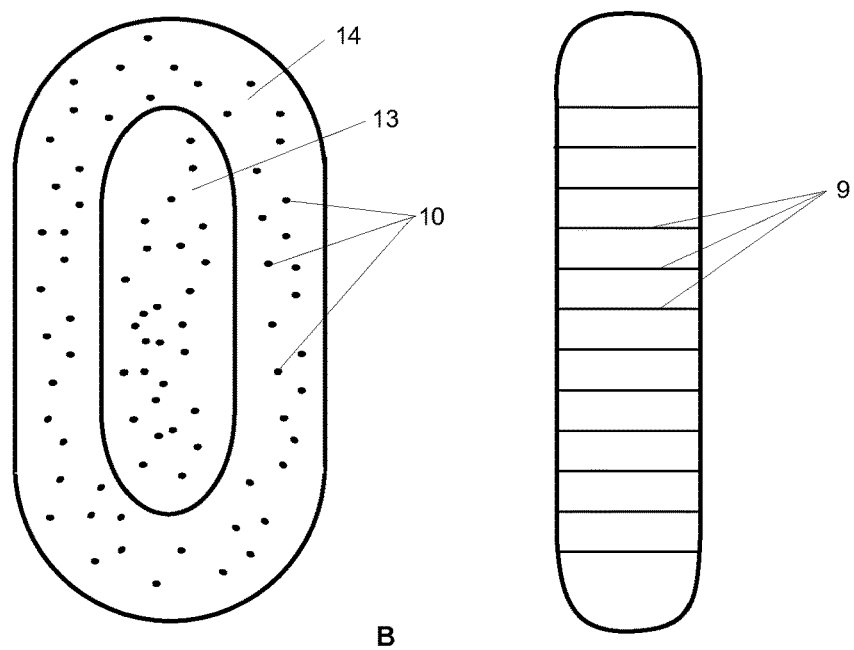

The advantages of the invention become particularly evident when manufacturing H-shaped tablets. H-shaped tablets are formed by means of an H-plunger (H-punch) and are schematically illustrated in FIG. 4. Compared to conventional dosage forms such as biconvex tablets, H-shaped tablets show a different breaking behavior in the breaking strength test.

Further, compared to round tablets, a difference in the orientation of the extrudate could also contribute to the advantages of the dosage form according to the invention. During the tabletting of a round shape the compression force is typically applied by the punches on the cross-section of the extrudate strand, i.e. on its cut surface. During the tabletting of the oblong shape compression force is typically applied rectangular to the cross-section of the extrudate strand, i.e. on its jacket or barrel.

The pharmaceutical dosage form according to the invention is hot-melt extruded.

Hot-melt extruded dosage forms are complex mixtures of active ingredients, functional excipients, and processing aids. Hot-melt extrusion offers several advantages over traditional pharmaceutical processing techniques including the absence of solvents, few processing steps, continuous operation, and the possibility of the formation of solid dispersions and improved bioavailability (cf. M M Crowley et al., Drug Dev Ind Pharm 2007, 33(9), 909-26; and M A Repka et al., ibid, 33(10), 1043-57).

Hot melt-extruded dosage forms can be distinguished from conventional dosage forms, e.g. from other thermoformed dosage forms, due to the morphological orientation caused by the extrusion process. Without intending on being bound to any scientific theory, it is believed that the one-dimensional processing of the hot-melt mass in direction of the extrusion die and the final squeezing therethrough causes morphological orientation processes on molecular and supramolecular level, respectively, that still can be detected in the final dosage form, i.e. even after the extrudate has been further shaped to yield the final dosage form.

Details and preferred embodiments of hot-melt extrusion are described in connection with the methods for preparing the pharmaceutical dosage form according to the invention.

The pharmaceutical dosage form according to the invention has an oblong shape.

For the purpose of the specification, the term "oblong" preferably refers to any three-dimensional body that is longer than high and wide, respectively. The pharmaceutical dosage form according to the invention comprises a longitudinal direction of extension and a transversal direction of extension orthogonal to the longitudinal direction of extension.

The pharmaceutical dosage form according to the invention comprises a cross-sectional area, preferably the main area of extension of the dosage form, including the longitudinal direction of extension as well as the transversal direction of extension, which are orthogonal (perpendicular) to one another.

The main area of extension is preferably the largest cross-sectional area of the pharmaceutical dosage form.

The longitudinal direction of extension is preferably the maximum extension of the dosage form, preferably the maximum end-to-end distance within the main area of extension of the dosage form.

The transversal direction of extension is preferably the maximum extension of the dosage form orthogonal (perpendicular) to the longitudinal direction of extension, preferably within the main area of extension of the dosage form.

The oblong shape of the dosage form can also be expressed in terms of the relative length ratio of the longitudinal direction of extension to the transversal direction of extension. Typically, the longitudinal direction of extension is longer than the transversal direction of extension.

Preferably, the relative length ratio of the longitudinal direction of extension to the transversal direction of extension is at least 1.1:1, at least 1.2:1, at least 1.3:1, at least 1.4:1 or at least 1.5:1; more preferably at least 1.6:1, at least 1.7:1, at least 1.8:1, at least 1.9:1 or at least 2.0:1; still more preferably at least 2.1:1, at least 2.2:1, at least 2.3:1, at least 2.4:1 or at least 2.5:1; yet more preferably at least 2.6:1, most preferably at least 2.7:1 and in particular at least 2.8:1. In a particularly preferred embodiment, the relative length ratio of the longitudinal direction of extension to the transversal direction of extension is 2.6±0.2:1, 2.8±0.2:1 or 3.0±0.2:1.

Preferably, the pharmaceutical dosage form according to the invention comprises a monolithic core. In this regard, monolithic is to be understood as formed or composed of material without joints or seams and constituting a massive undifferentiated and rigid whole. When the dosage form does not comprise a coating, the entire dosage form is preferably monolithic. When the dosage form is film-coated, preferably only the core is monolithic.

The pharmaceutical dosage form according to the invention comprises a front side, an opposite back side and a circumferential rim between said front and back side.

Typically, the pharmaceutical dosage form according to the invention assumes the form of a tablet. The pharmaceutical dosage form is preferably not in film form.

The pharmaceutical dosage form according to the invention may assume various shapes. From top view, the shape of the pharmaceutical dosage form can be any oblong shape such as substantially elliptic, rectangular and the like. Preferably, from side view, the shape of the pharmaceutical dosage form can be substantially flat-convex, biconvex, flat with facet, flat without facet, cyclic, and the like.

In a particularly preferred embodiment, the pharmaceutical dosage form according to the invention can be described as a body having a recess or cavity on at least one side, preferably two recesses or two cavities on two sides, preferably on opposing sides. Alternatively, said cavities and recesses, respectively, may be regarded as bulges, indentations, troughs, hollows, depressions, synclines, deepenings, and the like.

FIG. 4 schematically illustrates a preferred embodiment of such dosage form according to the invention, having two recesses (13) on opposing sides. FIG. 4A illustrates top view and side view also indicating the curvature of the circumference (14) surrounding the recesses (13). FIG. 4B illustrates top view and side view also indicating the direction of extrusion relative to the body of the dosage form, i.e. horizontal lines (9) as well as spots (10).

As the cross-sectional area of the dosage form depicted in FIG. 4 assumes the shape of an H, for the purpose of the specification this shape of dosage form or tablet is also denoted as "H-shaped". For distinguishing purposes, preferred conventional oblong dosage forms are referred to as being "biconvex".

The general shape of the dosage form that are at least related or similar to that one depicted in FIG. 4 can also be described as comprising a longitudinal axis and two opposite longitudinal edges, a transversal axis perpendicular to the longitudinal axis and two opposite transversal edges, a front side, an opposite back side and a circumferential rim between said front and back side, wherein the front side and/or the back side comprise a basis area and wherein the front side and/or the back side comprise at least one bulge which extends above said basis area, said at least one bulge being present at and/or adjacent to at least a section of one or both longitudinal edges and/or at and/or adjacent to at least a section of one or both transversal edges and/or between both longitudinal edges and both transversal edges. The front side and/or the back side of the dosage form, in particular the basis area of the front side and/or the basis area of the back side, can further comprise at least one indentation.

Since the dosage form of the invention has a longitudinal axis being substantially longer than its transversal axis, it exhibits an oblong shape. The longitudinal axis is typically extending through the middle part of the dosage form between both opposing longitudinal edges from one transversal edge to the opposite transversal edge, in particular in such a way that its length is maximized. The transversal axis is typically extending from one longitudinal edge to the opposite longitudinal edge, in particular in such a way that its length is maximized. The transversal axis is oriented perpendicular to the longitudinal axis.

The basis area of the front side and/or the back side of the dosage form of the invention does not necessarily have to be flat, but can in one embodiment exhibit an irregular or regular three dimensional pattern, which, however, is not extending to any significant degree towards the dimension of a bulge or an indentation.

The average distance between the front basis area and the back basis area of one embodiment of the dosage form of the invention usually is smaller than the length of its transversal axis. Those opposite sides of the dosage form which have the smallest average distance usually comprise the front and the back basis areas.

According to another preferred embodiment, a dosage form is provided, wherein the front side and the back side each comprise at least one bulge at least along a section at and/or adjacent to both longitudinal edges and/or at least along a section at and/or adjacent to both transversal edges. In this respect it is even more preferred in certain cases that said front side and said back side comprise an at least essentially continuous bulge at and/or adjacent to at least two third of both opposite longitudinal edges and/or at and/or adjacent to at least two third of both opposite transversal edges.

The bulge may have any geometric cross-section, and can, for example, be rounded or can have a rectangular, triangular or square cross-section. The bulges preferably have a width which is less than half the width, more preferably less than one third of the width of the dosage form. The length of the bulges can vary to a great extent. It is preferred that the overall length of an individual bulge is at least one half of the length of the longitudinal edge or of the transversal edge, depending on its location. Typically, the overall length of a bulge is much longer than its width, e.g. several times the width of the bulge, such as more than 2, 3, 4, 5 or 6 times of its width, in particular when oriented in the longitudinal direction, or more than 2, 3 or 4 times of its width, in particular when oriented in the transversal direction. A bulge in the meaning of the present invention shall also comprise a series of adjacent bulge portions. These bulge portions, when viewed from above, can, for example, have the circumferential form of a circle, an oval, a rectangle, a square, a triangle or any other polygonal form, or may come close to these forms, or may even have an irregular form.

A bulge which is located at a longitudinal and/or at a transversal edge regularly passes over from the circumferential rim of the dosage form without a significant transition zone or transition step, i.e. without a "land". In such an embodiment there is a smooth transition from the rim part to the bulge part so that the outer surfaces of the rim and the bulge form a continuous surface at least over a section. A bulge which is positioned adjacent to a longitudinal or adjacent to a transversal edge is in contrast thereto not directly placed at the circumferential rim of the dosage form but is separated from the rim in the plane of the basis area by a portion, in particular a minor portion, which can be attributed to be part of the basis area. Said minor portion is known in the field of dosage form technology as "the land". This minor area usually has a width being smaller than the average width of the bulge itself. In a preferred embodiment, the land is in the range from about 0.05 mm to about 0.5 mm, e.g. about 0.1 mm.

In a particularly suitable embodiment, the dosage form of the invention is provided with bulges at both longitudinal edges and/or both transversal edges of both the front side and the back side of the dosage form, wherein these bulges extend at least over one half, more preferably over two thirds of the length of the longitudinal and/or transversal edges, even more preferably over the whole length of the longitudinal and/or transversal edges. In another preferred embodiment, the bulges continuously circumscribe the basis area of the front side and/or the back side, preferably the front and the back side, at and/or adjacent to the respective longitudinal and transversal edges. Most desirable results in terms of an improved release profile can for example be obtained with dosage forms of the invention having bulges at both longitudinal edges of both sides of the dosage form. The cross-section of these dosage forms can be described to have or come close to an H-shape. By use of the expression "H-shaped" it shall just be indicated that a dosage form body having opposite, in particular rather flat, basis areas is provided with opposing bulges at the longitudinal edges on both sides of the dosage form body. For example, in one H-shape embodiment the bulges can protrude above their respective basis areas only to a minor extent compared to the lateral distance between the bulges along opposite longitudinal edges, e.g. up to about 1 or 2 mm.

In one preferred embodiment, a dosage form of the invention comprises at or adjacent to, in particular adjacent to, major portions of both opposite longitudinal edges, in particular at least along two thirds of the longitudinal edges, of the front side at least one bulge. In another preferred embodiment, a dosage form of the invention comprises at least one bulge at or adjacent to, in particular adjacent to, major portions of both opposite longitudinal edges, in particular at least along two thirds of the longitudinal edges, of both the front side and the back side of the dosage form. In another preferred embodiment, the dosage form of the invention comprises a circumferential bulge at or adjacent to, in particular adjacent to, the circumferential edge of the front side of said dosage form. In another preferred embodiment, the dosage form of the invention comprises a circumferential bulge at or adjacent to, in particular adjacent to, the circumferential edge of both the front side and the back side of said dosage form.

According to another suitable embodiment of the dosage form of the invention, it is provided that one or both longitudinal edges are essentially straight over at least a major part of their length and/or wherein one or both transversal edges are curved over a major part of their length, in particular curved in the form of an essentially circular arc. It is of course also possible that the longitudinal edges exhibit any other irregular or regular shape, for example, having a wave-like edge portion at least over a section. It is also possible that the transversal edge exhibits the shape of a triangle or any other polygonal shape. In general, both longitudinal and transversal edges form the circumference of the front side and the back side of the dosage form.

For most applications it is sufficient that the longitudinal length, that is, the length of the longitudinal axis, of the dosage form does not exceed 30 mm.

According to another embodiment, the dosage form of the invention preferably has an average thickness over the basis areas of the front and the back side of at least about 1 mm, and in particular of no more than about 9 mm, more in particular ranging from about 1 mm to about 7 mm or more in particular ranging from about 2 mm to about 6 mm.

According to one embodiment of the dosage form of the invention, the bulge extends perpendicular from the basis area of the front side and/or from the basis area of the back side in average from about 0.5 mm to about 2 mm, in particular from about 0.5 mm to about 1 mm.

Dosage forms of the invention preferably have a length in the longitudinal direction in the range of about 5 mm to about 30 mm, in particular in the range of about 15 mm to about 25 mm, more in particular about 17 mm to about 23 mm, even more in particular about 21 mm; a width in the range of about 5 mm to about 15 mm, in particular in the range of about 7 mm to about 12 mm, more in particular about 7 mm to about 10 mm, even more in particular 7 mm, 9 mm or 10 mm; and a thickness over the basis areas in the range of about 1 mm to about 6 mm, in particular in the range of about 1.5 mm to about 4 mm, even more in particular from 2 mm to about 4 mm, even further in particular from about 2.5 mm to about 3.5 mm.

As indicated above, the front side and/or the back side of the dosage form of the invention, in particular the basis area of the front side and/or the basis area of the back side, can in one embodiment further comprise at least one indentation. As has been found, this generally allows for a further improvement of the control of the release profile. The indentation in general in one embodiment represents a hollow space which is provided or embedded in the overall surface of the dosage form. For example, the front side, the back side, in particular the basis areas of the front side and/or the back side, the rim and/or at least one bulge can be provided with at least one indentation.

Indentations, when viewed from above, can have any irregular or regular shape, for example, the form of a square, rectangle, triangle, oval or circle. In one embodiment the indentations can take the form of a cylinder, a cube, a cuboid or a half-sphere, that is the walls and the opening forming the indentation come close to describing the form of a cylinder, a cube, a cuboid or a half-sphere. When viewed from above, the silhouette shape of the indentations has essentially the same width and length dimensions. It is also possible that when viewed from above, the silhouette shape of an indentation has a longer length dimension than a width dimension, for example, a length dimension which is at least 2, 3 or 4 times the width dimension. Accordingly, when viewed from above, the silhouette shape can be rather elongate, e.g. a rectangle, and can have a regular silhouette form, e.g. straight, wave-like, or zig-zag, or can be rather irregular. In another embodiment an array of indentations can be formed, for example on the front side and/or the back side. For many applications it has been found to be sufficient that when viewed from above, the silhouette-shape of the indentation has a length dimension which is essentially identical to its width dimension as, for example, can be found with a circular, square-like or slightly oval or slightly rectangular shape. Said width dimension of the indentations, which is regularly determined parallel to the transversal axis, usually is less than one half of the transversal length of the dosage form, in particular less than one third of the transversal length of the dosage form. In one embodiment the width dimension is essentially identical to the depth of the indentation or is no more than 2 or 3 times the depth of the indentation. The length dimension of the indentation, which is regularly determined parallel to the longitudinal axis, usually is no longer than three quarters of the longitudinal length of the dosage form, in particular no longer than one half of the longitudinal length of the dosage form, and preferably no longer than one third of the longitudinal length of the dosage form. A hole in a dosage form is not an indentation in the meaning of the present invention. The silhouette shape and the depth of said indentations can vary depending on the desired release profile. Usually care should be taken that the depths of these indentations does not come too close to the thickness of the dosage form in order to prevent that upon handling a hole through the dosage form will be formed. Preferably the indentations have a depth which does not go beyond half the thickness of the dosage forms of the invention. For most applications it is frequently already sufficient that the maximum depth of said indentations does not go beyond one third of the thickness of the dosage form of the invention. The average thickness of the dosage form of the invention in general is determined as the distance between the front and back side of the dosage form or preferably between the basis area of the front side and the basis area of the back side.

By using the expressions front side and back side it shall be indicated that the dosage form of the invention has two opposite sides which each can be provided with bulges and/or indentations. In consequence, the selection of which is the front side and which is the back side is rather arbitrary. Accordingly, the expressions front side and back side could also be replaced by first side and opposite second side, respectively.

In one embodiment of the invention, there is provided a dosage form wherein the front side and/or the back side, in particular the, in particular essentially flat, basis area of the front side and/or the, in particular essentially flat, basis area of the back side, comprise in addition to at least one bulge at least one indentation, in particular between opposite longitudinal and/or transversal bulges.

In one embodiment of the invention it is provided that both the front and the back side comprise at least one indentation.

The indentations on the front side and on the back side of the dosage form of the invention can at least once be at least partially off-set or can at least once be positioned in a congruent manner. In one preferred embodiment, all the indentations of the front side and all indentations on the back side are at least partially off-set or are positioned in a congruent manner.

The indentations are regularly positioned in the base area of the front and/or the back side of the dosage form of the invention. It is for example possible to place two or more of such indentations adjacent to each other, e.g. in a row located between the longitudinal edges of the front and/or the back side. The indentations are preferably located between opposite longitudinally extending bulges at or adjacent to the longitudinal edges of the front and/or the back side of the dosage form of the invention.

In one preferred embodiment, a dosage form of the invention, in particular its oblong form, comprises at or adjacent to, in particular adjacent to, major portions of both longitudinal edges, in particular at least along two thirds of the longitudinal edges of the front side at least one bulge, and, in particular between the bulges along opposite longitudinal edges, at least one indentation.

In another preferred embodiment, a dosage form of the invention, in particular its oblong form, comprises at least one bulge at or adjacent to, in particular adjacent to, major portions of both opposite longitudinal edges, in particular at least along two thirds of the longitudinal edges of both the front side and the back side of the dosage form as well as at least one indentation on the front side and/or the back side, in particular on the basis area of the front side and/or the basis of the back side, of the dosage form, in particular between the bulges which are located along opposite longitudinal edges on the front side and/or the back side, respectively. In another preferred embodiment, the dosage form of the invention, in particular its oblong form, comprises a circumferential bulge at or adjacent to, in particular adjacent to, the circumferential edge of the front side and/or back side of said dosage form, and at least one indentation on the front side and/or back side, in particular on the basis area circumscribed by the circumferential bulge on the front and/or on the back side. In another preferred embodiment, the dosage form of the invention, in particular its oblong form, comprises a circumferential bulge at or adjacent to, in particular adjacent to, the circumferential edge of both the front side and the back side of said dosage form and at least one indentation on the front side and the back side, in particular on the basis area circumscribed by the circumferential bulge of the front side and on the basis area circumscribed by the circumferential bulge of the back side.

In the Cartesian space, the principal dimensions of the pharmaceutical dosage form schematically illustrated in FIG. 4 can be defined as a, b and c, where $a=a_1+a_2+a_3$, $b=b_1+b_2+b_3$ and $c=c_1+c_2+c_3$. Preferred relative dimensions D1 to D6 of the pharmaceutical dosage form depicted in FIG. 4 can be defined in relative relations of a, b and c; $a_1$, $a_2$ and $a_3$; $b_1$, $b_2$ and $b_3$; and $c_1$, $c_2$ and $c_3$, respectively:

D1: $c>a\geq b$; $c>a>b$;

D2: $c>1.5\,a$; $c>2\,a$; $c>2.5\,a$; $c>3\,a$;

D3: $a_2>a_1\cong a_3$; $a_2>1.1\,a_1\cong 1.1\,a_3$; $a_2>1.2\,a_1\cong 1.2\,a_3$; $a_2>1.3\,a_1\cong 1.3\,a_3$;

D4: $b_2\geq b_1\cong b_3$; $b_2\geq 1.1\,b_1\cong 1.1\,b_3$; $b_2\geq 1.2\,b_1\cong 1.2\,b_3$; $b_2\geq 1.3\,b_1\cong 1.3\,b_3$;

D5: $b_2\leq b_1\cong b_3$; $b_2\leq 0.9\,b_1\cong 0.9\,b_3$; $b_2\leq 0.8\,b_1\cong 0.8\,b_3$; $b_2\leq 0.7\,b_1\cong 0.7\,b_3$; and/or D6: $c_2>c_1\cong c_2$; $c_2>1.1\,c_1\cong 1.1\,c_3$; $c_2>1.2\,c_1\cong 1.2\,c_3$; $c_2>1.3\,c_1\cong 1.3\,c_3$.

Preferred embodiments D7 to D18 regarding the absolute dimensions of the pharmaceutical dosage form depicted in FIG. 4 are displayed in the table here below:

| [mm] | D7 | D8 | D9 | D10 | D11 | D12 |
|---|---|---|---|---|---|---|
| a | 8.6 ± 4.3 | 8.6 ± 2.1 | 8.6 ± 1.0 | 9.0 ± 4.5 | 9.0 ± 2.2 | 9.0 ± 1.1 |
| b | 4.9 ± 2.5 | 4.9 ± 1.3 | 4.9 ± 0.7 | 4.3 ± 2.1 | 4.3 ± 1.0 | 4.3 ± 0.6 |
| c | 21.9 ± 11.0 | 21.9 ± 5.5 | 21.9 ± 2.7 | 20.4 ± 10.2 | 20.4 ± 5.1 | 20.4 ± 2.5 |

| [mm] | D13 | D14 | D15 | D16 | D17 | D18 |
|---|---|---|---|---|---|---|
| a | 9.0 ± 4.3 | 9.0 ± 2.1 | 9.0 ± 1.0 | 9.1 ± 4.5 | 9.1 ± 2.2 | 9.1 ± 1.1 |
| b | 4.1 ± 2.5 | 4.1 ± 1.3 | 4.1 ± 0.7 | 4.5 ± 2.1 | 4.5 ± 1.0 | 4.5 ± 0.6 |
| c | 20.5 ± 11.0 | 20.5 ± 5.5 | 20.5 ± 2.7 | 20.5 ± 10.2 | 20.5 ± 5.1 | 20.5 ± 2.5 |

Preferred embodiments D19 to D30 regarding the absolute dimensions of the pharmaceutical dosage form depicted in FIG. 4 are displayed in the table here below:

| [mm] | | D19 | D20 | D21 | D22 | D23 | D24 |
|---|---|---|---|---|---|---|---|
| a | | 8.6 ± 4.3 | 8.6 ± 2.1 | 8.6 ± 1.0 | 9.0 ± 4.5 | 9.0 ± 2.2 | 9.0 ± 1.1 |
| | $a_1$ | 3.3 ± 1.6 | 3.3 ± 0.8 | 3.3 ± 0.4 | 3.5 ± 1.8 | 3.5 ± 0.9 | 3.5 ± 0.5 |
| | $a_2$ | 2.1 ± 1.0 | 2.1 ± 0.5 | 2.1 ± 0.3 | 2.1 ± 1.1 | 2.1 ± 0.6 | 2.1 ± 0.3 |
| | $a_3$ | 3.3 ± 1.6 | 3.3 ± 0.8 | 3.3 ± 0.4 | 3.5 ± 1.8 | 3.5 ± 0.9 | 3.5 ± 0.5 |
| b | | 4.9 ± 2.5 | 4.9 ± 1.3 | 4.9 ± 0.7 | 4.3 ± 2.1 | 4.3 ± 1.0 | 4.3 ± 0.6 |
| | $b_1$ | 0.9 ± 0.5 | 0.9 ± 0.3 | 0.9 ± 0.2 | 0.9 ± 0.4 | 0.9 ± 0.2 | 0.9 ± 0.1 |
| | $b_2$ | 3.1 ± 1.5 | 3.1 ± 0.7 | 3.1 ± 0.4 | 2.6 ± 1.3 | 2.6 ± 0.6 | 2.6 ± 0.3 |
| | $b_3$ | 0.9 ± 0.5 | 0.9 ± 0.3 | 0.9 ± 0.2 | 0.9 ± 0.4 | 0.9 ± 0.2 | 0.9 ± 0.1 |
| c | | 21.9 ± 11.0 | 21.9 ± 5.5 | 21.9 ± 2.7 | 20.4 ± 10.2 | 20.4 ± 5.1 | 20.4 ± 2.5 |
| | $c_1$ | 3.2 ± 1.6 | 3.2 ± 0.8 | 3.2 ± 0.4 | 3.3 ± 1.7 | 3.3 ± 0.9 | 3.3 ± 0.4 |
| | $c_2$ | 15.6 ± 7.8 | 15.6 ± 3.9 | 15.6 ± 2.0 | 13.8 ± 6.9 | 13.8 ± 3.5 | 13.8 ± 1.7 |
| | $c_3$ | 3.2 ± 1.6 | 3.2 ± 0.8 | 3.2 ± 0.4 | 3.3 ± 1.7 | 3.3 ± 0.9 | 3.3 ± 0.4 |

| [mm] | | D25 | D26 | D27 | D28 | D29 | D30 |
|---|---|---|---|---|---|---|---|
| a | | 9.0 ± 4.3 | 9.0 ± 2.1 | 9.0 ± 1.0 | 9.1 ± 4.5 | 9.1 ± 2.2 | 9.1 ± 1.1 |
| | $a_1$ | 3.2 ± 1.6 | 3.2 ± 0.8 | 3.2 ± 0.4 | 3.2 ± 1.8 | 3.2 ± 0.9 | 3.2 ± 0.5 |
| | $a_2$ | 2.6 ± 1.0 | 2.6 ± 0.5 | 2.6 ± 0.3 | 2.7 ± 1.1 | 2.7 ± 0.6 | 2.7 ± 0.3 |
| | $a_3$ | 3.2 ± 1.6 | 3.2 ± 0.8 | 3.2 ± 0.4 | 3.2 ± 1.8 | 3.2 ± 0.9 | 3.2 ± 0.5 |
| b | | 4.1 ± 2.5 | 4.1 ± 1.3 | 4.1 ± 0.7 | 4.5 ± 2.1 | 4.5 ± 1.0 | 4.5 ± 0.6 |
| | $b_1$ | 1.0 ± 0.5 | 1.0 ± 0.3 | 1.0 ± 0.2 | 1.0 ± 0.4 | 1.0 ± 0.2 | 1.0 ± 0.1 |
| | $b_2$ | 2.1 ± 1.5 | 2.1 ± 0.7 | 2.1 ± 0.4 | 2.5 ± 1.3 | 2.5 ± 0.6 | 2.5 ± 0.3 |
| | $b_3$ | 1.0 ± 0.5 | 1.0 ± 0.3 | 1.0 ± 0.2 | 1.0 ± 0.4 | 1.0 ± 0.2 | 1.0 ± 0.1 |
| c | | 20.5 ± 11.0 | 20.5 ± 5.5 | 20.5 ± 2.7 | 20.5 ± 10.2 | 20.5 ± 5.1 | 20.5 ± 2.5 |
| | $c_1$ | 3.3 ± 1.6 | 3.3 ± 0.8 | 3.3 ± 0.4 | 3.3 ± 1.7 | 3.3 ± 0.9 | 3.3 ± 0.4 |
| | $c_2$ | 13.9 ± 7.8 | 13.9 ± 3.9 | 13.9 ± 2.0 | 13.9 ± 6.9 | 13.9 ± 3.5 | 13.9 ± 1.7 |
| | $c_3$ | 3.3 ± 1.6 | 3.3 ± 0.8 | 3.3 ± 0.4 | 3.3 ± 1.7 | 3.3 ± 0.9 | 3.3 ± 0.4 |

The pharmaceutical dosage form is preferably adapted for oral administration, i.e., should be capable of being swallowed. Thus, obscure geometrical forms which are obviously harmful cannot be regarded as pharmaceutical dosage forms according to the invention.

According to a preferred embodiment, the pharmaceutical dosage form is characterized by a specific aspect ratio. For the purpose of the specification, the aspect ratio is defined as the ratio of the main direction of extension of the dosage form to the maximum extension of the pharmaceutical dosage form orthogonal to said main direction of extension, e.g. maximum length to maximum height (and maximum length to maximum width, respectively).

Preferably, said aspect ratio is within the range of 2.4±1.3:1, more preferably 2.4±1.0:1, still more preferably 2.4±0.8:1, yet more preferably 2.4±0.6:1, most preferably 2.4±0.4:1 and in particular 2.4±0.2:1.

According to a preferred embodiment, the pharmaceutical dosage form is characterized by a specific length to height to width ratio, where length>height≥width. For the purpose of the specification, in this embodiment the length corresponds to the longitudinal direction of extension of the dosage form, the height corresponds to the maximum extension of the pharmaceutical dosage form orthogonal to the length, and the width corresponds to the transversal direction of extension orthogonal to the length and orthogonal to the width (Cartesian space). Preferably, the length to height to width ratio is within the range of 4.7±2.0:2.0±1.0:1, more preferably 4.7±1.6:2.0±0.8:1, still more preferably 4.7±1.2:2.0±0.6:1, yet more preferably 4.7±0.8:2.0±0.4:1, most preferably 4.7±0.6:2.0±0.3:1, and in particular 4.7±0.4:2.0±0.2:1.

Preferably, a portion of the surface of the pharmaceutical dosage form is convex, i.e. curved out or bulged outward, and another portion of its surface is concave, i.e. curved in or hollowed inward. For the purpose of the specification, the radius of curvature is not critical.

Preferably, the overall surface of the pharmaceutical dosage form can be divided into concave portions, convex portions and planar portions. Typically, the sum of the concave portions, convex portions and planar portions corresponds to the overall surface of the dosage form. However, at least theoretically, a given portion can be convex and concave simultaneously (saddle). Under these circumstances, the sum of the concave portions, convex portions and planar portions exceeds the overall surface of the dosage form.

In a preferred embodiment, the convex portion of the surface of the dosage form is at most 95%, more preferably at most 90% or at most 85%, still more preferably at most 80% or at most 75%, yet more preferably at most 70% or at most 65%, most preferably at most 60% or at most 55% and on particular at most 50% or at most 45%, based on the sum of concave portions, convex portions and planar portions.

In another preferred embodiment, the concave portion of the surface of the dosage form is at least 5%, more preferably at least 10% or at least 15%, still more preferably at least 20% or at least 25%, yet more preferably at least 30% or at least 35%, most preferably at least 40% or at least 45% and in particular at least 50% or at least 55%, based on the sum of concave portions, convex portions and planar portions.

In a preferred embodiment of the pharmaceutical dosage form according to the invention, the maximum extension of the dosage form orthogonal to the main area of extension of the dosage form is spaced from the centre of mass of the dosage form parallel to said main area of extension. For the purpose of the specification, the main area of extension of the dosage form is preferably the largest plain area that can be placed along a cut of the body of the dosage form. Preferably, the closest distance from the maximum extension of the dosage form orthogonal to the main area of extension of the dosage form to the centre of mass of the dosage form is at least 0.5 mm, more preferably at least 1.0 mm, still more preferably at least 1.5 mm, yet more preferably at least 2.0 mm, most preferably at least 2.5 mm and in particular at least 3.0 mm.

In a preferred embodiment, the cross sectional area of the pharmaceutical dosage form that is orthogonal to the longitudinal direction of extension and that contains the centre of mass of the dosage form has a shape so that at least 50%, more preferably at least 60% and in particular at least 75% of its area is spaced at least 0.2 mm, at least 0.3 mm, at least 0.4 mm or at least 0.5 mm, more preferably at least 0.6 mm, at least 0.7 mm, at least 0.8 mm or at least 0.9 mm, still more preferably at least 1.0 mm, at least 1.1 mm, at least 1.2 mm or at least 1.3 mm, yet more preferably at least 1.4 mm, at least 1.5 mm, at least 1.6 mm or at least 1.7 mm, most preferably at least 1.8 mm, at least 1.9 mm, at least 2.0 mm or at least 2.1 mm and in particular at least 2.2 mm, at least 2.3 mm, at least 2.4 mm or at least 2.5 mm from the centre of mass. Preferably, said cross sectional area contains the centre of mass.

In a preferred embodiment of the pharmaceutical dosage form according to the invention, the closest distance of each and every geometrical point within the dosage form to the surface of the dosage form is at most 10 mm, at most 9 mm, at most 8 mm or at most 7.5 mm; more preferably at most 7.0 mm, at most 6.5 mm or at most 6.0 mm; still more preferably at most 5.8 mm, at most 5.6 mm, at most 5.4 mm, at most 5.2 mm or at most 5.0 mm; yet more preferably at most 4.8 mm, at most 4.6 mm, at most 4.4 mm, at most 4.2 mm or at most 4.0 mm; yet more preferably at most 3.8 mm, at most 3.6 mm, at most 3.4 mm, at most 3.2 mm or at most 3.0 mm; most preferably at most 2.8 mm, at most 2.6 mm, at most 2.4 mm, at most 2.2 mm or at most 2.0 mm; and in particular at most 1.8 mm, at most 1.6 mm, at most 1.4 mm, at most 1.2 mm or at most 1.0 mm.

In a preferred embodiment, the centre of mass of the pharmaceutical dosage form lies within the main area of extension of the dosage form. Preferably, the pharmaceutical dosage form is symmetric about its main area of extension.

In a preferred embodiment, the surface S [mm$^2$] to weight W [mg] ratio S/W of the pharmaceutical dosage form according to the invention is at least 0.50 mm$^2$/mg. Preferably, S/W is at least 0.51, at least 0.52, at least 0.53, at least 0.54 or at least 0.55; more preferably at least 0.56, at least 0.57, at least 0.58, at least 0.59 or at least 0.60; still more preferably at least 0.61, at least 0.62, at least 0.63, at least 0.64 or at least 0.65; yet more preferably at least 0.66, at least 0.67, at least 0.68, at least 0.69 or at least 0.70; most preferably at least 0.705, at least 0.710, at least 0.715, at least 0.720, at least 0.725, at least 0.730, at least 0.735, at least 0.740, at least 0.745 or at least 0.750; and in particular at least 0.755, at least 0.760, at least 0.765, at least 0.770, at least 0.775, at least 0.780, at least 0.785, at least 0.790, at least 0.795 or at least 0.80 mm$^2$/mg. In another preferred embodiment, the surface S [mm$^2$] to weight W [mg] ratio S/W of the pharmaceutical dosage form according to the invention is at least 0.80 mm$^2$/mg. Preferably, S/W is at least 0.81, at least 0.82, at least 0.83, at least 0.84 or at least 0.85; more preferably at least 0.86, at least 0.87, at least 0.88, at least 0.89 or at least 0.90; still more preferably at least 0.91, at least 0.92, at least 0.93, at least 0.94 or at least 0.95; yet more preferably at least 0.96, at least 0.97, at least 0.98, at least 0.99 or at least 1.00; most preferably at least 1.05, at least 1.10, at least 1.15, at least 1.20, at least 1.25, at least 1.30, at least 1.35, at least 1.40, at least 1.45 or at least 1.50; and in particular at least 1.55, at least 1.60, at least 1.65, at least 1.70, or at least 1.75 mm²/mg.

In a preferred embodiment, the pharmaceutical dosage form according to the invention has a total surface S defined by the formula $$S \geq A \cdot W^{2/3},$$

wherein A is at least 4.5, i.e. $S \geq 4.5 \cdot W^{2/3}$.

For example, when the pharmaceutical dosage form according to the invention has a total weight of 623 mg, its total surface S is preferably at least 328 mm² ($4.5 \cdot 623^{2/3}$) and when the pharmaceutical dosage form according to the invention has a total weight of 983 mg, its total surface S is preferably at least 445 mm² ($4.5 \cdot 983^{2/3}$).

Methods for measuring the total surface of a pharmaceutical dosage form are known to the skilled artisan. For example, the total surface may be calculated from the three dimensional extension of the pharmaceutical dosage form based on simple geometrical considerations (cf., e.g., Eudragit® Application Guidelines, 10th edition, 07/2007, Röhm GmbH, Darmstadt).

In approximation, the pharmaceutical dosage form may also be mentally divided into a plurality of identical cubic volume elements of suitable size (voxels) and the total surface may be determined by counting the squared area elements (pixels) being located at the surface.

Preferably, when measuring the total surface of the pharmaceutical dosage form, the micro-fine structure of the pharmacologically active compound (A) and of all other constituents of the dosage form including polymers and pharmaceutical excipients, e.g. their porosity, is not taken into account. For the purpose of the specification, the term "surface" of the pharmaceutical dosage form preferably refers to the macroscopic surface (outer dimensions, silhouette). In other words, for the purpose of determining the surface of the pharmaceutical dosage form, the surface structure is preferably considered perfectly smooth.

In a preferred embodiment of the pharmaceutical dosage form according to the invention, A is 4.6, 4.7, 4.8, 4.9, 5.0, 5.1, 5.2, 5.3, 5.4, 5.5, 5.6, 5.7, 5.8, 5.9 or 6.0; more preferably 6.05, 6.1, 6.15, 6.2, 6.25, 6.3, 6.35, 6.4, 6.45, 6.5, 6.55, 6.6, 6.65, 6.7, 6.75, 6.8, 6.85, 6.9, 6.95, 7.0, 7.05, 7.1, 7.15, 7.2, 7.25, 7.3, 7.35, 7.4, 7.45 or 7.5.

In another preferred embodiment of the pharmaceutical dosage form according to the invention, A is 7.6, 7.7, 7.8, 7.9, 8.0, 8.1, 8.2, 8.3, 8.4, 8.5, 8.6, 8.7, 8.8, 8.9 or 9.0; more preferably 9.1, 9.2, 9.3, 9.4, 9.5, 9.6, 9.7, 9.8, 9.9, 10.0, 10.1, 10.2, 10.3, 10.4 or 10.5; most preferably 10.6, 10.7, 10.8, 10.9, 11.0, 11.1, 11.2, 11.3, 11.4, 11.5, 11.6, 11.7, 11.8, 11.9 or 12.0; and in particular 12.1, 12.2, 12.3, 12.4, 12.5, 12.6, 12.7, 12.8, 12.9, 13.0, 13.1, 13.2, 13.3, 13.4 or 13.5.

In a preferred embodiment, the total surface S of the pharmaceutical dosage form according to the invention satisfies the following requirement $$B \cdot W^{\frac{2}{3}} \geq S \geq A \cdot W^{\frac{2}{3}}$$

where
  A and W are defined as above and
  B is at most 20, more preferably at most 19, still more preferably at most 18, yet more preferably at most 17, most preferably at most 16 and in particular at most 15.

In a preferred embodiment, the total surface S of the pharmaceutical dosage form according to the invention is at least 50 mm², at least 75 mm², at least 100 mm², at least 125 mm², at least 150 mm², at least 175 mm² or at least 200 mm²; more preferably at least 225 mm², at least 250 mm², at least 275 mm², at least 300 mm², at least 325 mm², at least 350 mm², at least 375 mm² or at least 400 mm²; still more preferably at least 425 mm², at least 450 mm², at least 475 mm², at least 500 mm², at least 525 mm²; at least 550 mm², at least 575 mm² or at least 600 mm²; yet more preferably at least 625 mm², at least 650 mm², at least 675 mm², at least 700 mm², at least 725 mm², at least 750 mm², at least 775 mm² or at least 800 mm²; most preferably at least 825 mm², at least 850 mm², at least 875 mm², at least 900 mm², at least 925 mm², at least 950 mm², at least 975 mm² or at least 1000 mm²; and in particular at least 1025 mm², at least 1050 mm², at least 1075 mm², at least 1100 mm², at least 1125 mm², at least 1150 mm², at least 1175 mm² or at least 1200 mm².

In a preferred embodiment, the total surface S of the pharmaceutical dosage form according to the invention is at most 1500 mm², more preferably at most 1400 mm², still more preferably at most 1300 mm², yet more preferably at most 1200 mm², most preferably at most 1100 mm², and in particular at most 1000 mm².

In a preferred embodiment, at least 35% of the outer surface of the pharmaceutical dosage form according to the invention originates from cut surfaces of the extrudate, whereas the remainder originates from the jacket (barrel) of the extrudate. Preferably, at least 40% or at least 45%, more preferably at least 50% or at least 55%, still more preferably at least 60% or at least 65%, yet more preferably at least 70% or at least 72.5%, most preferably at least 75% or at least 77.5% and in particular at least 80% or at least 82.5% of the outer surface of the pharmaceutical dosage form according to the invention originates from cut surfaces of the extrudate.

In a preferred embodiment the pharmaceutical dosage form according to the invention is manufactured, particularly shaped, by means of a so-called H-plunger. The silhouette of a dosage form obtainable by means of such a H-plunger is schematically illustrated in FIG. 4. H-plungers of suitable size and shape are commercially available. Typically, the volume and the surface of the dosage forms that are obtainable by a given H-plunger can be calculated with a formula usually provided by the manufacturer of the H-plunger.

For example, Notter GmbH, Germany offers a H-plunger forming a volume of 94.3+171.6 h [mm³] and a surface of 382+52.3 h [mm²], where h is the height of the dosage form (corresponding to distance $b_2$ in FIG. 4). Therefore, for example, when shaping 650 mg of a compacted composition having an overall density of 1.000 mg/mm³ with such H-plunger, a dosage form is obtained having a height of h=(650−94.3)/171.6=3.24 mm. Thus, said dosage form has a surface of 382+52.3·3.24=551 mm². When A=4.5, the requirement of 551 mm²≥4.5 650²/³ (=337.6 mm²) is satisfied. When A is about 7.3, the requirement of 551 mm²≥7.3 650²/³ (=547 mm²) is still satisfied, but when A is 7.4, the requirement 551 mm²≥7.4 650²/³ (=555 mm²) is not satisfied.

In a preferred embodiment, the pharmaceutical dosage form according to the invention has a total weight W of at least 50 mg, at least 75 mg, at least 100 mg, at least 125 mg or at least 150 mg; more preferably at least 175 mg, at least 200 mg, at least 225 mg, at least 250 mg or at least 275 mg; still more preferably at least 300 mg, at least 325 mg, at least 350 mg, at least 375 mg or at least 400 mg; yet more preferably at least 425 mg, at least 450 mg, at least 475 mg, at least 500 mg or at least 525 mg; most preferably at least 550 mg, at least 575 mg, at least 600 mg, at least 625 mg or at least 650 mg; and in particular at least 675 mg, at least 700 mg, at least 725 mg, at least 750 mg or at least 775 mg. Preferably, the total weight of the pharmaceutical dosage form according to the invention is within the range from 0.01 g to 1.5 g, more preferably 0.05 g to 1.2 g, still more preferably 0.1 g to 1.0 g, most preferably 0.2 g to 0.9 g and in particular 0.25 g to 0.8 g.

In a preferred embodiment, the core of the pharmaceutical dosage form according to the invention has a morphological orientation caused by hot-melt extrusion that is substantially orthogonal to the longitudinal direction of extension of the dosage form.

In this regard, "substantially" means that the angle may somewhat deviate from 90.0°. Preferably, the angle is within the range of 90±30°, more preferably 90±25°, still more preferably 90±20°, yet more preferably 90±15°, most preferably 90±10°, and in particular 90±5°.

Analytical methods to determine the morphological orientation caused by hot-melt extrusion are known to the person skilled in the art such as electron microscopy, atomic force spectroscopy and the like. Another suitable method is the three-dimensional terahertz spectroscopy, e.g., terahertz time-domain spectroscopy (THz-TDS) (cf. e.g. S. L. Dexheimer, Terahertz Spectroscopy Principles and Applications (Optical Science and Engineering Series), CRC; 1 edition 2007; R. E. Miles et al., Terahertz Frequency Detection and Identification of Materials and Objects (NATO Science for Peace and Security Series B: Physics and Biophysics), Springer; 1 edition 2007; and Y.-S. Lee et al., Principles of Terahertz Science and Technology (Lecture Notes in Physics), Springer; 1 edition 2008).

Figure 5:
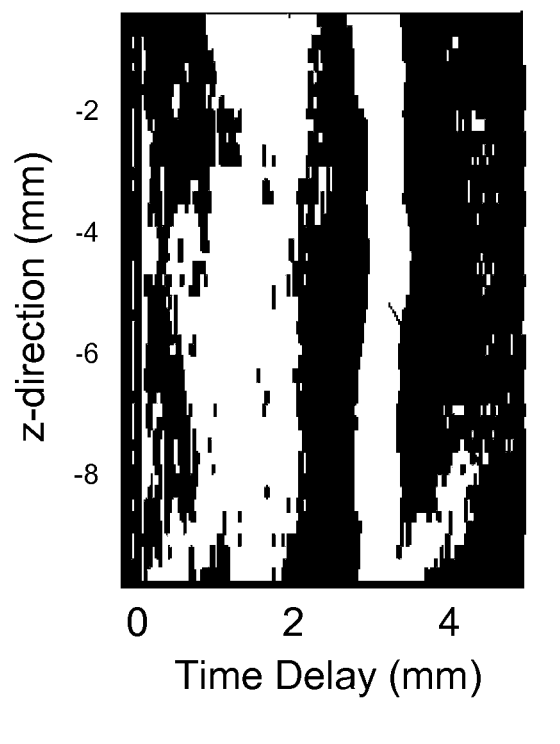
FIG. 5 shows the result of a three dimensional terahertz measurement.
Figure 5:
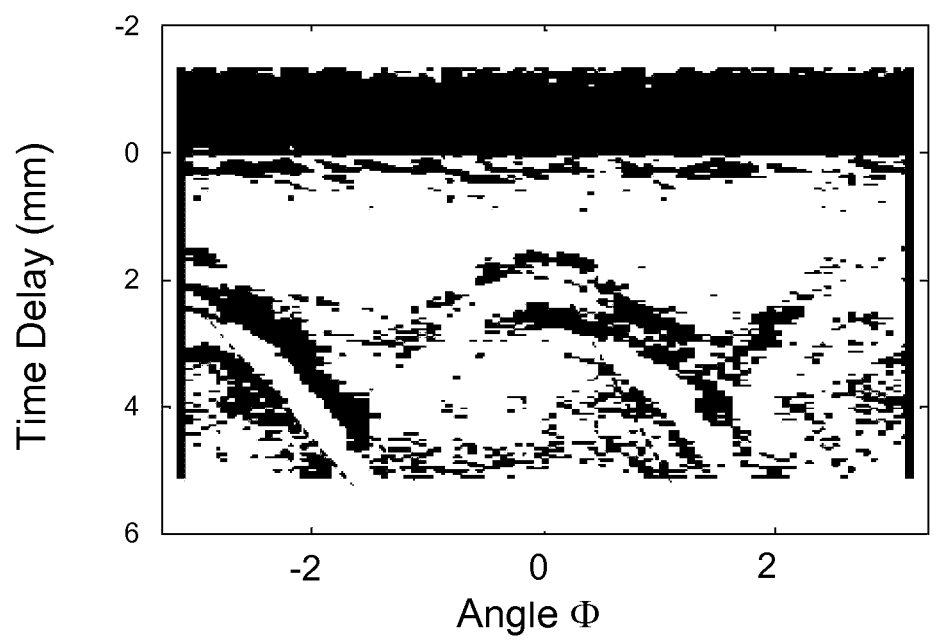

FIG. 5A illustrates how the morphological orientation of an extrudate can be visualized by means of terahertz spectroscopy. FIG. 5B illustrates that said morphological orientation can still be visualized after press-forming said extrudate, e.g. into tablets having a different outer shape.

Preferably, the core of the pharmaceutical dosage form according to the invention has a morphological orientation caused by hot-melt extrusion that is not only substantially orthogonal (perpendicular) to the longitudinal direction of extension of the dosage form, but additionally substantially orthogonal (perpendicular) to the transversal direction of extension of the dosage form.

In this regard, "substantially" also means that the angle may somewhat deviate from 90.0°. Preferably, the angle is within the range of 90±30°, more preferably 90±25°, still more preferably 90±20°, yet more preferably 90±15°, most preferably 90±10°, and in particular 90±5°.

In a preferred embodiment the pharmaceutical dosage form according to the invention has an overall density of at least 0.80 or at least 0.85 g/cm$^3$, more preferably at least 0.90 or at least 0.95 g/cm$^3$, still more preferably at least 1.00, at least 1.05 or at least 1.10 g/cm$^3$, most preferably in the range from 0.80 to 1.35 g/cm$^3$, and in particular in the range from 0.95 to 1.25 g/cm$^3$.

In a preferred embodiment, the pharmaceutical dosage form according to the invention has an overall density within the range of 1.00±0.30 g/cm$^3$, more preferably 1.00±0.25 g/cm$^3$, still more preferably 1.00±0.20 g/cm$^3$, yet more preferably 1.00±0.15 g/cm$^3$, most preferably 1.00±0.10 g/cm$^3$, and in particular 1.00±0.05 g/cm$^3$. In another preferred embodiment, the pharmaceutical dosage form according to the invention has an overall density within the range of 1.10±0.30 g/cm$^3$, more preferably 1.10±0.25 g/cm$^3$, still more preferably 1.10±0.20 g/cm$^3$, yet more preferably 1.10±0.15 g/cm$^3$, most preferably 1.10±0.10 g/cm$^3$, and in particular 1.10±0.05 g/cm$^3$. In still another preferred embodiment, the pharmaceutical dosage form according to the invention has an overall density within the range of 1.20±0.30 g/cm$^3$, more preferably 1.20±0.25 g/cm$^3$, still more preferably 1.20±0.20 g/cm$^3$, yet more preferably 1.20±0.15 g/cm$^3$, most preferably 1.20±0.10 g/cm$^3$, and in particular 1.20±0.05 g/cm$^3$.

Preferably, the overall density of the pharmaceutical dosage form according to the invention is 1.00±0.02 g/cm$^3$, 1.02±0.02 g/cm$^3$, 1.04±0.02 g/cm$^3$, 1.06±0.02 g/cm$^3$, 1.08±0.02 g/cm$^3$, 1.10±0.02 g/cm$^3$, 1.12±0.02 g/cm$^3$, 1.14±0.02 g/cm$^3$, 1.16±0.02 g/cm$^3$, 1.18±0.02 g/cm$^3$, 1.20±0.02 g/cm$^3$, 1.22±0.02 g/cm$^3$, 1.24±0.02 g/cm$^3$, 1.26±0.02 g/cm$^3$, 1.28±0.02 g/cm$^3$, 1.30±0.02 g/cm$^3$, 1.32±0.02 g/cm$^3$, 1.34±0.02 g/cm$^3$, 1.36±0.02 g/cm$^3$, 1.38±0.02 g/cm$^3$, or 1.40±0.02 g/cm$^3$.

Preferably, the pharmaceutical dosage form according to the invention is characterized by a comparatively homogeneous distribution of density. Preferably, the densities of two segments of the pharmaceutical dosage form having a volume of 1.0 mm$^3$ each, deviate from one another by not more than ±10%, more preferably not more than more than ±7.5%, still more preferably not more than ±5.0%, most preferably not more than ±2.5%, and in particular not more than ±1.0%. When the pharmaceutical dosage form is film coated, said two segments of the pharmaceutical dosage form having a volume of 1.0 mm$^3$ each are preferably segments of the core, i.e. do not contain any coating material.

The pharmaceutical dosage form according to the invention shows controlled release of the pharmacologically active ingredient (A) contained therein.

In a preferred embodiment, the release per area of the pharmacologically active ingredient (A) from the pharmaceutical dosage form according to the invention is faster through the front side and the opposite back side than through the circumferential rim.

A skilled person knows how to measure the release rate of the pharmacologically active ingredient (A) through the individual surfaces of the pharmaceutical dosage form according to the invention. For example, the pharmaceutical dosage form can be covered by an inert varnish that does not dissolve in the release medium. Only a distinct portion of the outer surface of the pharmaceutical dosage form having a well defined size and shape is left uncoated, e.g. by transiently covering said portion when applying the varnish or by mechanically removing the varnish at the desired location.

Alternatively, the pharmaceutical dosage form can be clamped in a suitable device so that only one particular side of the pharmaceutical dosage form (front side, back side and a portion of the circumferential rim, respectively) is contacted with the release medium.

In order to avoid diffusion length effects on the release profile, which effects are due to the shape of the dosage form but not due to the individual release properties of the material under investigation, preferably only the initial release is monitored, e.g. the release after 10, 20, 30, 45 or 60 minutes.

In a preferred embodiment, the dosage form according to the invention releases the pharmacologically active ingredient (A) under in vitro conditions in artificial gastric juice according to the following release profile:
  after 0.5 h at least 5 wt.-%,
  after 1 h at least 10 wt.-%,
  after 3 h at least 20 wt.-%,
  after 6 h at least 35 wt.-%, and
  after 12 h at least 55 wt.-%,
based on the total weight of the pharmacologically active ingredient (A) initially contained in the dosage form.

Preferably, the pharmaceutical dosage form according to the invention is adapted for oral administration. It is also possible, however, to administer the pharmaceutical dosage form via different routes and thus, the pharmaceutical dosage form may alternatively be adapted for buccal, lingual, rectal or vaginal administration. Implants are also possible.

In a preferred embodiment, the pharmaceutical dosage form according to the invention is adapted for administration once daily. In another preferred embodiment, the pharmaceutical dosage form according to the invention is adapted for administration twice daily. In still another preferred embodiment, the pharmaceutical dosage form according to the invention is adapted for administration thrice daily.

For the purpose of the specification, "twice daily" means equal time intervals, i.e., every 12 hours, or different time intervals, e.g., 8 and 16 hours or 10 and 14 hours, between the individual administrations.

For the purpose of the specification, "thrice daily" means equal time intervals, i.e., every 8 hours, or different time intervals, e.g., 6, 6 and 12 hours; or 7, 7 and 10 hours, between the individual administrations.

Preferably, the pharmaceutical dosage form according to the invention effects an at least partially delayed release of the pharmacologically active compounds (A).

Delayed release is understood according to the invention preferably to mean a release profile in which the pharmacologically active compound (A) is released over a relatively long period with reduced intake frequency with the purpose of extended therapeutic action. This is achieved in particular with peroral administration. The expression "at least partially delayed release" covers according to the invention any pharmaceutical dosage forms which ensure modified release of the pharmacologically active compounds (A) contained therein. The pharmaceutical dosage forms preferably comprise coated or uncoated pharmaceutical dosage forms, which are produced with specific auxiliary substances, by particular processes or by a combination of the two possible options in order purposefully to change the release rate or location of release.

In the case of the pharmaceutical dosage forms according to the invention, the release time profile may be modified e.g. as follows: extended release, repeat action release, prolonged release and sustained release.

For the purpose of the specification "extended release" preferably means a product in which the release of active compound is delayed for a finite lag time, after which release is unhindered. For the purpose of the specification "repeat action release" preferably means a product in which a first portion of active compound is released initially, followed by at least one further portion of active compound being released subsequently. For the purpose of the specification "prolonged release" preferably means a product in which the rate of release of active compound from the formulation after administration has been reduced, in order to maintain therapeutic activity, to reduce toxic effects, or for some other therapeutic purpose. For the purpose of the specification "sustained release" preferably means a way of formulating a medicine so that it is released into the body steadily, over a long period of time, thus reducing the dosing frequency. For further details, reference may be made, for example, to K. H. Bauer, Lehrbuch der Pharmazeutischen Technologie, 6th edition, W V G Stuttgart, 1999; and European Pharmacopoeia.

The pharmaceutical dosage form according to the invention may comprise one or more pharmacologically active compounds (A) at least in part in a further delayed-release form, wherein delayed release may be achieved with the assistance of conventional materials and processes known to the person skilled in the art, for example by embedding the substance in a delayed-release matrix or by applying one or more delayed-release coatings. Substance release must, however, be controlled such that addition of delayed-release materials does not impair the necessary breaking strength. Controlled release from the pharmaceutical dosage form according to the invention is preferably achieved by embedding the substance in a matrix. Component (C) may serve as such a matrix. The auxiliary substances acting as matrix materials control release. Matrix materials may, for example, be hydrophilic, gel-forming materials, from which release proceeds mainly by diffusion, or hydrophobic materials, from which release proceeds mainly by diffusion from the pores in the matrix.

Preferably, under physiological conditions the pharmaceutical dosage form according to the invention has released after 30 minutes 0.1 to 75%, after 240 minutes 0.5 to 95%, after 480 minutes 1.0 to 100% and after 720 minutes 2.5 to 100% of the pharmacologically active compound (A). Further preferred release profiles $R_1$ to $R_5$ are summarized in the table here below [all data in wt.-% of released pharmacologically active compound (A)]:

| time | $R_1$ | $R_2$ | $R_3$ | $R_4$ | $R_5$ |
|---|---|---|---|---|---|
| 60 min | 0-30 | 0-50 | 0-50 | 15-25 | 20-50 |
| 120 min | 0-40 | 0-75 | 0-75 | 25-40 | 40-75 |
| 240 min | 3-55 | 3-95 | 10-95 | 40-70 | 60-95 |
| 480 min | 10-65 | 10-100 | 35-100 | 60-90 | 80-100 |
| 720 min | 20-75 | 20-100 | 55-100 | 70-100 | 90-100 |
| 960 min | 30-88 | 30-100 | 70-100 | >80 | |
| 1440 min | 50-100 | 50-100 | >90 | | |
| 2160 min | >80 | >80 | | | |

Preferably, under in vitro conditions the pharmaceutical dosage form has released after 0.5 h 1.0 to 35 wt.-%, after 1 h 5.0 to 45 wt.-%, after 2 h 10 to 60 wt.-%, after 4 h at least 15 wt.-%, after 6 h at least 20 wt.-%, after 8 h at least 25 wt.-% and after 12 h at least 30 wt.-% of the pharmacologically active compound (A) that was originally contained in the pharmaceutical dosage form.

Suitable in vitro conditions are known to the skilled artisan. In this regard it can be referred to, e.g., the European Pharmacopoeia and to the experimental section. Preferably, the release profile is measured under the following conditions: Paddle apparatus equipped with sinker, 50 rpm, 37±5° C., 900 mL simulated intestinal fluid pH 6.8 (phosphate buffer). In a preferred embodiment, to rotational speed of the paddle is increased to 100 rpm.

Preferably, the release profile of the pharmaceutical dosage form according to the present invention is stable upon storage, preferably upon storage at elevated temperature, e.g. 37° C., for 3 months in sealed containers. In this regard "stable" means that when comparing the initial release profile with the release profile after storage, at any given time point the release profiles deviate from one another by not more than 20%, more preferably not more than 15%, still more preferably not more than 10%, yet more preferably not more than 7.5%, most preferably not more than 5.0% and in particular not more than 2.5%.

The pharmaceutical dosage form according to the invention contains a pharmacologically active compound (A), for the purpose of the specification also referred to as "component (A)". The pharmacologically active ingredient (A) is embedded in a matrix comprising a polymer (C).

In a preferred embodiment, under ambient conditions, the solubility of component (A) in pure water is at least 1.0 g/L, more preferably at least 5.0 g/L, still more preferably at least 10 g/L, yet more preferably at least 25 g/L, most preferably at least 50 g/L and in particular at least 100 g/L.

In another preferred embodiment, under ambient conditions, the solubility of component (A) in pure water is at most 1.0 g/L, more preferably at most 0.5 g/L, still more preferably at most 0.1 g/L, yet more preferably at most 0.05 g/L, most preferably at most 0.01 g/L and in particular at most 0.005 g/L.

The pharmaceutical dosage form according to the invention contains a pharmaceutically effective amount of a pharmacologically active compound (A), which justifies use of the pharmaceutical dosage form as a pharmaceutical preparation and is the cause of the activity thereof. Pharmacologically active compounds (A) which may in principle be considered in the pharmaceutical dosage form according to the invention are any known pharmaceutical substances, wherein these substances may be present in the pharmaceutical dosage form according to the invention as such, in the form the derivatives thereof, in particular esters or ethers, or in each case in the form of corresponding physiologically acceptable compounds, in particular in the form of the corresponding salts or solvates thereof, as racemates or in a form enriched in one or more stereoisomers (enantiomers or diastereomers).

The pharmaceutical dosage form according to the invention is suitable for the administration of a number of pharmacologically active compounds (A) in a single pharmaceutical dosage form. Preferably, the pharmaceutical dosage form contains only one particular pharmacologically active compound (A).

The amount of the pharmacologically active compound (A), based on the total amount of the pharmaceutical dosage form, is preferably within the range from 0.01 to 95 wt.-%, more preferably from 0.5 to 80 wt.-%, still more preferably 1.0 to 70 wt.-%, most preferably 5.0 to 60 wt.-% and in particular 10 to 50 wt.-%. In a preferred embodiment it is more than 20 wt.-%.

In a preferred embodiment the pharmaceutical dosage form according to the invention contains a psychotropically acting substance as the pharmacologically active compound (A).

The person skilled in the art knows which substances have a psychotropic action. Substances which influence psychological processes commonly have a psychotropic action, i.e. they act specifically on psychological functions. Substances with a psychotropic action may thus influence mood, either raising or lowering it. For the purpose of the description, substances with a psychotropic action include in particular opioids, stimulants, tranquilizers (e.g. barbiturates and benzodiazepines) and other narcotics. Substances with a psychotropic action preferably comprise substances which, in particular when improperly administered (in particular with the intention of abuse), cause an accelerated increase in active compound levels relative to proper oral administration, giving the abuser the desired effect, namely the "kick" or "rush". This kick is also obtained if the powdered pharmaceutical dosage form is administered nasally, i.e. is sniffed. Substances with a psychotropic action are preferably substances which (in the appropriate dose and pharmaceutical dosage form and when administered appropriately) influence human mental activity and/or sensory perception in such a way that they are fundamentally suited to abuse.

Preferably, the pharmacologically active ingredient (A) is an opioid.

In particular, the pharmaceutical dosage form according to the invention preferably contains a psychotropically acting substance selected from the group consisting of opioids [A07DA, N01AH, N02A, R05DA, R05FA,]; barbiturates [N01AF, N01AG, N03AA]; benzodiazepine derivatives [N03AE]; agents for treating opiate dependency [N07BC]; anxiolytics [N05B]; hypnotics and sedatives [N05C]; psychostimulants, agents for treating attention-deficit/hyperactivity disorder (ADHD) and nootropics [N06B]; antiemetics [A04A]; antiobesity preparations excluding diet products [A08A]; centrally acting muscle relaxants [M03B]; and antidotes [V03AB]. The abbreviations stated in square brackets here correspond to the ATC Index ("Gelbe Liste"), as used by the WHO for classifying pharmaceutical substances (preferred version: 2007 or 2008).

The pharmaceutical dosage form according to the invention preferably contains a psychotropically acting substance selected from the group consisting of opioids, vanilloid receptor modulators, serotonin/norepinephrine/dopamine modulators, GABA modulators, NMDA antagonists, ion channel blockers/modulators, cannabionoids, and other NSAIDS.

The following opiates, opioids, tranquilizers or other narcotics are substances with a psychotropic action, i.e. have a potential of abuse, and hence are preferably contained in the pharmaceutical dosage form according to the invention: alfentanil, allobarbital, allylprodine, alphaprodine, alprazolam, amfepramone, amphetamine, amphetaminil, amobarbital, anileridine, apocodeine, axomadol, barbital, bemidone, benzylmorphine, bezitramide, bromazepam, brotizolam, buprenorphine, butobarbital, butorphanol, camazepam, carfentanil, cathine/D-norpseudoephedrine, chlordiazepoxide, clobazam clofedanol, clonazepam, clonitazene, clorazepate, clotiazepam, cloxazolam, cocaine, codeine, cyclobarbital, cyclorphan, cyprenorphine, delorazepam, desomorphine, dextromoramide, dextropropoxyphene, dezocine, diampromide, diamorphone, diazepam, dihydrocodeine, dihydromorphine, dihydromorphone, dimenoxadol, dimephetamol, dimethylthiambutene, dioxaphetylbutyrate, dipipanone, dronabinol, eptazocine, estazolam, ethoheptazine, ethylmethylthiambutene, ethyl loflazepate, ethylmorphine, etonitazene, etorphine, fencamfamine, fenethylline, fenpipramide, fenproporex, fentanyl, fludiazepam, flunitrazepam, flurazepam, halazepam, haloxazolam, heroin, hydrocodone, hydromorphone, hydroxypethidine, isomethadone, hydroxymethylmorphinan, ketazolam, ketobemidone, levacetylmethadol (LAAM), levomethadone, levorphanol, levophenacylmorphane, levoxemacin, lisdexamfetamine dimesylate, lofentanil, loprazolam, lorazepam, lormetazepam, mazindol, medazepam, mefenorex, meperidine, meprobamate, metapon, meptazinol, metazocine, methylmorphine, metamphetamine, methadone, methaqualone, 3-methylfentanyl, 4-methylfentanyl, methylphenidate, methylphenobarbital, methyprylon, metopon, midazolam, modafinil, morphine, myrophine, nabilone, nalbuphene, nalorphine, narceine, nicomorphine, nimetazepam, nitrazepam, nordazepam, norlevorphanol, normethadone, normorphine, norpipanone, opium, oxazepam, oxazolam, oxycodone, oxymorphone, Papaver somniferum, papaveretum, pernoline, pentazocine, pentobarbital, pethidine, phenadoxone, phenomorphane, phenazocine, phenoperidine, piminodine, pholcodeine, phenmetrazine, phenobarbital, phentermine, pinazepam, pipradrol, piritramide, prazepam, profadol, proheptazine, promedol, properidine, propoxyphene, remifentanil, secbutabarbital, secobarbital, sufentanil, tapentadol, temazepam, tetrazepam, tilidine (cis and trans), tramadol, triazolam, vinylbital, N-(1-methyl-2-piperidinoethyl)-N-(2-pyridyl)

propionamide, (1R,2R)-3-(3-dimethylamino-1-ethyl-2-methyl-propyl)phenol, (1R,2R,4S)-2-(dimethylamino) methyl-4-(p-fluorobenzyloxy)-1-(m-methoxyphenyl) cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3-(3-methoxyphenyl)-2-methyl-pentan-3-ol, (1RS,3RS,6RS)-6-dimethylaminomethyl-1-(3-methoxyphenyl)-cyclohexane-1,3-diol, preferably as racemate, 3-(2-dimethylaminomethyl-1-hydroxy-cyclohexyl)phenyl 2-(4-isobutyl-phenyl)propionate, 3-(2-dimethylaminomethyl-1-hydroxy-cyclohexyl)phenyl 2-(6-methoxy-naphthalen-2-yl)propionate, 3-(2-dimethylaminomethyl-cyclohex-1-enyl)-phenyl 2-(4-isobutyl-phenyl)propionate, 3-(2-dimethylaminomethyl-cyclohex-1-enyl)-phenyl 2-(6-methoxy-naphthalen-2-yl)propionate, (RR-SS)-2-acetoxy-4-trifluoromethyl-benzoic acid 3-(2-dimethylaminomethyl-1-hydroxy-cyclohexyl)-phenyl ester, (RR-SS)-2-hydroxy-4-trifluoromethyl-benzoic acid 3-(2-dimethylaminomethyl-1-hydroxy-cyclohexyl)-phenyl ester, (RR-SS)-4-chloro-2-hydroxy-benzoic acid 3-(2-dimethylaminomethyl-1-hydroxy-cyclohexyl)-phenyl ester, (RR-SS)-2-hydroxy-4-methyl-benzoic acid 3-(2-dimethylaminomethyl-1-hydroxy-cyclohexyl)-phenyl ester, (RR-SS)-2-hydroxy-4-methoxy-benzoic acid 3-(2-dimethylaminomethyl-1-hydroxy-cyclohexyl)-phenyl ester, (RR-SS)-2-hydroxy-5-nitro-benzoic acid 3-(2-dimethylaminomethyl-1-hydroxy-cyclohexyl)-phenyl ester, (RR-SS)-2',4'-difluoro-3-hydroxy-biphenyl-4-carboxylic acid 3-(2-dimethylaminomethyl-1-hydroxy-cyclohexyl)-phenyl ester, and corresponding stereoisomeric compounds, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the salts thereof and solvates, e.g. hydrochlorides.

In a preferred embodiment the pharmaceutical dosage form according to the invention contains an opioid selected from the group consisting of DPI-125, M6G (CE-04-410), ADL-5859, CR-665, NRP290 and sebacoyl dinalbuphine ester.

In a preferred embodiment the pharmaceutical dosage form according to the invention contains one pharmacologically active compound (A) or more pharmacologically active compounds (A) selected from the group consisting of oxymorphone, hydromorphone and morphine, or the physiologically acceptable compounds thereof, in particular the salts thereof and solvates.

In another preferred embodiment, the pharmacologically active compound (A) is selected from the group consisting of tapentadol, faxeladol and axomadol, or the physiologically acceptable compounds thereof, in particular the salts thereof and solvates.

In a preferred embodiment the pharmaceutical dosage form according to the invention contains one pharmacologically active compound (A) or more pharmacologically active compounds (A) selected from the group consisting of 1,1-(3-dimethylamino-3-phenyl-pentamethylen)-6-fluor-1,3,4,9-tetrahydropyrano[3,4-b]indole, in particular its hemicitrate; 1,1-[3-dimethylamino-3-(2-thienyl)pentamethylen]-1,3,4,9-tetrahydropyrano[3,4-b]indole, in particular its citrate; and 1,1-[3-dimethylamino-3-(2-thienyl)pentamethylen]-1,3,4,9-tetrahydropyrano[3,4-b]-6-fluoro-indole, in particular its hemicitrate. These compounds are known, for example, from WO 2004/043967 or WO 2005/066183. The corresponding descriptions are hereby introduced as a reference and are deemed to be part of the disclosure.

For the purposes of the description, the pharmacokinetic parameters, which may be determined from the blood plasma concentrations of the pharmacologically active compound (A), are defined as follows:

| | |
|---|---|
| $C_{max}$ | maximum measured plasma concentration of the active ingredient after single administration (≡ average peak plasma level) |
| $t_{max}$ | interval of time from administration of the active ingredient until $C_{max}$ is reached |
| $t_{1/2}$ | half-life |
| $AUC_{0-\infty}$ | total area under the curve |

The above parameters are in each case stated as mean values of the individual values for all investigated patients/test subjects.

A person skilled in the art knows how the pharmacokinetic parameters of the active ingredient may be calculated from the measured concentrations of the active ingredient in the blood plasma. In this connection, reference may be made, for example, to Willi Cawello (ed.) *Parameters for Compartment-free Pharmacokinetics*, Shaker Verlag Aachen (1999).

In a preferred embodiment, after preferably oral administration of the dosage form according to the invention, in vivo the average peak plasma level ($C_{max}$) is on average reached after $t_{max}$ 4.0±2.5 h, more preferably after $t_{max}$ 4.0±2.0 h, still more preferably after $t_{max}$ 4.0±1.5 h, most preferably after $t_{max}$ 4.0±1.0 h and in particular after $t_{max}$ 4.0±0.5 h. In another preferred embodiment, after preferably oral administration of the dosage form according to the invention, in vivo the average peak plasma level ($C_{max}$) is on average reached after $t_{max}$ 5.0±2.5 h, more preferably after $t_{max}$ 5.0±2.0 h, still more preferably after $t_{max}$ 5.0±1.5 h, most preferably after $t_{max}$ 5.0±1.0 h and in particular after $t_{max}$ 5.0±0.5 h. In still another preferred embodiment, after preferably oral administration of the dosage form according to the invention, in vivo the average peak plasma level ($C_{max}$) is on average reached after $t_{max}$ 6.0±2.5 h, more preferably after $t_{max}$ 6.0±2.0 h, still more preferably after $t_{max}$ 6.0±1.5 h, most preferably after $t_{max}$ 6.0±1.0 h and in particular after $t_{max}$ 6.0±0.5 h.

In a preferred embodiment, the average value for $t_{1/2}$ after preferably oral administration of the dosage form according to the invention in vivo is 4.3±2.5 h, more preferably 4.3±2.0 h, still more preferably 4.3±1.5 h, most preferably 4.3±1.0 h, and in particular 4.3±0.5 h. In another preferred embodiment, the average value for $t_{1/2}$ after preferably oral administration of the dosage form according to the invention in vivo is preferably 5.3±2.5 h, more preferably 5.3±2.0 h, still more preferably 5.3±1.5 h, most preferably 5.3±1.0 h, and in particular 5.3±0.5 h. In still another preferred embodiment, the average value for $t_{1/2}$ after preferably oral administration of the dosage form according to the invention in vivo is preferably 6.3±2.5 h, more preferably 6.3±2.0 h, still more preferably 6.3±1.5 h, most preferably 6.3±1.0 h, and in particular 6.3±0.5 h.

In a preferred embodiment, the pharmacologically active compound (A) is tapentadol or a physiologically acceptable salt thereof, and after preferably oral administration of the dosage form according to the invention, in vivo the average value for the total area under the curve $AUC_{0-\infty}$ is 825±600 ng·h/mL, more preferably 825±500 ng·h/mL, still more preferably 825±400 ng·h/mL, yet more preferably 825±300 ng·h/mL, most preferably 825±200 ng·h/mL, and in particular 825±100 ng·h/mL. In another preferred embodiment, the pharmacologically active compound (A) is tapentadol or a physiologically acceptable salt thereof, and after preferably oral administration of the dosage form according to the invention, in vivo the average value for the total area under the curve $AUC_{0-\infty}$, is 1100±600 ng·h/mL, more preferably 1100±500 ng·h/mL, still more preferably 1100±400 ng·h/mL, yet more preferably 1100±300 ng·h/mL, most preferably 1100±200 ng·h/mL, and in particular 1100±100 ng·h/mL.

In a preferred embodiment, the pharmacologically active compound (A) is tapentadol or a physiologically acceptable salt thereof, and after preferably oral administration of the dosage form according to the invention, in vivo the average value of $C_{max}$ is 63±40 ng/mL, more preferably 63±30 ng/mL, still more preferably 63±20 ng/mL, yet more preferably 63±15 ng/mL, most preferably 63±10 ng/mL and in particular 63±5 ng/mL. In another preferred embodiment, the pharmacologically active compound (A) is tapentadol or a physiologically acceptable salt thereof, and after preferably oral administration of the dosage form according to the invention, in vivo the average value of $C_{max}$ is 89±40 ng/mL, more preferably 89±30 ng/mL, still more preferably 89±20 ng/mL, yet more preferably 89±15 ng/mL, most preferably 89±10 ng/mL and in particular 89±5 ng/mL.

In a particularly preferred embodiment the pharmacologically active compound (A) is tapentadol or a physiologically acceptable salt thereof and the pharmaceutical dosage form according to the invention is bioequivalent to a formulation that contains tapentadol or a physiologically acceptable salt thereof in a dosage of 200 mg and 250 mg, respectively, and is characterized by the following pharmacokinetic data:

| Parameter | dosage 200 mg | dosage 250 mg |
|---|---|---|
| $AUC_{0-\infty}$ | 825 ng · h/mL | 1096 ng · h/mL |
| $C_{max}$ | 62.5 ng/mL | 89.3 ng/mL |
| $t_{max}$ | 5.00 h | 5.00 h |
| $t_{1/2}$ | 5.2 h | 5.4 h |

The skilled person is aware what requirements have to be satisfied in order to achieve bioequivalence. In this regard it can be referred e.g. to "*Note for Guidance on the Investigation of Bioavailability and Bioequivalence*", EMEA, London, 26 Jul. 2001 (CPMP/EWP/QWP/1401/98); "*Guidance for Industry—Bioavailability and Bioequivalence—Studies for Orally Administered Drug Products—General Considerations*", FDA, BP, Announced in the Federal Register: Volume 68, Number 53/Mar. 19, 2003; and "*Guidance for Industry—Statistical Approaches to Establishing Bioequivalence*", FDA, BP, January 2001.

In general, two medicinal products are bioequivalent if they are pharmaceutically equivalent or pharmaceutical alternatives and if their bioavailabilities after administration in the same molar dose are similar to such degree that their effects, with respect to both efficacy and safety, will be essentially the same. Preferably, statistical data should be analyzed using ANOVA based on a 90% confidence interval. For example, as regards AUC-ratio, the 90% confidence interval for this measure of relative bioavailability should lie within an acceptance interval of 0.80-1.25, and as regards $C_{max}$-ratio, the 90% confidence interval for this measure of relative bioavailability should lie within an acceptance interval of 0.80-1.25.

In a preferred embodiment, the pharmaceutical dosage form according to the invention contains no substances which irritate the nasal passages and/or pharynx, i.e. substances which, when administered via the nasal passages and/or pharynx, bring about a physical reaction which is either so unpleasant for the patient that he/she does not wish to or cannot continue administration, for example burning, or physiologically counteracts taking of the corresponding active compound, for example due to increased nasal secretion or sneezing. Further examples of substances which irritate the nasal passages and/or pharynx are those which cause burning, itching, an urge to sneeze, increased formation of secretions or a combination of at least two of these stimuli. Corresponding substances and the quantities thereof which are conventionally to be used are known to the person skilled in the art. Some of the substances which irritate the nasal passages and/or pharynx are accordingly based on one or more constituents or one or more plant parts of a hot substance drug. Corresponding hot substance drugs are known per se to the person skilled in the art and are described, for example, in "Pharmazeutische Biologie—Drogen und ihre Inhaltsstoffe" by Prof. Dr. Hildebert Wagner, 2nd, revised edition, Gustav Fischer Verlag, Stuttgart—New York, 1982, pages 82 et seq. The corresponding description is hereby introduced as a reference and is deemed to be part of the disclosure.

The pharmaceutical dosage form according to the invention furthermore preferably contains no antagonists for the pharmacologically active compound (A), preferably no antagonists against psychotropic substances, in particular no antagonists against opioids. Antagonists suitable for a given pharmacologically active compound (A) are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no antagonists selected from among the group comprising naloxone, naltrexone, nalmefene, nalide, nalmexone, nalorphine or naluphine, in each case optionally in the form of a corresponding physiologically acceptable compound, in particular in the form of a base, a salt or solvate; and no neuroleptics, for example a compound selected from among the group comprising haloperidol, promethacine, fluphenazine, perphenazine, levomepromazine, thioridazine, perazine, chlorpromazine, chlorprothixine, zuclopenthixol, flupentixol, prothipendyl, zotepine, benperidol, pipamperone, melperone and bromperidol.

The pharmaceutical dosage form according to the invention furthermore preferably contains no emetic. Emetics are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no emetic based on one or more constituents of ipecacuanha (ipecac) root, for example based on the constituent emetine, as are, for example, described in "Pharmazeutische Biologie—Drogen und ihre Inhaltsstoffe" by Prof. Dr. Hildebert Wagner, 2nd, revised edition, Gustav Fischer Verlag, Stuttgart, N.Y., 1982. The corresponding literature description is hereby introduced as a reference and is deemed to be part of the disclosure. The pharmaceutical dosage form according to the invention preferably also contains no apomorphine as an emetic.

Finally, the pharmaceutical dosage form according to the invention preferably also contains no bitter substance. Bitter substances and the quantities effective for use may be found in US-2003/0064099 A1, the corresponding disclosure of which should be deemed to be the disclosure of the present application and is hereby introduced as a reference. Examples of bitter substances are aromatic oils, such as peppermint oil, eucalyptus oil, bitter almond oil, menthol, fruit aroma substances, aroma substances from lemons, oranges, limes, grapefruit or mixtures thereof, and/or denatonium benzoate.

The pharmaceutical dosage form according to the invention accordingly preferably contains neither substances which irritate the nasal passages and/or pharynx, nor antagonists for the pharmacologically active compound (A), nor emetics, nor bitter substances.

The pharmaceutical dosage form according to the invention is characterized by a comparatively homogeneous distribution of the pharmacologically active compound (A). Preferably, the content of the pharmacologically active compound (A) in two segments of the pharmaceutical dosage form having a volume of 1.0 mm³ each, deviates from one another by not more than ±10%, more preferably not more than more than ±7.5%, still more preferably not more than ±5.0%, most preferably not more than ±2.5%, and in particular not more than ±1.0%. When the pharmaceutical dosage form is film coated, said two segments of the pharmaceutical dosage form having a volume of 1.0 mm³ each are preferably segments of the core, i.e. do not contain any coating material.

Preferably, all components of the pharmaceutical dosage form according to the invention have a comparatively homogeneous distribution within the pharmaceutical dosage form. Preferably, the content of each component in two segments of the pharmaceutical dosage form having a volume of 1.0 mm³ each, deviates from one another by not more than ±10%, more preferably not more than more than ±7.5%, still more preferably not more than ±5.0%, most preferably not more than ±2.5%, and in particular not more than ±1.0%. When the pharmaceutical dosage form is film coated, said two segments of the pharmaceutical dosage form having a volume of 1.0 mm³ each are preferably segments of the core, i.e. do not contain any coating material.

Preferably, the pharmaceutical dosage form according to the invention contains at least one polymer (C), for the purpose of the specification also referred to as "component (C)". Preferably, the pharmaceutical dosage form contains at least one synthetic, semi-synthetic or natural polymer (C), which contributes considerably to the elevated breaking strength (resistance to crushing) of the pharmaceutical dosage form. For the purpose of the specification a "semi-synthetic" product has been produced by chemical manipulation of naturally occurring substances.

Preferably, the mechanical properties of the pharmaceutical dosage form according to the invention, particularly its breaking strength, substantially rely on the presence of polymer (C), although its mere presence does not suffice in order to achieve said properties. The advantageous properties of the pharmaceutical dosage form according to the invention, in particular also its mechanical properties, may not automatically be achieved by simply hot-melt extruding the pharmacologically active compound (A), polymer (C), and optionally further excipients by means of conventional methods for the preparation of pharmaceutical dosage forms by hot-melt extrusion. In fact, usually suitable extruders must be selected for the preparation and critical extrusion parameters must be adjusted, particularly pressure/force, temperature and time. Thus, even if conventional extruders are used, the process protocols usually must be adapted in order to meet the required criteria.

Preferably, polymer (C) is water-soluble. Preferably, polymer (C) is substantially unbranched.

Polymer (C) may comprise a single type of polymer having a particular average molecular weight, or a mixture (blend) of different polymers, such as two, three, four or five polymers, e.g., polymers of the same chemical nature but different average molecular weight, polymers of different chemical nature but same average molecular weight, or polymers of different chemical nature as well as different molecular weight.

Individual or combinations of polymers may be selected from the group comprising polyalkylene oxide, preferably polymethylene oxide, polyethylene oxide, polypropylene oxide; polyethylene, polypropylene, polyvinyl chloride, polycarbonate, polystyrene, polyvinylpyrrolidone, poly(alk) acrylate, poly(hydroxy fatty acids), such as for example poly(3-hydroxy-butyrate-co-3-hydroxyvalerate) (Biopol®), poly(hydroxyvaleric acid); polycaprolactone, polyvinyl alcohol, polyesteramide, polyethylene succinate, polylactone, polyglycolide, polyurethane, polyamide, polylactide, polyacetal (for example polysaccharides optionally with modified side chains), polylactide/glycolide, polylactone, polyglycolide, polyorthoester, polyanhydride, block polymers of polyethylene glycol and polybutylene terephthalate (Polyactive®), polyanhydride (Polifeprosan), copolymers thereof, block-copolymers thereof, and mixtures of at least two of the stated polymers, or other polymers with the above characteristics.

Preferably, polymer (C) comprises a polyalkylene oxide, more preferably a polyethylene oxide, a polypropylene oxide, an ethylene oxide-propylene oxide copolymerisate, which may be e.g. a random copolymer, alternating copolymer or block copolymer, or a mixture of any of the foregoing.

Particularly preferred are high molecular weight polymers with a preferably weight average molecular weight ($M_w$) or viscosity average molecular weight ($M_\eta$) of at least of at least $0.1 \cdot 10^6$ g/mol, of at least $0.2 \cdot 10^6$ g/mol, of at least $0.5 \cdot 10^6$ g/mol, of at least $1.0 \cdot 10^6$ g/mol, of at least $2.5 \cdot 10^6$ g/mol, of at least $5.0 \cdot 10^6$ g/mol, of at least $7.5 \cdot 10^6$ g/mol or of at least $10 \cdot 10^6$ g/mol, preferably $1.0 \cdot 10^6$ g/mol to $15 \cdot 10^6$ g/mol. Suitable methods for determining $M_w$ or $M_\eta$ are known to the person skilled in the art. Preferably, $M_\eta$ is determined using rheological measurements and $M_w$ is determined using gel permeation chromatography (GPC) on suitable phases.

Preferably, the molecular weight dispersity $M_w/M_n$ of polymer (C) is within the range of 2.5±2.0, more preferably 2.5±1.5, still more preferably 2.5±1.0, yet more preferably 2.5±0.8, most preferably 2.5±0.6, and in particular 2.5±0.4.

The polymers preferably have a viscosity at 25° C. of 4,500 to 17,600 cP, measured in a 5 wt.-% aqueous solution using a model RVF Brookfield viscosimeter (spindle no. 2/rotational speed 2 rpm), of 400 to 4,000 cP, measured on a 2 wt.-% aqueous solution using the stated viscosimeter (spindle no. 1 or 3/rotational speed 10 rpm) or of 1,650 to 10,000 cP, measured on a 1 wt.-% aqueous solution using the stated viscosimeter (spindle no. 2/rotational speed 2 rpm).

Most preferred are thermoplastic polyalkylene oxides having a weight average molecular weight ($M_w$) or a viscosity average molecular weight ($M_\eta$) of at least $0.2 \cdot 10^6$ g/mol, more preferably at least $0.3 \cdot 10^6$ g/mol, still more preferably at least $0.4 \cdot 10^6$ g/mol, yet more preferably at least $0.5 \cdot 10^6$ g/mol, most preferably at least $1.0 \cdot 10^6$ g/mol and in particular within the range of $1.0 \cdot 10^6$ to $15 \cdot 10^6$ g/mol are preferred, e.g. polyethylene oxides, polypropylene oxides or the (block-) copolymers thereof.

In a preferred embodiment according to the invention the polymer (C) comprises a polyalkylene oxide having a weight average molecular weight ($M_w$) or viscosity average molecular weight ($M_\eta$) of at least $0.2 \cdot 10^6$ g/mol in combination with at least one further polymer, preferably but not necessarily also having a weight average molecular weight ($M_w$) or viscosity average molecular weight ($M_\eta$) of at least $0.2 \cdot 10^6$ g/mol, selected from the group consisting of polyethylene, polypropylene, polyvinyl chloride, polycarbonate, polystyrene, polyacrylate, poly(hydroxy fatty acids), polycaprolactone, polyvinyl alcohol, polyesteramide, polyethylene succinate, polylactone, polyglycolide, polyurethane, polyvinylpyrrolidone, polyamide, polylactide, polylactide/glycolide, polylactone, polyglycolide, polyorthoester, polyanhydride, block polymers of polyethylene glycol and polybutylene terephthalate, polyanhydride, polyacetal, cellulose esters, cellulose ethers and copolymers thereof. Cellulose esters and cellulose ethers are particularly preferred, e.g. methylcellulose, ethylcellulose, hydroxymethyl-cellulose, hydroxypropylmethylcellulose, carboxymethylcellulose, and the like.

In a preferred embodiment, said further polymer is neither a polyalkylene oxide nor a polyalkylene glycol. Nonetheless, the pharmaceutical dosage form may contain polyalkylene glycol, e.g. as plasticizer, but then, the pharmaceutical dosage form preferably is a ternary mixture of polymers: component (C)+further polymer+plasticizer.

In a particularly preferred embodiment, said further polymer is a hydrophilic cellulose ester or cellulose ether, preferably hydroxypropylmethylcellulose, preferably having an average viscosity of 100,000±50,000 mPas, more preferably 100,000±20,000 mPas.

Preferably, the content of said further polymer amounts to 0.5 to 25 wt.-%, more preferably 1.0 to 20 wt.-%, still more preferably 2.0 to 17.5 wt.-%, yet more preferably 3.0 to 15 wt.-% and most preferably 4.0 to 12.5 wt.-% and in particular 5.0 to 10 wt.-%, based on the total weight of the polyalkylene oxide.

In a preferred embodiment the relative weight ratio of said polyalkylene oxide and said further polymer is within the range of from 20:1 to 1:20, more preferably 10:1 to 1:10, still more preferably 7:1 to 1:5, yet more preferably 5:1 to 1:1, most preferably 4:1 to 1, 5:1 and in particular 3:1 to 2:1.

Preferably, the content of said further polymer amounts to 0.5 to 25 wt.-%, more preferably 1.0 to 20 wt.-%, still more preferably 2.0 to 22.5 wt.-%, yet more preferably 3.0 to 20 wt.-% and most preferably 4.0 to 17.5 wt.-% and in particular 5.0 to 15 wt.-%, based on the total weight of the pharmaceutical dosage form.

It is not intended to be bound by any theory, but it is believed that the further polymer may serve as a supplementary matrix material that guarantees a minimal retardant effect on the release of the pharmacologically active compound (A) even if the molecular chains of the polyalkylene oxide have been partially damaged in the course of the manufacture of the pharmaceutical dosage form, e.g. by extrusion, thereby decreasing the average molecular weight. Furthermore, it seems that the further polymer contributes to the storage stability of the dosage form, particularly with respect to its release profile.

Physiologically acceptable, hydrophobic materials which are known to the person skilled in the art may be used as supplementary matrix materials. Polymers, particularly preferably cellulose ethers, cellulose esters and/or acrylic resins are preferably used as hydrophilic matrix materials. Ethylcellulose, hydroxypropylmethylcellulose, hydroxypropylcellulose, hydroxymethylcellulose, poly(meth)acrylic acid and/or the derivatives thereof, such as the salts, amides or esters thereof are very particularly preferably used as matrix materials. Matrix materials prepared from hydrophobic materials, such as hydrophobic polymers, waxes, fats, long-chain fatty acids, fatty alcohols or corresponding esters or ethers or mixtures thereof are also preferred. Mono- or diglycerides of $C_{12}$-$C_{30}$ fatty acids and/or $C_{12}$-$C_{30}$ fatty alcohols and/or waxes or mixtures thereof are particularly preferably used as hydrophobic materials. It is also possible to use mixtures of the above-stated hydrophilic and hydrophobic materials as matrix materials.

Preferably, the overall content of polymer (C) is at least 5 wt.-%, at least 10 wt.-%, at least 15 wt.-% or at least 20 wt.-%, more preferably at least 30 wt.-%, still more preferably at least 40 wt.-%, most preferably at least 50 wt.-% and in particular at least 60 wt.-%, of the total weight of the pharmaceutical dosage form. In a preferred embodiment the content of the polymer (C) is within the range of from about 20 to about 49 wt.-% of the total weight of the pharmaceutical dosage form.

In a preferred embodiment, the overall content of polymer (C) is within the range of 25±20 wt.-%, more preferably 25±15 wt.-%, most preferably 25±10 wt.-%, and in particular 25±5 wt.-%. In another preferred embodiment, the overall content of polymer (C) is within the range of 35±20 wt.-%, more preferably 35±15 wt.-%, most preferably 35±10 wt.-%, and in particular 35±5 wt.-%. In still another preferred embodiment, the overall content of polymer (C) is within the range of 45±20 wt.-%, more preferably 45±15 wt.-%, most preferably 45±10 wt.-%, and in particular 45±5 wt.-%. In yet another preferred embodiment, the overall content of polymer (C) is within the range of 55±20 wt.-%, more preferably 55±15 wt.-%, most preferably 55±10 wt.-%, and in particular 55±5 wt.-%. In a further preferred embodiment, the overall content of polymer (C) is within the range of 65±20 wt.-%, more preferably 65±15 wt.-%, most preferably 65±10 wt.-%, and in particular 65±5 wt.-%. In still a further a preferred embodiment, the overall content of polymer (C) is within the range of 75±20 wt.-%, more preferably 75±15 wt.-%, most preferably 75±10 wt.-%, and in particular 75±5 wt.-%.

In a preferred embodiment, polymer (C) is homogeneously distributed in the pharmaceutical dosage form according to the invention. Preferably, polymer (C) forms a matrix in which the pharmacologically active compound (A) is embedded. In a particularly preferred embodiment, the pharmacologically active compound (A) and polymer (C) are intimately homogeneously distributed in the pharmaceutical dosage form so that the pharmaceutical dosage form does not contain any segments where either pharmacologically active compound (A) is present in the absence of polymer (C) or where polymer (C) is present in the absence of pharmacologically active compound (A).

When the pharmaceutical dosage form is film coated, the polymer (C) is preferably homogeneously distributed in the core of the pharmaceutical dosage form, i.e. the film coating preferably does not contain polymer (C). Nonetheless, the film coating as such may of course contain one or more polymers, which however, preferably differ from the polymer (C) contained in the core.

The dosage form according to the invention exhibits a breaking strength of at least 300 N, typically measured along the longitudinal direction of extension of the dosage form.

The "breaking strength" (resistance to crushing) of a pharmaceutical dosage form is known to the skilled person. In this regard it can be referred to, e.g., W. A. Ritschel, Die Tablette, 2. Auflage, Editio Cantor Verlag Aulendorf, 2002; H Liebermann et al., Pharmaceutical dosage forms: Tablets, Vol. 2, Informa Healthcare; 2 edition, 1990; and Encyclopedia of Pharmaceutical Technology, Informa Healthcare; 1 edition.

For the purpose of the specification, the breaking strength is preferably defined as the amount of force that is necessary in order to fracture the pharmaceutical dosage form (=breaking force). Therefore, for the purpose of the specification the dosage form does preferably not exhibit the desired breaking strength when it breaks, i.e., is fractured into at least two independent parts that are separated from one another. In another preferred embodiment, however, the pharmaceutical dosage form is regarded as being broken if the force decreases by 25% (threshold value) of the highest force measured during the measurement (see below).

The dosage forms according to the invention are distinguished from conventional dosage forms in that, due to their breaking strength, they cannot be pulverized by the application of force with conventional means, such as for example a pestle and mortar, a hammer, a mallet or other usual means for pulverization, in particular devices developed for this purpose (tablet crushers). In this regard "pulverization" means crumbling into small particles that would immediately release the pharmacologically active compound (A) in a suitable medium. Avoidance of pulverization virtually rules out oral or parenteral, in particular intravenous or nasal abuse.

Conventional tablets typically have a breaking strength well below 200 N in any direction of extension. The breaking strength of conventional round tablets may be estimated according to the following empirical formula: Breaking Strength [in N]=10×Diameter Of The Tablet [in mm]. Thus, according to said empirical formula, a round tablet having a breaking strength of at least 500 N would require a diameter of at least 50 mm (about 2 inches). Such a tablet, however, could not be swallowed. The above empirical formula does not apply to the pharmaceutical dosage forms of the invention, which are not conventional but rather special.

Further, the actual mean chewing force is about 220 N (cf., e.g., P. A. Proeschel et al., J Dent Res, 2002, 81(7), 464-468, copy attached). This means that conventional tablets having a breaking strength well below 200 N may be crushed upon chewing, whereas the dosage forms according to the invention may not, at least not in direction of extension $E_1$.

Still further, when applying a gravitational acceleration of about 9.81 m/s$^2$, 300 N correspond to a gravitational force of more than 30 kg, i.e. the pharmaceutical dosage forms according to the invention can withstand a weight of more than 30 kg.

Methods for measuring the breaking strength of a pharmaceutical dosage form are known to the skilled artisan. Suitable devices are commercially available.

For example, the breaking strength (resistance to crushing) can be measured in accordance with the European Pharmacopoeia 5.0, 2.9.8 or 6.0, 2.09.08 "Resistance to Crushing of Tablets". The test is intended to determine, under defined conditions, the resistance to crushing of tablets, measured by the force needed to disrupt them by crushing. The apparatus consists of 2 jaws facing each other, one of which moves towards the other. The flat surfaces of the jaws are perpendicular to the direction of movement. The crushing surfaces of the jaws are flat and larger than the zone of contact with the tablet. The apparatus is calibrated using a system with a precision of 1 Newton. The tablet is placed between the jaws, taking into account, where applicable, the shape, the break-mark and the inscription; for each measurement the tablet is oriented in the same way with respect to the direction of application of the force (typically along the longitudinal direction of extension). The measurement is carried out on 10 tablets, taking care that all fragments of tablets have been removed before each determination. The result is expressed as the mean, minimum and maximum values of the forces measured, all expressed in Newton.

A similar description of the breaking strength (breaking force) can be found in the US Pharmacopoeia. The breaking strength can alternatively be measured in accordance with the method described therein where it is stated that the breaking strength is the force required to cause a tablet to fail (i.e., break) in a specific plane. The tablets are generally placed between two platens, one of which moves to apply sufficient force to the tablet to cause fracture. For conventional, round (circular cross-section) tablets, loading occurs across their diameter (sometimes referred to as diametral loading), and fracture occurs in the plane. The breaking force of tablets is commonly called hardness in the pharmaceutical literature; however, the use of this term is misleading. In material science, the term hardness refers to the resistance of a surface to penetration or indentation by a small probe. The term crushing strength is also frequently used to describe the resistance of tablets to the application of a compressive load. Although this term describes the true nature of the test more accurately than does hardness, it implies that tablets are actually crushed during the test, which is often not the case.

Alternatively, the breaking strength (resistance to crushing) can be measured in accordance with WO 2006/082099, which can be regarded as a modification of the method described in the European Pharmacopoeia. The apparatus used for the measurement is preferably a "Zwick Z 2.5" materials tester, $F_{max}$=2.5 kN with a maximum draw of 1150 mm, which should be set up with one column and one spindle, a clearance behind of 100 mm and a test speed adjustable between 0.1 and 800 mm/min together with testControl software. Measurement is performed using a pressure piston with screw-in inserts and a cylinder (diameter 10 mm), a force transducer, $F_{max}$. 1 kN, diameter=8 mm, class 0.5 from 10 N, class 1 from 2 N to ISO 7500-1, with manufacturers test certificate M according to DIN 55350-18 (Zwick gross force $F_{max}$=1.45 kN) (all apparatus from Zwick GmbH & Co. KG, Ulm, Germany) with Order No BTC-FR 2.5 TH. D09 for the tester, Order No BTC-LC 0050N. P01 for the force transducer, Order No BO 70000 S06 for the centering device.

In a preferred embodiment of the invention, the breaking strength is measured by means of a breaking strength tester Sotax®, type HT100 (Allschwil, Switzerland). The Sotax® HT100 can measure the breaking strength according to two different measurement principles: constant speed (where the test jaw is moved at a constant speed adjustable from 5-200 mm/min) or constant force (where the test jaw increases force linearly adjustable from 5-100 N/sec). In principle, both measurement principles are suitable for measuring the breaking strength of the dosage form according to the invention. Preferably, the breaking strength is measured at constant speed, preferably at a constant speed of 120 mm/min.

In a preferred embodiment, the pharmaceutical dosage form is regarded as being broken if it is fractured into at least two separate pieces.

In another preferred embodiment, the pharmaceutical dosage form is regarded as being broken if the force decreases by 25% (threshold value) of the highest force measured during the measurement. For example, if the highest force measured during the measurement is 144 N, the tablet is regarded as being broken when the force decreases below 108 N (=75% of 144 N; decrease by 25%). The value of the breaking strength in the respective direction of extension is then 144 N. In a preferred embodiment, said threshold value is 30%, more preferably 35%, still more preferably 40%, most preferably 45% and in particular 50%. Under these circumstances, a dosage form may have to be regarded as being broken although it has not been fractured into at least two separate pieces. For example, a dosage form that has been torn in the middle but that has not been fragmented, may have to be regarded as being broken in accordance with this definition of the breaking strength. Thus, in accordance with this definition, failure of the breaking strength test at a particular force may be due to fracture of the dosage form or any other deformation that causes the force to drop below the above threshold value, e.g. rupture, cracking, dunting, cleaving, fissure, and the like.

The pharmaceutical dosage form according to the invention has a breaking strength of at least 300 N, preferably at least 400 N, more preferably at least 500 N, still more preferably at least 750 N, most preferably at least 1000 N and in particular at least 1500 N.

The pharmaceutical dosage form according to the invention exhibits mechanical strength over a wide temperature range, in addition to the breaking strength (resistance to crushing) optionally also sufficient hardness, impact resistance, impact elasticity, tensile strength and/or modulus of elasticity, optionally also at low temperatures (e.g. below −24° C., below −40° C. or in liquid nitrogen), for it to be virtually impossible to pulverize by spontaneous chewing, grinding in a mortar, pounding, etc. Thus, preferably, the comparatively high breaking strength of the pharmaceutical dosage form according to the invention is maintained even at low or very low temperatures, e.g., when the pharmaceutical dosage form is initially chilled to increase its brittleness, for example to temperatures below −25° C., below −40° C. or even in liquid nitrogen.

The pharmaceutical dosage form according to the invention exhibits high impact strength.

For example, the falling impact strength of the pharmaceutical dosage forms is preferably about 0%. The falling impact strength is a breakage ratio obtained when a tablet is allowed to fall from the height of 50 cm onto a stainless steel plate and defined by: {(broken tablets)/(tested tablets)} 100(%).

Preferably, the impact strength of the pharmaceutical dosage form according to the invention is sufficiently high so that it cannot be comminuted by means of a hammer. Preferably, when applying five manual hammer strokes by means of a hammer having a weight of 500 g, the pharmaceutical dosage form cannot be comminuted. In a preferred embodiment, the pharmaceutical dosage form does not only exhibit this impact strength at ambient temperature, but also below +4° C. (refrigerator), more preferably below −33° C. (deep freezer), most preferably below −77° C. (dry ice) and in particular below −190° C. (liquid nitrogen).

Preferably, the pharmaceutical dosage form according to the invention exhibits a cutting resistance of at least 75 N, more preferably at least 100 N, still more preferably at least 125 N, yet more preferably at least 140 N, most preferably at least 150 N and in particular at least 160 N, in at least one direction of extension, preferably in direction of extension $E_1$. Preferably, the cutting test is performed according to DIN EN ISO 604, preferably at a testing speed of 30 mm/min and by means of a universal glass cleaning blade having a thickness of 0.30 mm.

The friability of the pharmaceutical dosage form according to the invention can be measured, e.g., by means of a Pharmatest PTF-E apparatus (Hainburg, Germany) following, e.g., the European Pharmacopeia (Ph. Eur.) specifications. Preferably, the friability of the pharmaceutical dosage form according to the invention is at most 0.50%, more preferably at most 0.40%, still more preferably at most 0.30%, yet more preferably at most 0.20%, most preferably at most 0.10% and in particular at most 0.05%.

Preferably, the pharmaceutical dosage form according to the invention contains a coating, preferably a film-coating. Suitable coating materials are known to the skilled person. Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), ethylcellulose (EC), cellulose acetate phthalate (CAP), hydroxypropylmethylcellulose phthalate (HPMCP); poly(meth)acrylates, such as aminoalkylmethacrylate copolymers, ethylacrylate methyl-methacrylate copolymers, methacrylic acid methylmethacrylate copolymers, methacrylic acid methylmethacrylate copolymers; vinyl polymers, such as polyvinylpyrrolidone, polyvinyl-acetatephthalate, polyvinyl alcohol, polyvinylacetate; and natural film formers, such as shellack.

In a particularly preferred embodiment, the coating is water-soluble. Preferably, the coating is based on polyvinyl alcohol, such as polyvinyl alcohol-part hydrolyzed, and may additionally contain polyethylene glycol, such as macrogol 3350, and/or pigments.

The coating of the pharmaceutical dosage form can increase its storage stability.

The coating can be resistant to gastric juices and dissolve as a function of the pH value of the release environment. By means of this coating, it is possible to ensure that the pharmaceutical dosage form according to the invention passes through the stomach undissolved and the active compound is only released in the intestines. The coating which is resistant to gastric juices preferably dissolves at a pH value of between 5 and 7.5. Corresponding materials and methods for the delayed release of active compounds and for the application of coatings which are resistant to gastric juices are known to the person skilled in the art, for example from "Coated Pharmaceutical dosage forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers.

Besides the pharmacologically active compound (A) and polymer (C) the pharmaceutical dosage form according to the invention may contain further constituents, such as conventional pharmaceutical excipients.

In a preferred embodiment, the pharmaceutical dosage form contains at least one natural, semi-synthetic or synthetic wax (D), for the purpose of the specification also referred to as "component (D)". Preferred waxes are those with a softening point of at least 50° C., more preferably of at least 55° C., still more preferably of at least 60° C., most preferably of at least 65° C. and in particular at least 70° C.

Carnauba wax and beeswax are particularly preferred. Carnauba wax is very particularly preferred. Carnauba wax is a natural wax which is obtained from the leaves of the carnauba palm and has a softening point of at least 80° C. When the wax component is additionally contained, its content is sufficiently high so that the desired mechanical properties of the pharmaceutical dosage form are achieved.

Auxiliary substances (B), further purpose of the specification also referred to as "component (B)", which may be contained in the pharmaceutical dosage form according to the invention are those known auxiliary substances which are conventional for the formulation of solid pharmaceutical dosage forms.

Examples of auxiliary substances (B) are plasticizers, (further) matrix materials, antioxidants and the like.

Suitable plasticizers include triacetin and polyethylene glycol, preferably a low molecular weight polyethylene glycol (e.g. macrogol 6000).

Matrix materials are auxiliary substances which influence active compound release, preferably hydrophobic or hydrophilic, preferably hydrophilic polymers, very particularly preferably hydroxypropylmethylcellulose, and/or antioxidants. Polymers, particularly preferably cellulose ethers, cellulose esters and/or acrylic resins are preferably contained as hydrophilic matrix materials. Ethylcellulose, hydroxypropylmethylcellulose, hydroxypropylcellulose, hydroxymethylcellulose, poly(meth)acrylic acid and/or the derivatives thereof, such as the copolymers, salts, amides or esters thereof are very particularly preferably contained as matrix materials.

Suitable antioxidants are ascorbic acid, butylhydroxyanisole (BHA), butylhydroxytoluene (BHT), salts of ascorbic acid, monothioglycerol, phosphorous acid, vitamin C, vitamin E and the derivatives thereof, coniferyl benzoate, nordihydroguajaretic acid, gallus acid esters, sodium bisulfite, particularly preferably butylhydroxytoluene or butylhydroxyanisole and α-tocopherol. The antioxidant is preferably used in quantities of 0.01 to 10 wt.-%, preferably of 0.03 to 5 wt.-%, relative to the total weight of the pharmaceutical dosage form.

In a preferred embodiment, the pharmaceutical dosage form according to the invention contains citric acid or a physiologically acceptable salt thereof.

Preferred compositions $X_1$ to $X_4$ of the pharmaceutical dosage form according to the invention are summarized in the table here below:

The pharmaceutical dosage form according to the invention is hot-melt extruded, i.e. produced by thermoforming with the assistance of an extruder, preferably without there being any observable consequent discoloration of the extrudate.

In order to investigate the extent of discoloration due to this thermoforming, the colour of the mixture of starting components of which the pharmaceutical dosage form consists is first determined without addition of a color-imparting component, such as for example a coloring pigment or an intrinsically colored component (for example α-tocopherol). This composition is then thermoformed according to the invention, wherein all process steps, including cooling of the extrudate, are performed under an inert gas atmosphere. By way of comparison, the same composition is produced by the same process, but without an inert gas atmosphere. The color of the pharmaceutical dosage form produced according to the invention from the starting composition and of the pharmaceutical dosage form produced by way of comparison is determined. The determination is performed with the assistance of "Munsell Book of Color" from Munsell Color Company Baltimore, Md., USA, 1966 edition. If the color of the pharmaceutical dosage form thermoformed according to the invention has a color with identification no. N 9.5, but at most a color with the identification no. 5Y 9/1, thermoforming is classed as being "without discoloration". If the pharmaceutical dosage form has a color with the identification no. 5Y 9/2 or greater, as determined according to the Munsell Book of Color, the thermoforming is classed as being "with discoloration".

In general, hot-melt extrusion comprises the steps of
i) mixing components (A), (C), optionally (B) and/or (D),
ii) heating the resultant mixture in the extruder at least up to the softening point of component (C) and extruding the thus heated mixture through the outlet orifice of the extruder by application of force,
iii) singulating the still plastic extrudate and forming it into the pharmaceutical dosage form or
iv) forming the cooled or optionally re-heated singulated extrudate into the pharmaceutical dosage form.

Mixing of the components according to process step i) may also proceed in the extruder.

Components (A), (C), optionally (B) and/or (D) may also be mixed in a mixer known to the person skilled in the art. The mixer may, for example, be a roll mixer, shaking mixer, shear mixer or compulsory mixer.

Before blending with the remaining components, component (C) and/or (D) is preferably provided according to the invention with an antioxidant. This may proceed by mixing the two components, (C) and the antioxidant, preferably by dissolving or suspending the antioxidant in a highly volatile solvent and homogeneously mixing this solution or suspension with component (C) and the optionally present component (D) and removing the solvent by drying, preferably under an inert gas atmosphere.

| wt.-% | $X_1$ | $X_2$ | $X_3$ | $X_4$ |
|---|---|---|---|---|
| component (A) | 26.5 ± 25 | 26.5 ± 20 | 26.5 ± 15 | 26.5 ± 13 |
| polyalkylene oxide (e.g. PEO) | 46.5 ± 25 | 46.5 ± 17 | 46.5 ± 12 | 46.5 ± 10 |
| cellulose ester or ether (e.g. HPMC) | 14 ± 7 | 14 ± 5 | 14 ± 2.5 | 14 ± 0.5 |
| plasticizer (e.g. PEG) | 12.5 ± 10 | 12.5 ± 7 | 12.5 ± 5 | 12.5 ± 3 |
| antioxidant (e.g. α-tocopherol) | 0.125 ± 0.12 | 0.125 ± 0.1 | 0.125 ± 0.05 | 0.125 ± 0.03 |

The, preferably molten, mixture which has been heated in the extruder at least up to the softening point of component (C) is extruded from the extruder through a die with at least one bore.

The process according to the invention requires the use of suitable extruders, preferably screw extruders. Screw extruders which are equipped with two screws (twin-screw-extruders) are particularly preferred.

A further aspect of the invention relates to process for the manufacture of a hot-melt extruded pharmaceutical dosage form, preferably as defined above, with controlled release of a pharmacologically active ingredient (A) as defined above embedded in a matrix comprising a polymer (C) as defined above, the dosage form having an oblong shape comprising a longitudinal direction of extension, a transversal direction of extension orthogonal to the longitudinal direction of extension, a front side, an opposite back side and a circumferential rim between said front and back side, comprising the steps of (a) hot-melt extruding a mass comprising
   the pharmacologically active ingredient (A) and
   the polymer (C),
through an oblong die thereby obtaining an extrudate with an oblong cross-section;
(b) cutting said extrudate into slices (preferably in a plane substantially orthogonal to the direction of extrusion) having two opposing cut surfaces of oblong shape;
(c) placing said slices into a tabletting tool comprising upper punch and lower punch in a manner so that the opposing surfaces of oblong shape face said upper and lower punch, respectively;
(d) press-forming dosage forms from the slices; and
(e) optionally, applying a film coating.

The extrusion is preferably performed so that the expansion of the strand due to extrusion is not more than 50%, i.e. that when using a die with a bore having a diameter of e.g. 6 mm, the extruded strand should have a diameter of not more than 9 mm. More preferably, the expansion of the strand is not more than 40%, still more preferably not more than 35%, most preferably not more than 30% and in particular not more than 25%. It has been surprisingly found that if the extruded material in the extruder is exposed to a mechanical stress exceeding a certain limit, a significant expansion of the strand occurs thereby resulting in undesirable irregularities of the properties of the extruded strand, particularly its mechanical properties.

Preferably, extrusion is performed in the absence of water, i.e., no water is added. However, traces of water (e.g., caused by atmospheric humidity) may be present.

The extruder preferably comprises at least two temperature zones, with heating of the mixture at least up to the softening point of component (C) proceeding in the first zone, which is downstream from a feed zone and optionally mixing zone. The throughput of the mixture is preferably from 2.0 kg to 8.0 kg/hour.

After heating at least up to the softening point of component (C), the molten mixture is conveyed with the assistance of the screws, further homogenized, compressed or compacted such that, immediately before emerging from the extruder die, it exhibits a minimum pressure of 5 bar, preferably of at least 7.5 bar, more preferably at least 10 bar, still more preferably at least 12.5 bar, yet more preferably at least 15 bar, most preferably at least 17.5 bar and in particular at least 20 bar, and is extruded through the die as an extruded strand or strands, depending on the number of bores which the die comprises.

In a preferred embodiment, the die head pressure is within the range of from 25 to 85 bar. The die head pressure can be adjusted inter alia by die geometry, temperature profile and extrusion speed.

The casing of the extruder used according to the invention may be heated or cooled. The corresponding temperature control, i.e. heating or cooling, is so arranged that the mixture to be extruded exhibits at least an average temperature (product temperature) corresponding to the softening temperature of component (C) and does not rise above a temperature at which the pharmacologically active compound (A) to be processed may be damaged. Preferably, the temperature of the mixture to be extruded is adjusted to below 180° C., preferably below 150° C., but at least to the softening temperature of component (C). Typical extrusion temperatures are 120° C. and 130° C.

In a preferred embodiment, the extruder torque is within the range of from 25 to 55 Nm. Extruder torque can be adjusted inter alia by die geometry, temperature profile and extrusion speed.

In step (a) of the process according to the invention a mass is hot-melt extruded through an oblong die thereby obtaining an extrudate with an oblong cross-section. In step (b) of the process according to the invention said extrudate obtained in step (a) is cut into slices having two opposing cut surfaces of oblong shape.

Thus, the die geometry predetermines the cross-section of the extrudate as well as the cross-section of the slices which both are oblong, preferably substantially identical.

The oblong cross-section preferably has a maximum lengthwise extension of 21 mm and a maximum crosswise extension of 10 mm.

In a preferred embodiment, the relative ratio of the maximum lengthwise extension to the maximum crosswise extension of the oblong die is at least 1.5:1, more preferably at least 2.0:1, still more preferably at least 2.2:1, yet more preferably at least 2.3:1, most preferably at least 2.4:1 and in particular at least 2.5:1.

Preferred oblong dies have the following lengthwise and crosswise extensions $A_1$ to $A_8$:

| [mm] | $A_1$ | $A_2$ | $A_3$ | $A_4$ | $A_5$ | $A_6$ | $A_7$ | $A_8$ |
|---|---|---|---|---|---|---|---|---|
| lengthwise | 16.5 ± 4 | 16.5 ± 2 | 15 ± 2 | 15 ± 1 | 15 ± 0.5 | 18 ± 2 | 18 ± 1 | 18 ± 0.5 |
| crosswise | 6 ± 2 | 6 ± 1.5 | 5 ± 2 | 5 ± 1 | 5 ± 0.5 | 7 ± 2 | 7 ± 1 | 7 ± 0.5 |

Preferably, the oblong die has elliptic shape or rectangular shape, preferably with rounded edges of the rectangle, e.g. 0, ▯ or ◯.

Preferably, the dimensions of the die are about 2 mm smaller than the corresponding dimensions of the final oblong dosage form.

After extrusion of the molten mixture and optional cooling of the extruded strand or extruded strands, the extrudates are preferably singulated. Singulation may preferably be performed by cutting up the extrudates by means of revolving or rotating knives, water jet cutters, wires, blades or with the assistance of laser cutters.

Singulation, e.g. cutting, yields slices of well defined length and weight having two opposing cut surfaces of oblong shape and a jacket (barrel). Typically, as a single dosage form is preferably formed from a single slice, each slice already contains the desired dosage of the pharmaceutically active ingredient (A) and the desired amount of polymer (C) as well as optionally present further excipients, which are also intended to be contained in the final dosage form.

In a preferred embodiment, singulation is performed in a plane substantially orthogonal to the direction of extrusion. However, it is also possible that the plane of singulation, e.g., includes an angle to the direction of extrusion. Singulation, e.g. cutting, yields slices of well defined size, particularly of well defined volume and surface area. The surface area is the sum of the two opposing cut surfaces of oblong shape and the area of the jacket (barrel).

In a preferred embodiment, at least 50% of the total surface of the slices obtained in step (b) is formed by the two opposing cut surfaces, more preferably at least 55%, still more preferably at least 60%, yet more preferably at least 65%, most preferably at least 70% and in particular at least 75%.

In a preferred embodiment, the relative ratio of the area of the two cut surfaces S to the area of the jacket (barrel) of the slice (extrudate) is at least 0.1, 0.2, 0.3, 0.4 or 0.5; more preferably at least 0.6, 0.7, 0.8, 0.9 or 1.0; still more preferably at least 1.1, 1.2, 1.3, 1.4 or 1.5; yet more preferably at least 1.6, 1.7, 1.8, 1.9 or 2.0; most preferably at least 2.1, 2.2, 2.3, 2.4 or 2.5; and in particular at least 2.6, 2.7, 2.8, 2.9 or 3.0. In another preferred embodiment, the relative ratio of the area of the two cut surfaces S to the area of the jacket (barrel) of the slice (extrudate) is at least 3.1, 3.2, 3.3, 3.4 or 3.5; more preferably at least 3.6, 3.7, 3.8, 3.9 or 4.0; still more preferably at least 4.1, 4.2, 4.3, 4.4 or 4.5; yet more preferably at least 4.6, 4.7, 4.8, 4.9 or 5.0; most preferably at least 5.1, 5.2, 5.3, 5.4 or 5.5; and in particular at least 5.6, 5.7, 5.8, 5.9 or 6.0.

A skilled person recognizes that composition of the extruded mass, size of the extrusion die and length of the slices that are singulated from the extruded strand determine the total weight of the dosage form (except an optionally applied coating), the drug content of the dosage form as well as its release profile. Said release profile is based on the different release properties of the opposing cut surfaces of the slices, which will essentially provide the top side and the back side of the dosage form, and the jacket (barrel) of the slices, which will essentially provide the circumferential rim of the dosage form.

An inert gas atmosphere is not necessary for intermediate or final storage of the optionally singulated extrudate or the final shape of the pharmaceutical dosage form according to the invention.

The singulated extrudate may be pelletized with conventional methods or be press-formed into tablets in order to impart the final shape to the pharmaceutical dosage form. It is, however, also possible not to singulate the extruded strands and, with the assistance of contrarotating calendar rolls comprising opposing recesses in their outer sleeve, to form them into the final shape, preferably a tablet, and to singulate these by conventional methods.

Should the optionally singulated extrudate not immediately be formed into the final shape, but instead cooled for storage, after the period of storage an inert gas atmosphere, preferably a nitrogen atmosphere, should be provided and must be maintained during heating of the stored extrudate up until plasticization and definitive shaping to yield the pharmaceutical dosage form.

The application of force in the extruder onto the at least plasticized mixture is adjusted by controlling the rotational speed of the conveying device in the extruder and the geometry thereof and by dimensioning the outlet orifice in such a manner that the pressure necessary for extruding the plasticized mixture is built up in the extruder, preferably immediately prior to extrusion. The extrusion parameters which, for each particular composition, are necessary to give rise to a pharmaceutical dosage form with a resistance to crushing of at least 300 N, preferably of at least 400 N, more preferably at least 500 N, may be established by simple preliminary testing.

For example, hot-melt extrusion may be performed by means of a twin-screw-extruder type Micro 27 GL 40 D (Leistritz, Nürnberg, Germany), screw diameter 27 mm. Screws having eccentric ends may be used. A heatable die may be used. The entire extrusion process should be performed under nitrogen atmosphere. The extrusion parameters may be adjusted e.g. to the following values: rotational speed of the screws: 100 Upm; delivery rate: 4 kg/h; product temperature: 125° C.; and jacket temperature: 120° C.

Alternatively, hot-melt extrusion may be performed by means of a planetary-gear extruder. Planetary-gear extruders are known and described inter alia in detail in Handbuch der Kunststoff-Extrusionstechnik I (1989) "Grundlagen" in Chapter 1.2 "Klassifizierung von Extrudern", pages 4 to 6. A suitable planetary gear extruder is, for example, an extruder type BCG 10 (LBB Bohle, Ennigerloh, Germany) having four planetary spindles and an extrusion die. A gravimetrical dosing of 3.0 kg/h is suitable. The extrusion may be performed, for example, at a rotational speed of 28.6 rmp and a product temperature of about 88° C.

The shaping of the pharmaceutical dosage form according to the invention is of particular importance. The final shape of the pharmaceutical dosage form may either be provided during the hardening of the mixture by applying heat and force or in a subsequent step. In both cases, the mixture of all components is preferably in the plastified state, i.e. preferably, shaping is performed at a temperature at least above the softening point of component (C).

Shaping can be performed, e.g., by means of a tabletting press comprising die and plunger (punch) of appropriate shape.

In a preferred embodiment, the plunger is an H-plunger so that the cross section of the pharmaceutical dosage form assumes the form of a H.

In another preferred embodiment, the plunger is a conventional oblong plunger yielding biconvex oblong tablets having a circumferential rim.

The process for the preparation of the pharmaceutical dosage form according to the invention is preferably performed continuously. Preferably, the process involves the extrusion of a homogeneous mixture comprising components (A) and (C). It is particularly advantageous if the obtained intermediate, e.g. the strand obtained by extrusion, exhibits uniform properties. Particularly desirable are uniform density, uniform distribution of the active compound, uniform mechanical properties, uniform porosity, uniform appearance of the surface, etc. Only under these circumstances the uniformity of the pharmacological properties, such as the stability of the release profile, may be ensured and the amount of rejects can be kept low. It has been surprisingly found that the above properties may be obtained by means of twin-screw-extruders and planetary-gear-extruders, twin-screw-extruders being particularly preferred.

It has been surprisingly found that the process according to the invention overcomes optical defects and a structural weakness that was observed in hot-melt extruded tablets manufactured from cylindrical extrusion strands having a circular cross-section and press-forming the extrudates by means of H-plungers.

It was surprisingly found that the resulting extrudates having oblong cross-section according to the invention are able to fill the tabletting punch more perfectly and thus, solve the observed issues.

Further, it was found that when using an oblong die extrusion is smoothly possible without modifications of the parameters. Using an oblong-shaped extrusion die leads to a lower melt temperature and to a lower back pressure. This indicates a more polymer protecting process.

Thus, tabletting leads to a superior quality, if the mass is hot-melt extruded through the oblong-shaped die, for "standard" (biconvex) oblong-shape as well as for H-shape. Resistance to crushing (breaking strength) is at least comparable or higher for tablets from oblong extrudates, the deformed H-shaped dosage forms show significantly less defects.

Still further, it has been surprisingly found that dissolution speeds up for tablets formed from oblong-shaped extrudates in comparison to that derived from cylindrical extrudates having a circular cross-section.

Summing up, extruding through oblong-shaped dies is advantageous if the extrudate is to be formed to an oblong-shaped tablet. In particular, typical defects of oblong H-shaped tablets can be overcome.

A further aspect of the invention relates to a hot-melt extruded pharmaceutical dosage form obtainable by the process described above.

A further aspect of the invention relates to a packaging containing the pharmaceutical dosage form according to the invention and an oxygen scavenger. Suitable packages include blister packages and bottles, such as glass bottles or bottles made from thermoplastic polymers.

Oxygen scavengers and the application thereof in pharmaceutical packaging are known to the skilled artisan. In a preferred embodiment, the oxygen scavenger is selected from the group consisting of metal-catalyzed oxidizable organic polymers and anti-oxidants. It has been surprisingly found that the storage stability of the pharmaceutical dosage form can be increased when keeping the oxygen content of the atmosphere within the packaging low. Methods for packaging pharmaceutical dosage forms and the application of suitable oxygen scavengers are known to the skilled artisan. In this regard it can be referred to e.g. D. A. Dean, Pharmaceutical Packaging Technology, Taylor & Francis, 1st ed.; F. A. Paine et al., Packaging Pharmaceutical and Healthcare Products, Springer, 1st ed.; and O. G. Piringer et al., Plastic Packaging: Interactions with Food and Pharmaceuticals, Wiley-VCH, 2nd ed.

The pharmaceutical dosage form according to the invention is suitable to avoid various misuses, particularly
  accidental misuse (e.g. unintentional);
  recreational misuse; and
  experienced drug misuse.

A further aspect of the invention relates to the use of an opioid for the manufacture of the pharmaceutical dosage form as described above for the treatment of pain.

A further aspect of the invention relates to the use of a pharmaceutical dosage form as described above for avoiding or hindering the abuse of the pharmacologically active compound (A) contained therein.

A further aspect of the invention relates to the use of a pharmaceutical dosage form as described above for avoiding or hindering the unintentional overdose of the pharmacologically active compound (A) contained therein.

In this regard, the invention also relates to the use of a pharmacologically active compound (A) as described above and/or a synthetic or natural polymer (C) as described above for the manufacture of the pharmaceutical dosage form according to the invention for the prophylaxis and/or the treatment of a disorder, thereby preventing an overdose of the pharmacologically active compound (A), particularly due to comminution of the pharmaceutical dosage form by mechanical action.

Further, the invention relates to a method for the prophylaxis and/or the treatment of a disorder comprising the administration of the pharmaceutical dosage form according to the invention, thereby preventing an overdose of the pharmacologically active compound (A), particularly due to comminution of the pharmaceutical dosage form by mechanical action. Preferably, the mechanical action is selected from the group consisting of chewing, grinding in a mortar, pounding, and using apparatuses for pulverizing conventional pharmaceutical dosage forms.

The invention is explained below with reference to examples. These explanations are given merely by way of example and do not limit the general concept and scope of the invention.

Example 1

Oblong shaped extrusion dies with the measurements 5*15 mm and 7*18 mm were investigated.

A powder blend was prepared. The composition is given in the table here below:

| Example 1 per tablet [mg] | Excipient | [%] |
|---|---|---|
| 174.72 | Tapentadol HCL | 38.83 |
| 166.83 | Polyethylenoxide 7000000 | 37.07 |
| 63.00 | Hypromellose 100000 mPa*s | 14.00 |
| 45.00 | Macrogol 6000 | 10.00 |
| 0.45 | α-Tocopherol | 0.10 |
| 450.00 | | |

The powder blend was the basis for the following sub-examples:

| Sub-Example | Description |
|---|---|
| 1-1 | Extrudate 6 mm round die |
| 1-2 | Extrudate 5 × 15 mm oblong-shaped die |
| 1-3 | Tablets 7 × 17 mm oblong from extrudate „round" |
| 1-4 | Tablets 7 × 17 mm H9-shaped from extrudate „round" |
| 1-5 | Tablets 7 × 17 mm oblong from extrudate „oblong" |
| 1-6 | Tablets 7 × 17 mm H9-shaped from extrudate „oblong" |

The investigated sub-examples allow for a comparison of the extrusion die's influence on the tablet properties.

Example 2

A powder blend was prepared. The composition is given in the table here below:

| Example 2 per tablet [mg] | Excipient | [%] |
| --- | --- | --- |
| 291.2 | Tapentadol HCL | 41.6 |
| 245.0 | Polyethylenoxide 7000000 | 35.0 |
| 98.0 | Hypromellose 100000 mPa*s | 14.0 |
| 65.1 | Macrogol 6000 | 9.3 |
| 0.7 | α-Tocopherol | 0.1 |
| 700.0 | | |

The powder blend was the basis for the following sub-examples:

| Sub-Example | Description |
| --- | --- |
| 2-1 | Extrudate 7 mm round die |
| 2-2 | Extrudate 7 × 18 mm oblong-shaped die |
| 2-3 | Tablets 9 × 21 mm oblong from extrudate »round« |
| 2-4 | Tablets 9 × 21 mm H0-shaped from extrudate »round« |
| 2-5 | Tablets 8.6 × 22.6 mm H1-shaped from extrudate »round« |
| 2-6 | Tablets 9 × 21 mm oblong from extrudate »oblong« |
| 2-7 | Tablets 9 × 21 mm H0-shaped from extrudate »oblong« |
| 2-8 | Tablets 8.6 × 22.6 mm H1-shaped from extrudate »oblong« |

The investigated sub-examples allow for a comparison of the extrusion die's influence on the tablet properties.

Methods of Manufacture a) Extrusion

Extrusion was performed on a Leistritz® PH27 micro twin-screw extruder with the throughput reduced to 3.5 kg/h. The temperatures of the individual heating zones were adjusted to values from 30° C. to 135° C.

b) Cutting

Cutting was done using a Schlicht® CC250 cutting machine for the round extrudates and by hand using a bread slicer for the oblong-shaped extrudates. Manual cutting led to a highly inferior quality of the extrudates including, but not limited to, much more surface defects.

Tablet Forming

Tablet forming was conducted on a Korsch® EK0 for the 7*17 mm H9 format. All other tablets were shaped on a Kilian® S250.

Analytical Methods a) Dimensions

Dimensions were measured using a manual caliber.

b) Resistance to Crushing

Resistance to crushing was measured on a Sotax® HT100 with plain brackets. Tablet orientation was lengthwise.

c) Dissolution

Dissolution measurement was conducted according to Ph Eur. 2.9.3 in a paddle apparatus with sinker, rotation speed 50 rpm at 37° C. in simulated intestinal fluid (900 ml, pH 6.6, $KH_2PO_4$+NaOH). 6 Measurements were made for each sample (n=6). Release was monitored by UV spectroscopy at 271 nm.

Results a) Extrusion—Example 1

The extrusion was possible without any unexpected issues. As exactly identical extruder settings were used, a remarkable observation can be made.

| Extrusion die | 6 mm (round) | 5 × 15 mm (oblong) |
| --- | --- | --- |
| Melt temperature [° C.] | 119 | 91 |
| Power consumption [%] | 68 | 68 |
| Melt pressure [bar] | 79 | 75 |

The above data shows the melt temperature of the extrudate gone through the round die to be significantly higher than that of the extrudate produced with the oblong-shaped die. As the strands' appearances were visually identical the use of the oblong-shaped leads to a lower melt temperature and is therefore less demanding for the material. The back pressure was observed to be minimal lower for the oblong-shaped die than for the round one.

a) Extrusion—Example 2

The extrusion was possible without any unexpected issues. As exactly identical extruder settings were used, a remarkable observation can be made.

| Extrusion die | 7 mm (round) | 7 × 18 mm (oblong) |
| --- | --- | --- |
| Melt temperature [° C.] | 128 | 90 |
| Power consumption [%] | 67 | 67 |
| Melt pressure [bar] | 74 | 59 |

The above data shows again shows the melt temperature of the extrudate gone through the round die to be significantly higher than that of the extrudate produced with the oblong-shaped die. As the strands' appearances were visually identical the use of the oblong-shaped leads to a lower melt temperature and is therefore less demanding for the material.

The back pressure was observed to be about 20% lower for the oblong-shaped die than for the round one.

b) Tablet Forming: Dimensions, Appearance, and Resistance to Crushing

Oblong Biconvex Tablets:

| Example 1 | 1-3 | 1-5 |
| --- | --- | --- |
| Extrusion Die | 6 mm round | 5*15 mm oblong |
| Appearance (% with navel, n = 50) | 22 | 0 |
| Length [mm] (mean, min.-max., n = 10) | 16.28 (16.22-16.35) | 16.76 (16.73-16.81) |
| Width [mm] (mean, min.-max., n = 10) | 6.99 (6.98-7.00) | 6.94 (6.91-6.95) |
| Thickness [mm] (mean, min-max., n = 10) | 4.82 (4.79-4.84) | 4.73 (4.66-4.95) |
| Resistance to Crushing [N] (mean, n = 50), range given in parenthesis | 931 (474->1000) | 978 (405->1000) |

As the resistance to crushing test is performed at the upper end of the range of the apparatus, the mean value is only informative.

The results show a superiority of sub-example 1-5 over 1-3. In the latter 22% of the tablets showed a navel against the total absence of navels in the first. This finding hints for a better forming of the tablets and is supported by the length measurement: 1-5 forms out the punch more completely which results in significantly longer tablets. Resistance to crushing is slightly higher for 1-5. The deformed tablets of both batches are of similar appearance.

Oblong, H-Shaped Tablets:

| Example 1 | 1-4 | 1-6 |
|---|---|---|
| Extrusion Die | 6 mm round | 5*15 mm oblong |
| Appearance (% with navel, n = 50) | 0 (n = 46) | 0 (n = 43) |
| Length [mm] (mean, min.-max., n = 10) | 16.53 (16.52-16.55) | 16.85 (16.80-16.89) |
| Width [mm] (mean, min.-max., n = 10) | 7.04 (7.03-704) | 6.99 (6.99-7.00) |
| Thickness [mm] (mean, min-max., n = 10) | 4.13 (4.05-4.18) | 4.01 (3.91-4.12) |
| Resistance to Crushing [N] (mean, n = 50), range given in parenthesis | 542 (249->1000) | 510 (294->1000) |

As the resistance to crushing test is performed at the upper end of the range of the apparatus, the mean value is only informative.

The results presented in the above table show a superiority of sub-example 1-6 over 1-4. Although there are no naveled tablets in both batches sub-example 1-6 forms out more accurately. This is again a conclusion from the length measurement: 1-6 forms out the punch more completely which results in significantly longer tablets. Even if a superiority in the resistance to crushing cannot be shown, the picture of the tablets taken after this test hints for an advantage of sub-example 1-6. While most tablets of 1-4 show a characteristic hole in the trough section which results from the previously noted tearing apart of the H-shape, only a single tablet of 1-6 show a hole, but outside the trough area. This finding indicates an increased inherent strength of sub-example 1-6.

Oblong Biconvex Tablets:

| Example 2 | 2-3 | 2-6 |
|---|---|---|
| Extrusion Die | 7 mm round | 7*18 mm oblong |
| Appearance (% with navel, n = 50) | 0 | 6 |
| Length [mm] (mean, min.-max., n = 10) | 20.26 (20.24-20.27) | 20.67 (20.57-20.84) |
| Width [mm] (mean, min.-max., n = 10) | 9.00 (8.98-9.03) | 8.95 (8.91-9.01) |
| Thickness [mm] (mean, min-max., n = 10) | 5.38 (5.36-5.42) | 5.31 (5.13-5.46) |
| Resistance to Crushing [N] (mean, n = 50), range given in parenthesis | 1000 (998->1000) | 942 (483->1000) (n = 49) |

As the resistance to crushing test is performed at the upper end of the range of the apparatus, the mean value is only informative.

The above data indicates sub-example 2-6 to have more navels. This could be an artifact of the manual cutting and should not be overrated. The length measurement again shows the oblong-shaped extrudate to fill the punch more completely, as previously mentioned. Resistance to crushing is quite similar but values below about 1000N are only measured for sub-example 2-6 and can possibly be linked to the appearance defects. The appearance of the tablets after the test is quite similar.

Oblong, H-Shaped Tablets:

| Example 2 | 2-4 | 2-7 |
|---|---|---|
| Extrusion Die | 7 mm round | 7*18 mm oblong |
| Appearance (% with navel, n = 50) | 2 | 34 |
| Length [mm] (mean, min.-max., n = 10) | 20.33 (20.29-20.38) | 20.68 (20.52-20.84) |
| Width [mm] (mean, min.-max., n = 10) | 9.01 (8.99-9.02) | 8.99 (8.96-9.02) |
| Thickness [mm] (mean, min-max., n = 10) | 4.32 (4.29-4.34) | 4.30 (4.21-4.39) |
| Resistance to Crushing [N] (mean, n = 50), range given in parenthesis | 292 (211-444) (n = 47) | 479 (267->1000) |

As the resistance to crushing test is performed at the upper end of the range of the apparatus, the mean value is only informative.

As can be seen from the above table, sub-example 2-7 has more optical defects and again the oblong-shaped extrudate fill the tabletting punch more completely. Resistance to crushing is about 60% higher than that of the tablets from the round extrudate. The photograph of the tablets after the test shows again an advantage for the oblong-shaped extrudate.

Oblong, H-Shaped Tablets:

| Example 2 | 2-5 | 2-8 |
|---|---|---|
| Extrusion Die | 7 mm round | 7*18 mm oblong |
| Appearance (% with navel, n = 50) | 44 | 52 |
| Length [mm] (mean, min.-max., n = 10) | 21.79 (21.70-21.87) | 22.04 (21.97-22.12) |
| Width [mm] (mean, min.-max., n = 10) | 8.62 (8.60-8.65) | 8.61 (8.60-8.61) |
| Thickness [mm] (mean, min-max., n = 10) | 4.23 (4.20-4.25) | 4.24 (4.13-4.34) |
| Resistance to Crushing [N] (mean, n = 50), range given in parenthesis | 353 (215->1000) | 550 (249->1000) |

As the resistance to crushing test is performed at the upper end of the range of the apparatus, the mean value is only informative.

There are practically no qualitative differences between tablets that are H0-shaped and those that are H1-shaped. The amount of tablets showing a navel is more similar between sub-examples 2-5 and 2-8 than it has been before. This however should not be overrated due to the less accurate quality of the manually cut extrudates.

The results of in vitro dissolution experiments are displayed in FIGS. 6 to 10.

Figure 6:
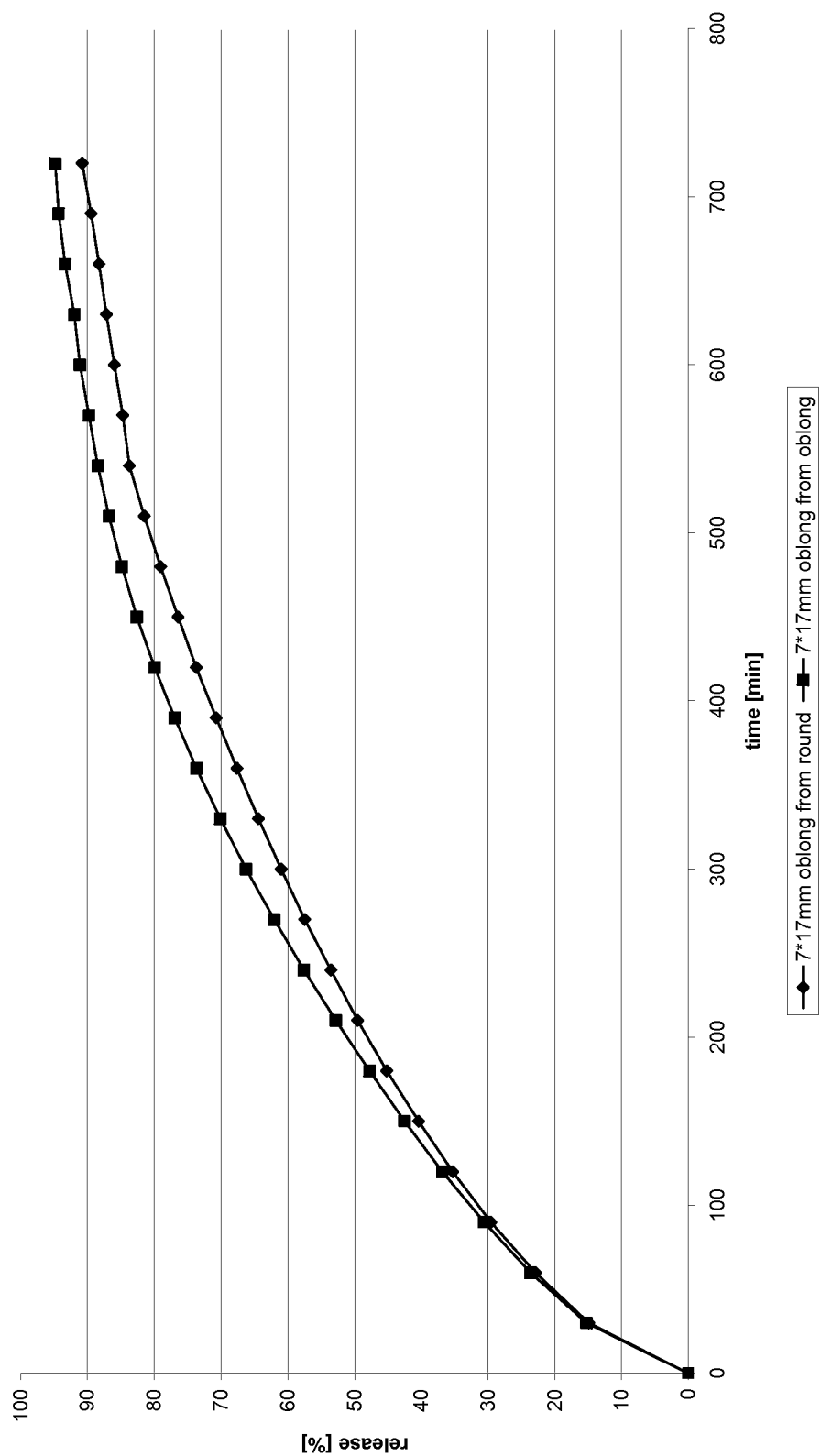
FIG. 6 shows the dissolution profile of example 1 shaped to a 7*17 mm oblong tablet.

FIG. 6: Dissolution profile of example 1 shaped to a 7*17 mm oblong tablet, mean, n=3

Figure 7:
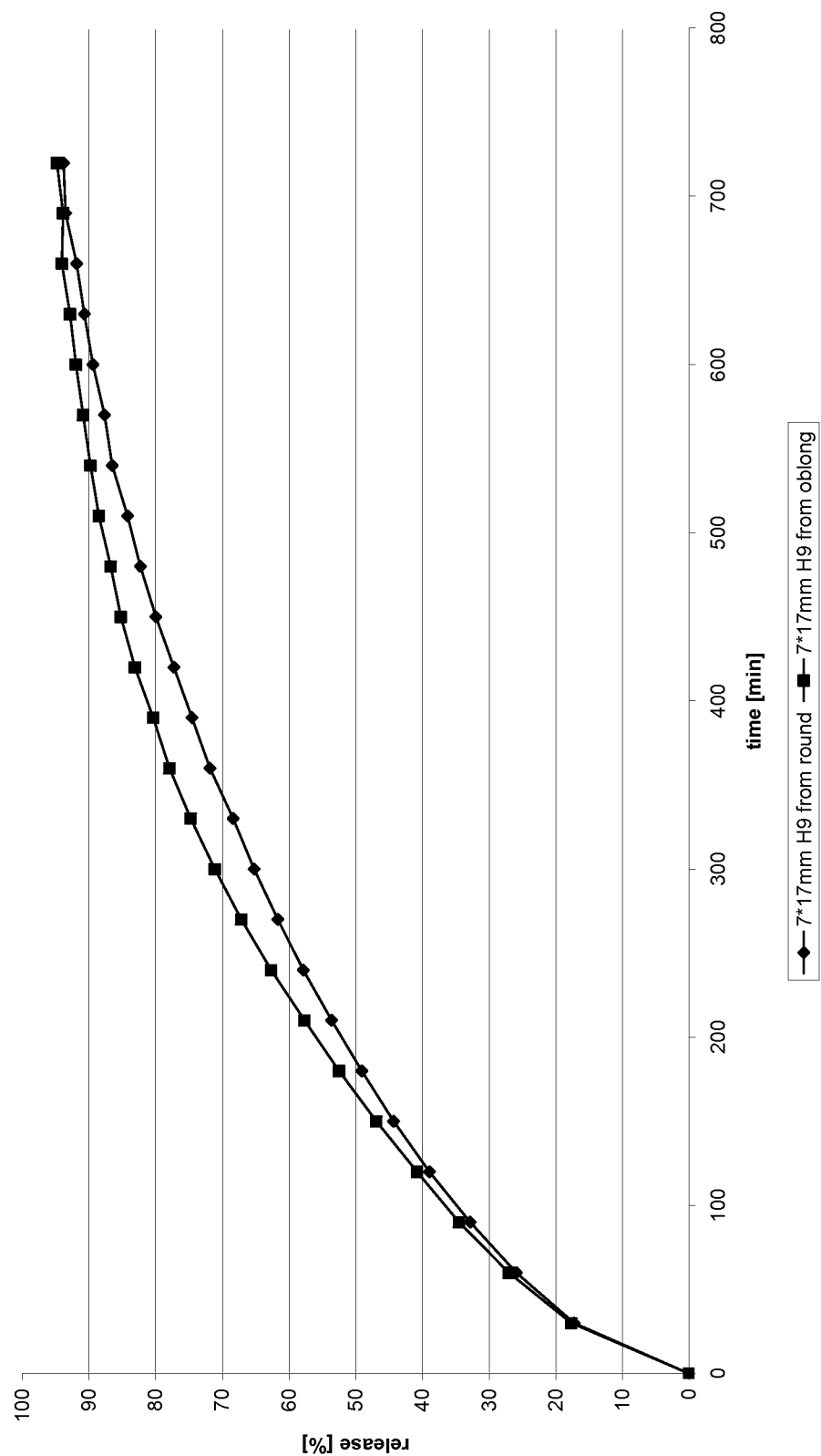
FIG. 7 shows the dissolution profile of example 1 shaped to a 7*17 mm H9-shaped tablet.

FIG. 7: Dissolution profile of example 1 shaped to a 7*17 mm H9-shaped tablet, mean, n=3

Figure 8:
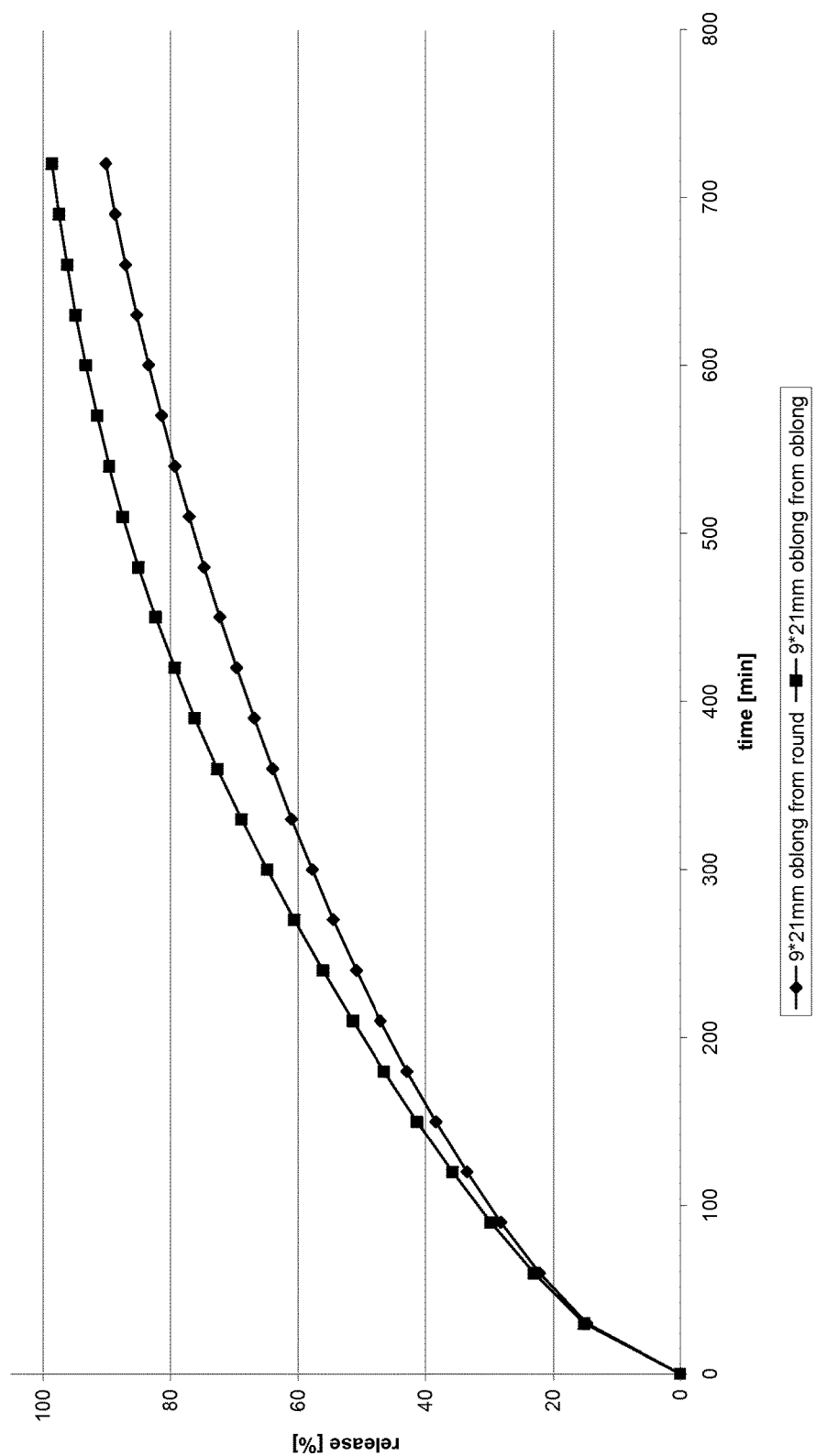
FIG. 8 shows the dissolution profile of example 2 shaped to a 9*21 mm oblong tablet.

FIG. 8: Dissolution profile of example 2 shaped to a 9*21 mm oblong tablet, mean, n=3

Figure 9:
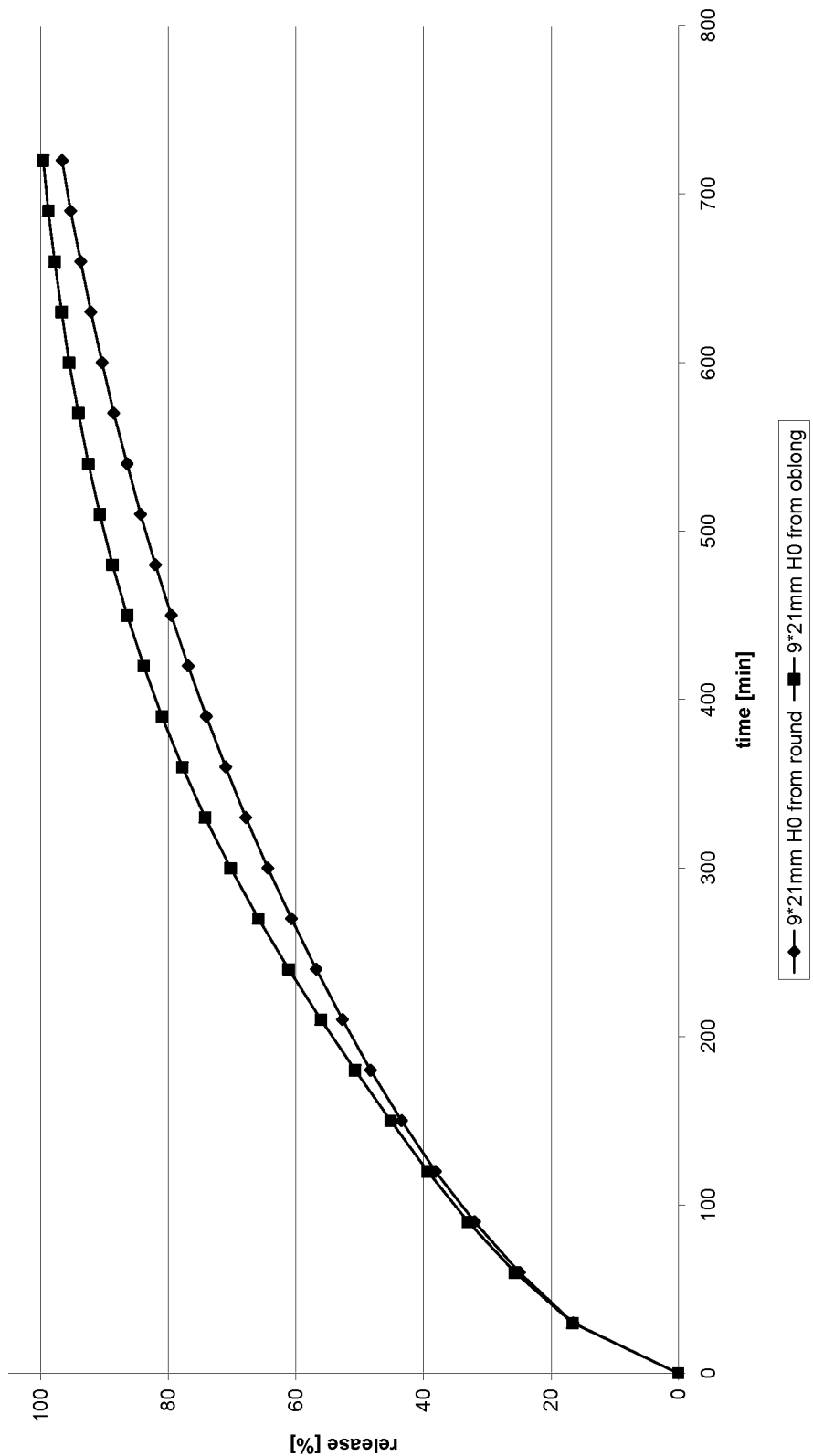
FIG. 9 shows the dissolution profile of example 2 shaped to a 9*21 mm H0-shaped tablet.

FIG. 9: Dissolution profile of example 2 shaped to a 9*21 mm H0-shaped tablet, mean, n=3

Figure 10:
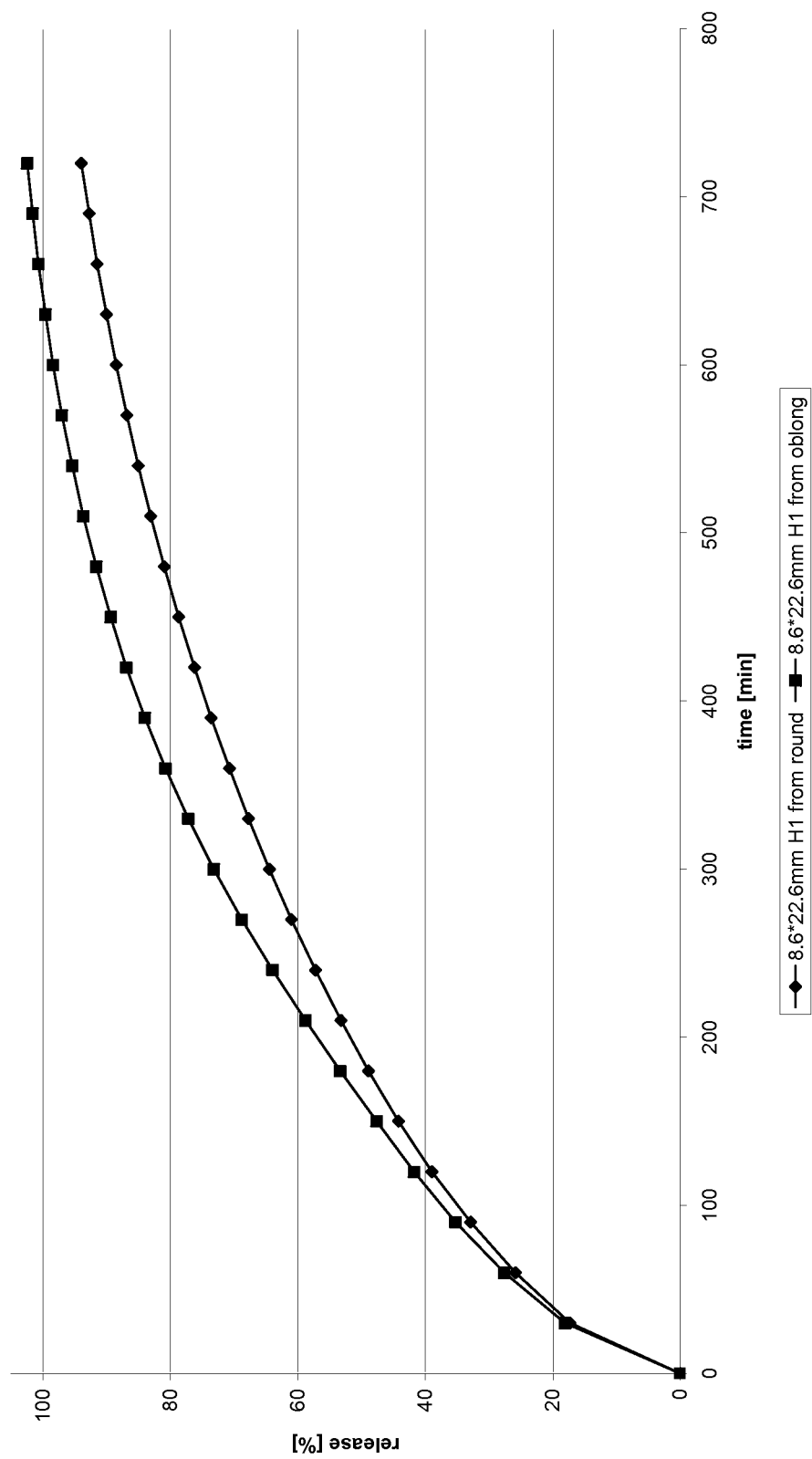
FIG. 10 shows the dissolution profile of example 2 shaped to a 8.6*22.6 mm H1-shaped tablet.

FIG. 10: Dissolution profile of example 2 shaped to a 8.6*22.6 mm H1-shaped tablet, mean, n=3

The dissolution profiles of all produced tablets show an acceleration of the oblong tablet formed from the oblong-shaped extrudate compared to the oblong tablet formed from the cylindrical extrudate, irrespective from the tablet's format.

Figure 11:
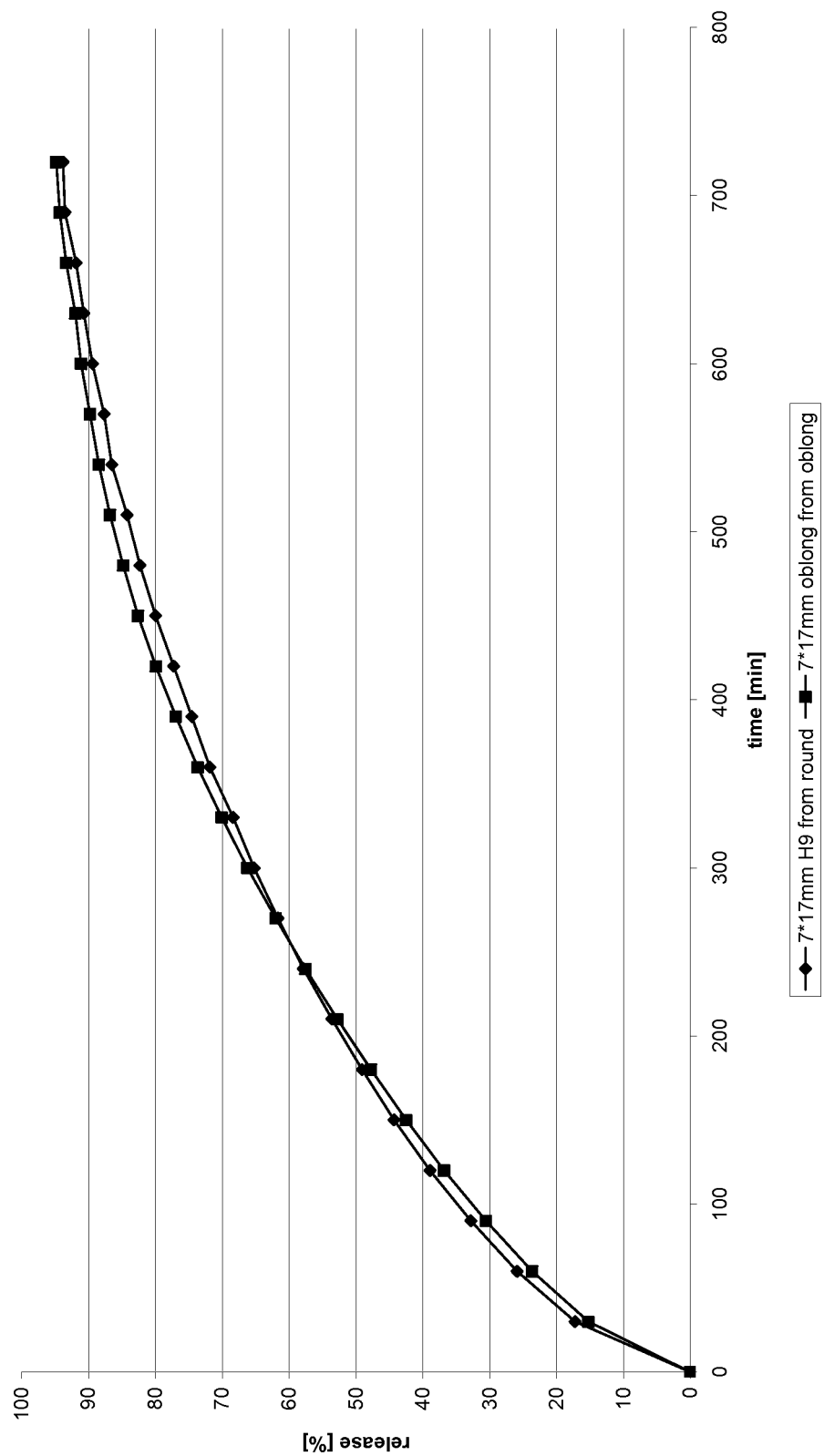
FIG. 11 shows the dissolution for example 1: comparison of H9 format from round extrudate to oblong format from oblong extrudate.
Figure 12:
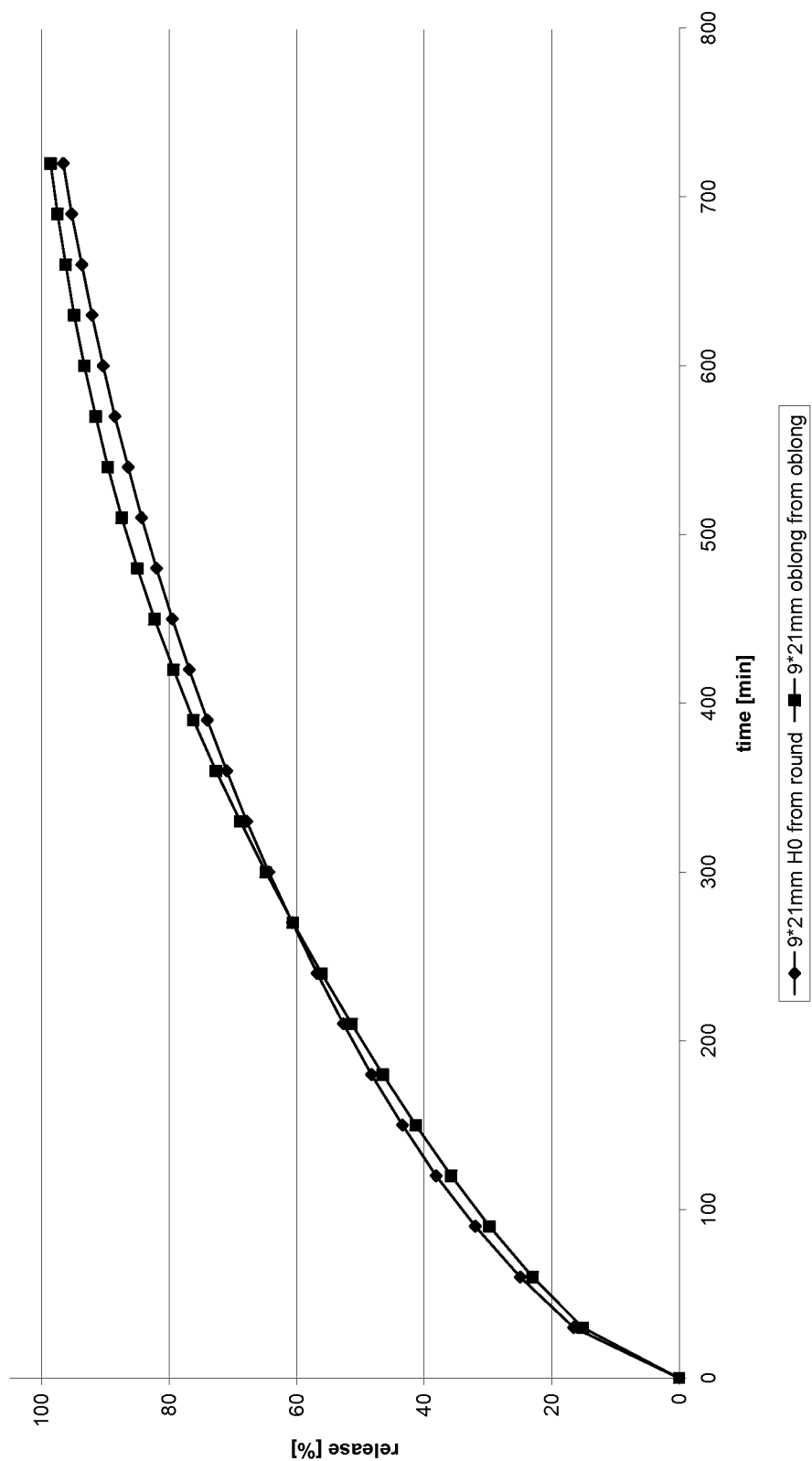
FIG. 12 shows the dissolution for example 2: comparison of H0 format from round extrudate to oblong format from oblong extrudate.

The extent of this dissolution acceleration is illustrated by FIGS. 11 and 12. By using an oblong shaped extrusion die acceleration in dissolution for the non H-shaped oblong tablet is achieved that is equivalent to that of the use of an H-shaped tablet punch made from an extrudate made with a cylindrical die.

FIG. 11: Dissolution for example 1: comparison of H9 format from round extrudate to oblong format from oblong extrudate, mean, n=3

FIG. 12: Dissolution for example 2: comparison of H0 format from round extrudate to oblong format from oblong extrudate, mean, n=3

It becomes evident from the dissolution data that dissolution speeds up for oblong tablets formed from oblong-shaped extrudates in comparison to that derived from cylindrical extrudates. This acceleration has an extent that apparently makes it possible to achieve sufficiently fast dissolution with (conventional) biconvex oblong tablets, i.e. as far as the dissolution rate is concerned, there is no need to provide the oblong tablets in H-shaped format.

This finding is unexpected and indicates some structural changes within the extrudate in dependency from the extrusion die chosen or hints for an un-isometric behavior of the extrudate as such.

Further, extrusion through oblong-shaped dies is advantageous if the extrudate is to be formed to an oblong-shaped tablet. Rupture during the resistance to crushing test does not occur at the desired breaking forces. Optical defects ("navel") might be reduced or even completely eliminated. The deviating dissolution behavior hints for some structural changes in the extrudate.

Example 3

A powder blend was prepared. The composition is given in the table here below:

| Example 3 per tablet [mg] | Excipient | [%] |
|---|---|---|
| 40.0 | Tramadol HCL | 18.60 |
| 122.1 | Polyethylenoxide 7000000 | 56.80 |
| 21.5 | Hypromellose 100000 mPa*s | 10.00 |
| 29.2 | Macrogol 6000 | 13.56 |
| 0.4 | α-Tocopherol | 0.20 |
| 1.8 | Citric acid anhydrous | 0.84 |
| 215.0 | | |

The powder blend was the basis for the following sub-examples:

| Sub-Example | Description |
|---|---|
| 3-1 | oblong slices |
| 3-2 | oblong slices, folded twice, then tabletted |

In analogy to example 2, extrusion was performed using a 7×18 mm oblong-shaped die. In sub-example 3-1 the crude extruded slice was investigated without further modification. In sub-example 3-2 the crude extruded slice was folded twice and thereafter, press-formed into tablets with 9 mm diameter and a radius of curvature of 7.2 mm.

Figure 13:
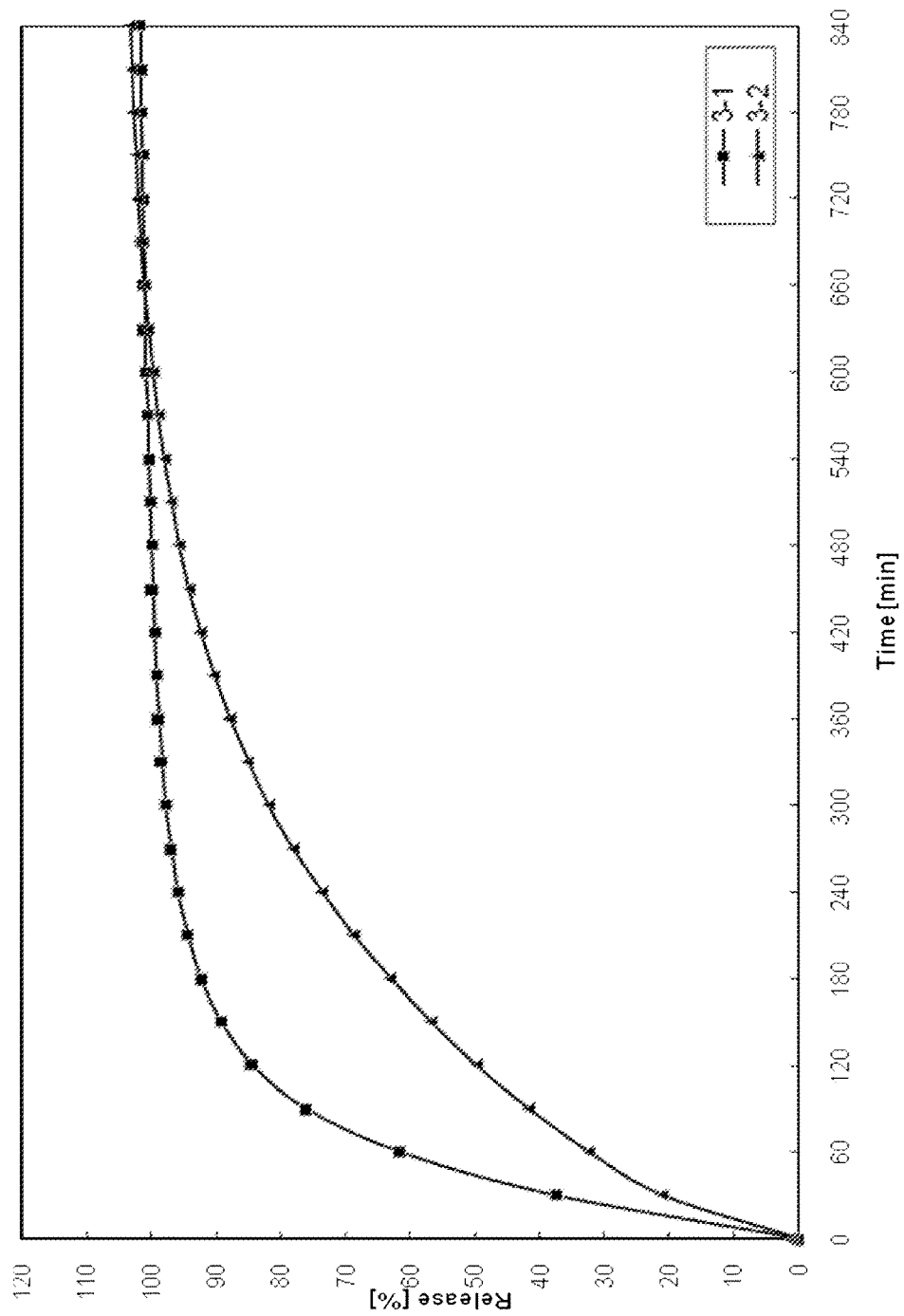
FIG. 13 shows the dissolution for example 3: comparison of oblong crude extrudate to tablet from extrudate that has been folded twice before.

The release profile for tramadol HCl was measured in analogy to example 2. The results are shown in FIG. 13.

The invention claimed is:

1. A hot-melt extruded tablet having a front side and an opposite back side, the tablet comprising:
   (i) a pharmacologically active ingredient (A) embedded in a matrix comprising a polymer (C);
   (ii) an oblong shape imparted by post-hot-melt-extrusion pressing of a hot-melt extrudate on a tablet-press; and (iii) a circumferential rim between the front and back sides;
wherein the tablet exhibits a breaking strength of at least 300 N;
wherein the tablet exhibits controlled release of the pharmacologically active ingredient (A);
wherein the tablet comprises a direction of extrusion that runs parallel to a direction of extrusion of the hot-melt extrudate through an extrusion die;
wherein the tablet comprises a longitudinal direction of extension, which longitudinal direction of extension is the longest dimension of the tablet and runs orthogonal to the direction of extrusion;
wherein the tablet comprises a transversal direction of extension orthogonal to the longitudinal direction of extension and orthogonal to the direction of extrusion;
wherein the oblong shape is imparted by post-extrusion pressing of the extrudate on the tablet-press in a pressing direction parallel to said direction of extrusion and orthogonal to both said longitudinal direction of extension and said transversal direction of extension; and
wherein the tablet has a core having a morphological orientation caused by the hot-melt extrusion that is substantially orthogonal to the longitudinal direction of extension of the tablet.

2. The tablet according to claim 1, wherein the pharmacologically active ingredient (A) is an opioid.

3. The tablet according to claim 1, wherein polymer (C) is a polyalkylene oxide having a weight average molecular weight of at least 200,000 g/mol.

4. The tablet according to claim 1, wherein the content of polymer (C) is at least 30 wt.-%, based on the total weight of the tablet.

5. The tablet according to claim 1, wherein the relative length ratio of the longitudinal direction of extension to the transversal direction of extension is at least 1.1:1.

6. The tablet according to claim 1, further comprising a film coating.

7. The tablet according to claim 1, which releases the pharmacologically active ingredient (A) under in vitro conditions in artificial gastric juice according to the following release profile:
after 0.5 h at least 5 wt.-%,
after 1 h at least 10 wt.-%,
after 3 h at least 20 wt.-%,
after 6 h at least 35 wt.-%, and
after 12 h at least 55 wt.-%,
based on the total weight of the pharmacologically active ingredient (A) initially contained in the tablet.

8. A process for the manufacture of a hot-melt extruded pharmaceutical tablet according to claim 1, said process comprising the steps of:

(a) hot-melt extruding a mass comprising:
the pharmacologically active ingredient (A), and
the polymer (C),
through an oblong die thereby obtaining an extrudate with an oblong cross-section;
(b) cutting said extrudate into slices having two opposing cut surfaces of oblong shape;
(c) placing said slices into a tabletting tool comprising an upper punch and a lower punch in a manner so that the two opposing cut surfaces of oblong shape face said upper and lower punch, respectively;
(d) press-forming tablets from the slices; and
(e) optionally, applying a film coating.

9. The process according to claim 8, wherein step (a) is performed by means of a twin-screw-extruder.

10. The process of claim 8, wherein at least 50% of the total surface of the slices obtained in step (b) is formed by the two opposing cut surfaces.

11. The process of claim 9, wherein at least 50% of the total surface of the slices obtained in step (b) is formed by the two opposing cut surfaces.

12. The tablet according to claim 1 comprising a monolithic core.

13. The tablet according to claim 1, which exhibits a release per unit area of the pharmacologically active ingredient (A) through the front side and the opposite back side that is faster than the release through the circumferential rim.

14. A hot-melt extruded tablet having a front side and an opposite back side, the tablet comprising:
(i) a pharmacologically active ingredient (A) in a matrix comprising a polymer (C);
(ii) an oblong shape imparted by post-hot-melt-extrusion pressing of a hot-melt extrudate on a tablet-press; and
(iii) a circumferential rim between the front and back sides;
wherein the tablet exhibits a breaking strength of at least 300 N;
wherein the tablet exhibits controlled release of the pharmacologically active ingredient (A);
wherein the tablet has a direction of extrusion that runs parallel to a direction of extrusion of said hot-melt extrudate through an extrusion die;
wherein the tablet has a longitudinal direction of extension, which is the longest dimension in the tablet and runs orthogonal to the direction of extrusion;
wherein the tablet has a transversal direction of extension that runs orthogonal to both the direction of extrusion and the longitudinal direction of extension; and
wherein the oblong shape is imparted by compressing the hot-melt extrudate parallel to the direction of extrusion and orthogonal to the longitudinal direction of extension.

* * * * *